US011191786B2

(12) United States Patent
Tamai et al.

(10) Patent No.: US 11,191,786 B2
(45) Date of Patent: Dec. 7, 2021

(54) AGENTS FOR PROMOTING TISSUE REGENERATION BY RECRUITING BONE MARROW MESENCHYMAL STEM CELLS AND/OR PLURIPOTENT STEM CELLS INTO BLOOD

(75) Inventors: Katsuto Tamai, Osaka (JP); Yasufumi Kaneda, Osaka (JP); Takehiko Yamazaki, Osaka (JP); Takenao Chino, Osaka (JP); Kotaro Saga, Osaka (JP); Mayumi Endo, Osaka (JP)

(73) Assignees: STEMRIM INC., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 13/503,329

(22) PCT Filed: Oct. 28, 2010

(86) PCT No.: PCT/JP2010/069133
§ 371 (c)(1),
(2), (4) Date: Jun. 20, 2012

(87) PCT Pub. No.: WO2011/052668
PCT Pub. Date: May 5, 2011

(65) Prior Publication Data
US 2012/0251510 A1  Oct. 4, 2012

(30) Foreign Application Priority Data
Oct. 28, 2009  (JP) .............................. JP2009-247143

(51) Int. Cl.
*A61K 48/00* (2006.01)
*A61K 38/00* (2006.01)
*A61K 35/28* (2015.01)
*C07K 14/47* (2006.01)

(52) U.S. Cl.
CPC .............. *A61K 35/28* (2013.01); *C07K 14/47* (2013.01); *A61K 48/00* (2013.01)

(58) Field of Classification Search
None
See application file for complete search history.

(56) References Cited

U.S. PATENT DOCUMENTS

| 3,896,810 | A | 7/1975 | Akiyama |
| 4,732,155 | A | 3/1988 | Zetter et al. |
| 5,661,127 | A | 8/1997 | Bhatnagar et al. |
| 5,851,986 | A | 12/1998 | Takada et al. |
| 5,902,799 | A | 5/1999 | Hermann et al. |
| 7,288,250 | B2 | 10/2007 | Newman et al. |
| 7,470,538 | B2 | 12/2008 | Laughlin et al. |
| 7,585,504 | B2 | 9/2009 | Wu et al. |
| 8,673,580 | B2 | 3/2014 | Tamai et al. |
| 10,626,153 | B2 | 4/2020 | Bianchi et al. |
| 2002/0058019 | A1 | 5/2002 | Berenson et al. |
| 2003/0003482 | A1* | 1/2003 | Halle et al. ........................ 435/6 |
| 2003/0060410 | A1 | 3/2003 | Tracey et al. |
| 2004/0031072 | A1 | 2/2004 | La Rosa et al. |
| 2004/0053841 | A1 | 3/2004 | Tracey et al. |
| 2004/0156851 | A1 | 8/2004 | Newman |
| 2004/0191246 | A1 | 9/2004 | Connelly et al. |
| 2004/0242481 | A1 | 12/2004 | Bianchi et al. |
| 2004/0249448 | A1 | 12/2004 | Gault |
| 2004/0265971 | A1 | 12/2004 | Sato et al. |
| 2005/0014255 | A1 | 1/2005 | Tang et al. |
| 2005/0101564 | A1 | 5/2005 | Pilarski |
| 2005/0137165 | A1 | 6/2005 | Pilarski |
| 2005/0260174 | A1 | 11/2005 | Fraser et al. |
| 2006/0003312 | A1 | 1/2006 | Blau et al. |
| 2006/0035851 | A1 | 2/2006 | Bianchi et al. |
| 2006/0039896 | A1 | 2/2006 | Kleinsek et al. |
| 2006/0069064 | A1 | 3/2006 | Khaldoyanidi |
| 2006/0111287 | A1 | 5/2006 | Bianchi |
| 2006/0127373 | A1 | 6/2006 | Son et al. |

(Continued)

FOREIGN PATENT DOCUMENTS

| AU | 2003/228099 A1 | 1/2004 |
| AU | 2004/203732 A1 | 7/2004 |

(Continued)

OTHER PUBLICATIONS

Ehrchen et al., Journal of Leukocyte Biology, 2009, 86: 557-566.*
Turker et al., Pharm. World Sci., 2004, 26: 137-142; Abstract.*
Mansbridge, J. Biomater. Sci. Polymer Ed., Aug. 1, 2008, 19: 955-968.*
Simard et al., Neuron, 2006, 49: 489-502.*
Harrison et al., J. Biol. Chern., 1999,274: 8561-8569.*
Cairo et al., Blood, 1995,86:2509-2515.*
Brunner, FASEB J., 2009, 23: 351-361.*
Kim, S. et al. "Skin Regeneration Using Keratinocytes and Dermal Fibroblasts Cultured on Biodegradable Microspherical Polymer Scaffolds" *Journal of Biomedical Materials Research Part : Applied Biomaterials,* Nov. 2005, vol. 75, No. 2, pp. 369-377.

(Continued)

*Primary Examiner* — Ileana Popa
(74) *Attorney, Agent, or Firm* — Saliwanchik, Lloyd & Eisenschenk

(57) ABSTRACT

It was revealed that the intravenous administration of HMGB-1 and S100A8 promoted the healing of skin ulcer by recruiting bone marrow-derived cells to the site of skin ulcer. Furthermore, when HMGB-1 was intravenously administered to cerebral infarction model mice after creation of cerebral infarction, bone marrow-derived cells expressing nerve cell markers were detected in their brain. A marked cerebral infarct-reducing effect was observed in mice intravenously administered with HMGB-1 as compared to the control. The post-cerebral infarction survival rate was increased in the intravenous HMGB-1 administration group. The involvement of bone marrow pluripotent stem cells in the process of bone fracture healing was assessed using mice, and the result demonstrated that bone marrow-derived cells distant from the damaged site migrated to the bone fracture site to repair the damaged tissue.

6 Claims, 44 Drawing Sheets

Specification includes a Sequence Listing.

(56) References Cited

U.S. PATENT DOCUMENTS

| | | |
|---|---|---|
| 2006/0281674 A1 | 12/2006 | Tessier et al. |
| 2007/0154529 A1 | 7/2007 | Bullerdiek |
| 2007/0190023 A1 | 8/2007 | Battista et al. |
| 2007/0238663 A1 | 10/2007 | Capogrossi et al. |
| 2008/0214454 A1 | 9/2008 | Tracey et al. |
| 2008/0286324 A1 | 11/2008 | Stolen et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2009/0280488 A1 | 11/2009 | Okazawa |
| 2010/0280493 A1 | 11/2010 | Nayak |
| 2011/0091928 A1 | 4/2011 | Tamai et al. |
| 2011/0097309 A1 | 4/2011 | Tamai et al. |
| 2011/0104803 A1 | 5/2011 | Tamai et al. |
| 2012/0237504 A1 | 9/2012 | Brooks et al. |
| 2012/0251510 A1 | 10/2012 | Tamai et al. |
| 2018/0055886 A1 | 3/2018 | Tamai et al. |
| 2018/0072785 A1 | 3/2018 | Tamai et al. |
| 2019/0343924 A1 | 11/2019 | Tamai et al. |

FOREIGN PATENT DOCUMENTS

| | | | | |
|---|---|---|---|---|
| AU | WO 06/047820 | * | 11/2006 | ............. A61K 38/17 |
| CA | 2325226 | | 5/2001 | |
| CA | 2512512 A1 | | 7/2004 | |
| CA | 2 636 788 | | 5/2008 | |
| CN | 1439717 A | | 9/2003 | |
| CN | 1516739 A | | 7/2004 | |
| CN | 1671742 A | | 9/2005 | |
| CN | 101366728 A | | 2/2009 | |
| CN | 101374538 A | | 2/2009 | |
| CN | 102076350 A | | 5/2011 | |
| CN | 102443064 | | 5/2012 | |
| CN | 102711777 A | | 10/2012 | |
| EP | 0 791 601 A2 | | 8/1997 | |
| EP | 1 459 759 A1 | | 9/2004 | |
| EP | 2 039 367 | | 3/2009 | |
| EP | 2 055 308 | | 5/2009 | |
| EP | 2 284 255 A1 | | 2/2011 | |
| EP | 2 301 559 A1 | | 3/2011 | |
| EP | 2913058 B1 | | 12/2017 | |
| EP | 3556378 A1 | | 10/2019 | |
| EP | 3719117 A1 | | 10/2020 | |
| JP | H 9-227403 | | 9/1997 | |
| JP | 2001-321434 A | | 11/2001 | |
| JP | 2003-505506 A | | 2/2003 | |
| JP | 2005-512507 | | 5/2005 | |
| JP | 2005-537253 A | | 12/2005 | |
| JP | 2006510619 A | | 3/2006 | |
| JP | 2006-124389 A | | 5/2006 | |
| JP | 2006-517537 A | | 7/2006 | |
| JP | 2006-523085 A | | 10/2006 | |
| JP | 2007-320919 | | 12/2007 | |
| JP | 2008-507505 A | | 3/2008 | |
| JP | 2008511300 A | | 4/2008 | |
| JP | 2010503630 A | | 2/2010 | |
| KR | 20090078304 A | | 7/2009 | |
| RU | 2005102593 A | | 10/2005 | |
| RU | 2 410 125 C2 | | 1/2011 | |
| WO | WO 01/08683 A1 | | 2/2001 | |
| WO | WO 2002/074337 A1 | | 9/2002 | |
| WO | WO 02/088181 A2 | | 11/2002 | |
| WO | WO 02/092004 A2 | | 11/2002 | |
| WO | WO 03/043651 A1 | | 5/2003 | |
| WO | WO 2004/004763 A2 | | 1/2004 | |
| WO | WO 2004/004770 A1 | | 1/2004 | |
| WO | WO 2004/044001 A2 | | 5/2004 | |
| WO | WO 2004/046345 A2 | | 6/2004 | |
| WO | WO 2004/061456 A2 | | 7/2004 | |
| WO | WO 2005/025604 A2 | | 3/2005 | |
| WO | WO 2005/074984 A1 | | 8/2005 | |
| WO | WO 2006/008779 | | 1/2006 | |
| WO | WO 2006/010628 A1 | | 2/2006 | |
| WO | WO 2006/024547 A2 | | 3/2006 | |
| WO | WO 2006/047820 A1 | | 5/2006 | |
| WO | WO 2006/077614 A1 | | 7/2006 | |
| WO | WO 2006/080434 A1 | | 8/2006 | |
| WO | WO 2006/100651 A1 | | 9/2006 | |
| WO | WO 2006/114805 A2 | | 11/2006 | |
| WO | WO 2007/015546 A1 | | 2/2007 | |
| WO | WO 2007/031100 A1 | | 3/2007 | |
| WO | 2007061762 A2 | | 5/2007 | |
| WO | 2007076290 A2 | | 7/2007 | |
| WO | WO 2007-130725 A | | 11/2007 | |
| WO | WO 2008/018641 A1 | | 2/2008 | |
| WO | 2008031612 A1 | | 3/2008 | |
| WO | WO 2008/053892 A1 | | 5/2008 | |
| WO | 2008155659 A2 | | 12/2008 | |
| WO | WO 2009/133939 | | 11/2009 | |
| WO | WO 2009/133940 | | 11/2009 | |
| WO | WO 2009/133943 | | 11/2009 | |
| WO | WO 2011/046570 | | 4/2011 | |
| WO | WO 2012/147470 A1 | | 11/2012 | |
| WO | WO 2014/065347 A1 | | 5/2014 | |
| WO | 2014191364 A1 | | 12/2014 | |
| WO | 2016184795 A1 | | 11/2016 | |
| WO | 2018139562 A1 | | 8/2018 | |
| WO | 2019107530 A1 | | 6/2019 | |
| WO | 2019156137 A1 | | 8/2019 | |
| WO | 2020071519 A1 | | 4/2020 | |
| WO | 2020071520 A1 | | 4/2020 | |

OTHER PUBLICATIONS

Thorey, I. et al. "The $Ca^{2+}$-binding Proteins S100A8 and S100A9 are Encoded by Novel Injury-regulated Genes", *The Journal of Biological Chemistry*, Sep. 21, 2001, vol. 276, No. 38, pp. 35818-35825. (Epub Jul. 19, 2001).

Hiratsuka, Sachie et al. "Tumour-mediated upregulation of chemoattractants and recruitment of myeloid cells predetermines lung metastasis," *Nature Cell Biology*, Dec. 2006; Epub Nov. 26, 2006; vol. 8 No. 12, pp. 1369-1375, Supplemental 1-7, Dec. 2006; Epub Nov. 26, 2006 (Nature Publishing Group).

Kassis, I. et al., "Isolation of mesenchymal stem cells from G-CSF-mobilized human peripheral blood using fibrin microbeads", *Bone Marrow Transplantation*, May 2006, vol. 37, No. 10, pp. 967-976.

Lin, Siang-Yo et al., "The isolation of novel mesenchymal stromal cell chemotactic factors from the conditioned medium of tumor cells", *Experimental Cell Research*, 2008, vol. 314, No. 17, pp. 3107-3117.

Ozaki, Yoshie et al., "Comprehensive Analysis of Chemotactic Factors for Bone Marrow Mesenchymal Stem Cells", *Stem Cells and Development*, Feb. 2007, vol. 16, No. 1, pp. 119-129.

Palumbo, Roberta et al., "Cells migrating to sites of tissue damage in response to the danger signal HMGB1 require NF-κB activation", *The Journal of Cell Biology*, Oct. 8, 2007, vol. 179, No. 1, pp. 33-40.

Sasaki, Mikako et al., "Mesenchymal Stem Cells Are Recruited into Wounded Skin and Contribute to Wound Repair by Transdifferentiation into Multiple Skin Cell Type[1]", *The Journal of Immunology*, Feb. 15, 2008, vol. 180, No. 4, pp. 2581-2587.

Heil, Matthias et al., "An engineered heparin-binding form of VEGF-E (hbVEGF-E): Biological effects in vitro and mobilization of precursor cells", *Angiogenesis*, 2003, vol. 6, No. 3, pp. 201-211.

Meng, Erhong et al., "High Mobility Group Box 1 Protein Inhibits the Proliferation of Human Mesenchymal Stem Cell and Promotes Their Migration and Differentiation along Osteoblastic Pathway", *Stem Cells and Development*, 2008, vol. 17, No. 4, pp. 805-814.

Pusterla, Tobias et al., "High mobility group B2 is secreted by myeloid cells and has mitogenic and chemoattractant activities similar to high mobility group B1", *Autoimmunity*, Apr. 2009, vol. 42, No. 4, pp. 308-310.

Uchida et al."The chemotactic activity of PDGF-bb, BMP-2, and FGF-2 towards committed and uncommitted mesenchymal stem cells", *The Journal of Japanese Orthopaedic Surgical Society*, 2005, vol. 79, No. 8, S832, 1-P6-6.

Vandal, Karen et al. "Blockade of S100A8 and S100A9 Suppresses Neutrophil Migration in Response to Lipopolysaccharide", *The Journal of Immunology*, Sep. 1, 2003, vol. 171, No. 5, pp. 2602-2609.

(56) References Cited

OTHER PUBLICATIONS

Wang, Huan Liang et al. "High mobility group protein B1 and the research progress of its biological effect", *Journal of Chinese Modern Surgery*, Dec. 31, 2006, vol. 3, No. 22, pp. 1806-1809.

Alden et al., "In Vivo Endochondral Bone Formation Using a Bone Morphogenetic Protein 2 Adenoviral Vector", *Human Gene Therapy*, 1999, vol. 10, No. 13, pp. 2245-2253.

Bittira et al., "Mobilization and homing of bone marrow stromal cells in myocardial infarction", *European Journal of Cardiothoracic Surgery*, Sep. 2003, vol. 24, No. 3, pp. 393-398.

Bustin, "Regulation of DNA-Dependent Activities by the Functional Motifs of the High-Mobility-Group Chromosomal Proteins", *Molecular and Cellular Biology*, 1999, vol. 19, No. 8, pp. 5237-5246.

Charoonpatrapong et al., "HMGB1 Expression and Release by Bone Cells", *Journal of Cellular Physiology*, 2006, vol. 207, No. 2, pp. 480-490.

Chou et al., "Identity of nuclear high-mobility-group protein, HMG-1, and sulfoglucuronyl carbohydrate-binding protein, SPB-1, in brain", *Journal of Neurochemistry*, 2001, vol. 77, No. 1, pp. 120-131.

Degryse et al., "The High Mobility Group (HMG) Boxes of the Nuclear Protein HMG1 Induce Chemotaxis and Cytoskeleton Reorganization in Rat Smooth Muscle Cells", *The Journal of Cell Biology*, 2001, vol. 152, No. 6, pp. 1197-1206.

Delarosa et al., "Modulation of Adult Mesenchymal Stem Cells Activity by Toll-Like Receptors: Implications on Therapeutic Potential", *Mediators of Inflammation*, 2010, vol. 2010, Article ID: 865601, pp. 1-9.

Eckert et al., "S100 Proteins in the Epidermis", *The Journal of Investigative Dermatology*, 2004, vol. 123, No. 1, pp. 23-33.

Fujii et al., "Roles of Bone Morphogenetic Protein Type I Receptors and Smad Proteins in Osteoblast and Chondroblast Differentiation", Molecular Biology of the Cell, 1999, vol. 10, No. 11, pp. 3801-3813.

Germani et al., "Pivotal Advance: High-Mobility group box 1 protein—a cytokine with a role in cardiac repair", *Journal of Leukocyte Biology*, 2007, vol. 81, No. 1, pp. 41-45.

Granero-Molto et al., "Role of mesenchymal stem cells in regenerative medicine: application to bone and cartilage repair", *Expert Opinion on Biological Therapy*, 2008, vol. 8, No. 3, pp. 255-268.

Harris et al., "The nuclear protein HMGB1 as a proinflammatory mediator", *European Journal of Immunology*, 2004, vol. 34, No. 6, pp. 1503-1512.

Harris et al., "Alarmin(g) news about danger", *EMBO reports*, 2006, vol. 7, No. 8, pp. 774-778.

Hori et al., "The Receptor for Advanced Glycation End Products (RAGE) Is a Cellular Binding Site for Amphoterin", *The Journal of Biological Chemistry*, 1995, vol. 270, No. 43, pp. 25752-25761.

Jansen et al., "Transplantation of hematopoietic stem cells from the peripheral blood", *Journal of Cellular and Molecular Medicine*, 2005, vol. 9, No. 1, pp. 37-50.

Jayaraman et al., "High mobility group protein-1 (HMG-1) is a unique activator of p53", *Genes & Development*, 1998, Vo. 12, No. 4, pp. 462-472.

Jiang et al., "Pluripotency of mesenchymal stem cells derived from adult marrow", *Nature*, 2002, vol. 418, No. 6893, pp. 41-49.

Laflamme et al. "Regenerating the heart", Nature Biotechnology, Jul. 2005, vol. 23, No. 7, pp. 845-856.

Limana et al., "Exogenous High-Mobility Group Box 1 Protein Induces Myocardial Regeneration After Infarction via Enhanced Cardiac C-Kit * Cell Proliferation and Differentiation", *Circulation Research*, 2005, Vo. 97, No. 8, pp. e73-e83.

Liotta et al., "Toll-Like Receptors 3 and 4 Are Expressed by Human Bone Marrow-Derived Mesenchymal Stem Cells and Can Inhibit Their T-Cell Modulatory Activity by Impairing Notch Signaling", *Stem Cells*, 2008, vol. 26, No. 1, pp. 279-289.

Maruyama, "Inflammation and HMGB1/RAGE system", *Kekkan Igaku*, 2005, vol. 6, No. 5, pp. 519-525. See English translation.

Meng et al., "HMGB1 induces migration of human bone marrow-derived mesenchymal stem cells", *Bull Acad. Mil. Med. Sci.*, 2006, vol. 30, No. 3, pp. 213-216. See English Translation.

Merenmies et al., "30-kDa Heparin-binding Protein of Brain (Amphoterin) Involved in Neurite Outgrowth", The Journal of Biological Chemistry, 1991, vol. 266, No. 25, p. 16722-16729.

Mistry, A.R. et al. "Recombinant HMG1 Protein Produced in Pichia Pastoris: A Nonviral Gene Delivery Agent" BioTechniques, 1997, vol. 22, pp. 718-729.

Muhammad, Sajjad, et al. "The HMGBI Receptor Rage Mediates Ischemic Brain Damage," *The Journal of Neuroscience*, Nov. 12, 2008, vol. 28, No. 46, pp. 12023-12031.

Müller et al., "The double life of HMGB-1 chromatin protein: architectural factor and extracellular signal", *The EMBO Journal*, 2001, vol. 20, No. 16, pp. 4337-4340.

Nakamura et al., "p38 Mitogen-Activated Protein Kinase Functionally Contributes to Chondrogenesis Induced by Growth/Differentiation Factor-5 in ATDC5 Cells", *Experimental Cell Research*, 1999, vol. 250, No. 2, pp. 351-363.

Opitz et al., "Toll-like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R", *Stem Cells*, 2009, vol. 27, No. 4, pp. 909-919.

Otsuru et al., "BMP-2 mobilizes robust bone marrow mesenchymal progenitor cells to the circulating blood in bone regeneration", *The 28th Annual Meeting of the Molecular Biology Society of Japan*, , Nov. 25, 2005, 733(3P-1012). See English Translation.

Palumbo et al., "Extracellular HMGB1, a signal of tissue damage, induces mesoangioblast migration and proliferation", *The Journal of Cell Biology*, 2004, vol. 164, No. 3, pp. 441-449.

Palumbo et al., "High mobility group box 1 protein, a cue for stem cell recruitment", *Biochemical Pharmacology*, 2004, vol. 68, No. 6, pp. 1165-1170.

Pevsner-Fischer et al., "Toll-like receptors and their ligands control mesenchymal stem cell functions", *Blood*, 2007, vol. 109, No. 4, pp. 1422-1432.

"Principles and Protocols of Tissue Engineering," Jun. 2004, pp. 277-278.

Raicevic et al., "Inflammation modifies the pattern and the function of Toll-like receptors expressed by human mesenchymal stromal cells", *Human Immunology*, 2010, vol. 71, No. 3, pp. 235-244.

Robinson et al., "TheSlOO Family Heterodimer, MRP-8/14, Binds with High Affinity to Heparin and Heparan Sulfate Glycosaminoglycans on Endothelial Cells", *The Journal of Biological Chemistry*, 2002, vol. 277, No. 5, pp. 3658-3665.

Ryckman et al., "Proinflammatory Activities of S100: Proteins S100A8, S100A9, and S100A8/A9 Induce Neutrophil Chemotaxis and Adhesion", *The Journal of Immunology*, 2003, vol. 170, No. 6, pp. 3233-3242.

Schäffer et al., "Wound Fluid Inhibits Wound Fibroblast Nitric Oxide Synthesis", *Journal of Surgical Research*, 2004, vol. 122, No. 1, pp. 43-48.

Shibata et al., "Fibroblast growth-stimulating activity of S100A9 (MRP-14)", *European Journal of Biochemistry*, 2004, vol. 271, No. 11, pp. 2137-2143.

Shing et al., "Heparin Affinity: Purification of a Tumor-Derived Capillary Endothelial Cell Growth Factor", *Science*, Mar. 23, 1984, vol. 223, No. 4642, pp. 1296-1299.

Sun et al., "Isolation of Mouse Marrow Mesenchymal Progenitors by a Novel and Reliable Method", *Stem Cells*, 2003, vol. 21, No. 5, pp. 527-535.

Tagami et al., "Elevation of serum high-mobility group box 1 protein during granulocyte colony-stimulating factor-induced peripheral blood stem cell mobilisation", *British Journal of Haematology*, 2006, vol. 135, No. 4, pp. 567-569.

Tamai et al., "New Wave of Wound Healing", *Japanese Journal of Dermatology*, 2008, vol. 118, No. 4, pp. 645, #EL28-4. See English translation.

Tamai et al., U.S. Appl. No. 11/997,475, "Mesenchymal Stem Cell Inducer, Tissue Regeneration Promoter and Method of Preparing Mesenchymal Stem Cell", filed Jan. 31, 2008, Now Abandoned.

(56) References Cited

OTHER PUBLICATIONS

Telusma et al., "Dendritic cell activating peptides induce distinct cytokine profiles", International Immunology, Nov. 2006, vol. 18, No. 11, pp. 1563-1573.
Wang et al., "HMG-1 as a Late Mediator of Endotoxin Lethality in Mice", Science, 1999, vol. 285, No. 5425, pp. 248-251.
Wu et al., "Mesenchymal Stem Cells Enhance Wound Healing Through Differentiation and Agiogenesis", Stem Cells, 2007, vol. 25, No. 10, pp. 2648-2659.
Instruction Manual of HiTrap chelating HP (Amersham Biosciences), 2003, pp. 1-6.
Lonza BenchGuides, "Poietics Human Mesenchymal Stem Cells and Media hMSC", 2008, (Document # TS-PT-212-7 04/08).
Wang, Huating et al., "Theories and Technologies for Stem Cells," Science Press, Mar. 2005, vol. 5, p. 58-61.
Tamai et al. U.S. Appl. No. 14/114,395, "Peptide for Inducing Regeneration of Tissue and Uses Thereof," filed Oct. 28, 2013, assigned to Genomix Co. Ltd. and Osaka University.
Li, S. and Huang, L. "Millennium Review, Nonviral gene therapy: promises and challenges" Gene Ther. 7:31-34, 2000, Macmillan Publishers Ltd.
Somia, Nikunj and Verma, Inder M. "Reviews, Gene Therapy: Trials and Tribulations" Nat. Rev. Genet. 1(2):91-99, Nov. 2000), Macmillan Publishers Ltd.
Chen, Xiaoguang et al. "Human Bone Marrow Stromal Cell Cultures Conditioned by Traumatic Brain Tissue Extracts: Growth Factor Production," Journal of Neuroscience Research, 2002, 69:687-691.
Forte, Giancarlo et al. "Hepatocyte Growth Factor Effects on Mesenchymal Stem Cells: Proliferation, Migration, and Differentiation," Stem Cells, 2006, 24:23-33.
Huttunen, Henri J. et al. "Receptor for Advanced Glycation End Products-binding COOH-terminal Motif of Amphoterin Inhibits Invasive Migration and Metastasis," Cancer Research, 2002, 62:4805-4811.
La Rosa, Tj et al. "Glycine max protein Seq ID No. 211221," Geneseq Accession No. AFQ20044, 2007.
Liu, Ke-Xin et al. "Human Placental Extract Stimulates Liver Regeneration in Rats," Biological and Pharmaceutical Bulletin, 1998, 21(1):44-49.
Mori, Taisuke et al. "Stem Cells/ ES cells—Mesenchymal Stem Cells—Human Bone Marrow Derived Mesenchymal Stem Cells," Saisei Iryou - Regenerative Medicine, 2005, 4(3); 421-9, 351.
Takami, Yoichiro et al. "Synergistic Induction of Hepatocyte Growth Factor in Human Skin Fibroblasts by the Inflammatory Cytokines Interleukin-1 and Interferon-γ," Biochemical and Biophysical Research Communications, 2005, 327:212-217.
Tamai, Katsuto et al., "PDGFRα-positive cells in bone marrow are mobilized by high mobility group box 1 (HMGB1) to regenerate injured epithelia," http://www.pnas.org/content/early/2011/03/30/1016753108.full.pdf+html, http://www.pnas.org/content/early/2011/03/30/1016753108/suppl/DCSupplemental, http://www.pnas.org/content/suppl/2011/03/31/1016753108.DCSupplemental/pnas.201016753SI.pdf, http://www.pnas.org/content/early/2011/03/30/1016753108.abstract, http://www.pnas.org/content/early/2011/03/30/1016753108.full.pdf.
Tamai, Katsuto et al., "PDGFRα-positive cells in bone marrow are mobilized by high mobility group box 1 (HMGB1) to regenerate injured epithelia," http://www.pnas.org/content/108/16/6609.full.pdf+html, http://www.pnas.org/content/108/16/6609/suppl/DCSupplemental, http://www.pnas.org/content/suppl/2011/03/31/1016753108.DCSupplemental/pnas.201016753SI.pdf, http://www.pnas.org/content/108/16/6609.abstract, http://www.pnas.org/content/108/16/6609.figures-only, http://www.pnas.org/content/108/16/6609.full.pdf, http://www.pnas.org/content/108/16/6609.full.
Tatsumi, Ryuichi et al. HGF/SF Is Present in Normal Adult Skeletal Muscle and is Capable of Activating Satellite Cells, 1998, Developmental Biology, 194:114-128.

Yuan, Yan et al. "Differentiation of Mesenchymal Stem Cells in Induction of Myocardial Cell Lysate," Chinese Journal of Cardiology, 2005, 33(2):170-173.
Castro, Raymond F et al. "Failure of Bone Marrow Cells to Transdifferentiate into Neural Cells in Vivo," Science, Aug. 2002, 297(5585): 1299.
Chen Y. et al. "Coaxing Bone Marrow Stromal Mesenchymal Stem Cells Towards Neuronal Differentiation: Progress and Uncertainties," Cellular Molecular Life Science, Jul. 2006, 63(14): 1649-1657.
Chopp, Michael et al. "Treatment of Neural Injury with Marrow Stromal Cells," The Lancet Neurology, Jun. 2002, 1(2):92-100.
Gueukdjian, S.A. "Intra-Arterial Injections in the Treatment of Peripheral Vascular Disease," Postgrad Medical Journal, Jan. 1955, 31(351): 30-31.
Institutional Animal Care and Use Committee (IACUC), "Blood Collection: The Mouse." May 2014, University of California, San Francisco. Taken from web: iacuc.usfc.edu/Policies/BloodCollectionMice.doc.
Kern, Susanne et al., "Comparative Analysis of Mesenchymal Stem Cells from Bone Marrow, Umbilical Cord Blood, or Adipose Tissue," Stem Cells, 2006, 24(5): 1294-1301. Epub Jan. 12, 2006.
Paul, S.R. et al., "Stromal Cell-Associated Hematopoiesis: Immortalization and Characterization of a Primate Bone Marrow-Derived Stromal Cell Line," Blood, 1991, 77(8):1723-33.
Schön et al. "Psoriasis," The New England Journal of Medicine, May 2005, 352(18): 1899-1912.
Tagliafico, Enrico et al., "TGFβ/BMP activate the smooth muscle/bone differentiation programs in mesoangioblasts," Journal of Cell Science, 2004, 117(19):4377-88.
Tamai, Katsuto et al. "PDGFRα-positive cells in bone marrow are mobilized by high mobility group box 1 (HMGB1) to regenerate inured epithelia," Proceedings of the National Academy of Sciences, 2011, 108(16): 6609-6614.
Yang, De et al., "High mobility group box-1 protein induces the migration and activation of human dendritic cells and acts as an alarmin," Journal of Leukocyte Biology., Jan. 2007, 81(1):59-66. Epub Sep. 11, 2006.
Youn, Ju Ho et al., "High Mobility Group Box 1 Protein Binding to Lipopolysaccharide Facilitates Transfer of Lipopolysaccharide to CD14 and Enhances Lipopolysaccharide-Mediated TNF-α Production in Human Monocytes," The Journal Immunology., Apr. 2008, 180(7):5067-74.
Gudjonsson, Johann E. et al. "Psoriasis," Fitzpatrick's Dermatology in General Medicine, 8th edition, New York: Mc-Graw Hill Medical, 2012, p. 197-217.
Koc, On et al. "Mesenchymal Stem Cells: Heading into the Clinic," Bone Marrow Transplantation, 2001, vol. 27, No. 3, pp. 235-239.
Pittenger, Mark F. et al. "Multilineage Potential of Adult Human Mesenchymal Stem Cells," Science, 1999, vol. 284, No. 5411, pp. 143-147.
Wexler, Sarah A. et al. "Adult Bone Marrow is a Rich Source of Human Mesenchymal 'Stem' Cells but Umbilical Cord and Mobilized Adult Blood Are Not," British Journal of Haematology, 2003, vol. 121, No. 2, pp. 368-374.
Matsumoto, Kunio et al., "Up-Regulation of Hepatocyte Growth Factor Gene Expression by Interleukin-1 in Human Skin Fibrosis," Biochemical and Biophysical Research Communications, 1992, 188(1):235-243.
Popovic, Karin et al., "Increased Expression of the Novel Proinflammatory Cytokine High Mobility Group Box Chromosomal Protein 1 in Skin Lesions of Patients With Lupus Erythematosus," Arthritis & Rheumatism, 2005, 52(11):3639-3645.
Tamai, Katsuto et al. U.S. Appl. No. 14/436,906, "Novel Method for Treating Cardiac Infarction Using HMGBI Fragment," filed Apr. 20, 2015, and assigned to Genomix Co., Ltd. and Osaka University.
Tamai, Katsuto et al. U.S. Appl. No. 14/436,920, "Novel Method for Treating Spinal Cord Injury Using HMGB1 Fragment," filed Apr. 20, 2015, assigned to Genomix Co., Ltd. and Osaka University.
Li, Zihai et al., "Heat-Shock Proteins," Current Protocols in Immunology, 2003, Supplement 58, A.IT.1-A.IT.6.

(56) References Cited

OTHER PUBLICATIONS

Martin-Murphy, Brittany V. et al., "The Role of Damage Associated Molecular Pattern Molecules in Acetaminophen-Induced Liver Injury in Mice," *Toxicol Lett,* Feb. 2010, 192(3):1-20.
Panepucci, Rodrigo A. et al., "Abstract# 4427: Comparison of Gene Expression of Mesenchymal Stem Cells from the Umbilical Cord and from the Bone Marrow," *Blood,* Nov. 2003, 16(102):Abstract.
Pankov, Roumen et al., "Fibronectin at a glance," *J Cell Sci,* Oct. 2002, 115(20):3861-3863.
Santamaria-Kisiel, Liliana et al., "Calcium-dependent and -independent interactions of the S100 protein family," *Biochem J.,* 2006, 396:201-214.
Seong, Yong Seong et al., "Hydrophobicity: an ancient damage-associated molecular pattern that initiates innate immune responses," Nature Reviews: *Immunology,* Jun. 2004, 4(6):469-78.
Soo, Eliza T. L. et al., "Heat Shock Proteins as Novel Therapeutic Targets in Cancer," *in vivo,* 2008, 22(3):311-5.
Wang, Lei et al., "Ischemic cerebral tissue and MCP-1 enhance rat bone marrow stromal cell migration in interface culture," *Experimental Hematology,* 2002, 30:831-836.
Yamada, Takayuki et al., "Regulation of osteoclast development by Notch signaling directed to osteoclast precursors and through stromal cells," *Blood,* Mar. 2003, 101(6):2227-2234.
Bianchi, Marco E. et al., "The DNA binding site of HMG1 protein is composed of two similar segments (HMG boxes), both of which have counterparts in other eukaryotic regulatory proteins," *The EMBO Journal,* Mar. 1992, 11(3):1055-1063.
Gong, Wei et al., "The Anti-Inflammatory Activity of HMGB1 A Box is Enhanced When Fused with C-Terminal Acidic Tail," *Journal of Biomedicine and Biotechnology,* vol. 2010, Article ID 915234, 6 pages, 2-10. Doi:10.1155/2010/915234.
Chamberlain, Giselle et al., "Concise Review: Mesenchymal Stem Cells: Their Phenotype, Differentiation Capacity, Immunological Features, and Potential for Homing," *Stem Cells* 2007; 25:2739-2749.
Kessler, Michael W. et al., "Tissue Engineering and Cartilage," *Organogenesis,* Jan. 2008; 4(1):28-32.
Lanza, Robert et al., and Arnold Caplan, "Essentials of Stem Cell Biology—Chapter 27, Mesenchymal Stem Cells," *Elsevier Academic Press,* 2006, pp. 205-210.
De Souza, A.W.S et al., "HMGB1 in Vascular Diseases: Its Role In Vascular Inflammation And Atherosclerosis," *Autoimmunity Reviews,* 2012, 11:909-917.
Zhou, Xiaoya et al., "Exogenous High-Mobility Group Box 1 Protein Injection Improves Cardiac Function after Myocardial Infarction: Involvement of Wnt Signaling Activation," *Journal of Biomedicine and Biotechnology,* 2012, vol. 2012, pp. 1-5.
Cole, John Sterling, "Pharmacologic Mobilization of Mesenchymal Stem Cells for Enhanced Bone Formation," *Colby College, Rush University,* 2009; UMI No. 1466383, pp. 1-82.
Kirov, Sergei A. et al., "In Vivo 2-Photon Microscopy Reveals G-CSF Enhanced Mobilization and Targeting of Neo-Endogenous Bone Marrow Stromal Cells to Stroke Injury Sites," *Stroke,* Apr. 2009, 40(4):1-2, e133, Abstract No. 107.
Straino, Stefania et al., "High-Mobility Group Box 1 Protein in Human and Murine Skin: Involvement in Wound Healing," *Journal of Investigative Dermatology,* 2008, 128:1545-1553.
Dong, Yingying et al., "HMGB1 Protein Does Not Mediate the Inflammatory Response in Spontaneous Spinal Cord Regeneration," The Journal of Biological Chemistry, Jun. 21, 2013, 288(25):18204-18218.
Kikuchi, Kiyoshi et al., "HMGB1 as a therapeutic target in spinal cord injury: A hypothesis for novel therapy development (Review)," *Experimental and Therapeutic Medicine,* 2011, 2:767-770.
Ulloa, Luis et al., "High-mobility group box 1 (HMGB1) protein: Friend and foe," *Cytokine & Growth Factor Reviews,* 2006, 17:189-201.
Venereau, Emilie et al., "Mutually exclusive redox forms of HMGB1 promote cell recruitment of proinflammatory cytokine release," *J. Exp. Med.,* 2012, 209(9):1519-1528.

Basso, D. Michelle et al., "Basso Mouse Scale for Locomotion Detects Differences in Recovery after Spinal Cord Injury in Five Common Mouse Strains," *Journal of Neurotrauma,* 2006, 23(5):635-659.
Fang, Ping et al., "HMGB1 Contributes to Regeneration After Spinal Cord Injury in Adult Zebrafish," *Mol Neurobiol,* 2014, 49:472-483.
Kitahara, Tatsuro et al., "High-Mobility Group Box 1 Restores Cardiac Function After Myocardial Infarcation in Transgenic Mice", *Cardiovascular Research, European Society of Cardiology,* Oct. 1, 2008, 80:40-46.
Kohno, Takashi et al., "High Mobility Group Box 1 Protein is Associated With Post-Infarction Healing Process and Left Ventricular Remodeling", *Circ. J.,* 2008, 72 Supplement 1, PJ-004:510-511.
Nakajima et al., "Dynamics and Role of High Mobility Group Box-1 (HMGB-1) in Injured Spinal Cord," *Nihon Seikei Geka Gakkai Zasshi (J. Jpn. Orthop. Assoc.),* 2010, 84(8):S1050.
Quertainmont, Renaud et al., "Mesenchymal Stem Cell Graft Improves Recovery after Spinal Cord Injury in Adult Rats through Neurotrophic and Pro-Angiogenic Actions," *PLoS ONE,* Jun. 2012, 7(6):1-15.
Rahimi-Movaghar, Vafa, "Effect of Decompression on Complete Spinal Cord Injury in Rats," International Journal of Neuroscience, 2008, 118:1359-1373.
Takahashi, Kunihiko et al., "Effects of HMGB1 on PostInfarction Chronic Heart Failure—Novel Mechanism Regarding Therapeutic Effects of Cell Therapy", Supplement, 2011,27 I-E-19:S189.
Takeishi, Yasuchika et al., "Importance of Inflammation and Immune Response in Heart Failure—Toll-Like Receptor-Mediated Signaling Pathway and Ventricular Remodeling After Myocardial Infarction", *Journal of Clinical and Experimental Medicine,* Jan. 30, 2010, 232(5):378-385.
Tamai, Katsuto et al., "Development and Outlook of Internal Regeneration-Inducing Pharmaceuticals that use in vivo Bone Marrow Mesenchymal Stem / Progenitor Cell-Mobilizing Factors", *Gene & Medicine MOOK,* Jul. 22, 2012, pp. 207-212.
Bianchi, M.E., "High mobility group 1 protein (HMGB1) N-terminal peptide." Geneseq Accession No. ADG80180, Aug. 12, 2004.
Esposito, E., et al., "Melatonin reduces stress-activated/mitogen-activated protein kinases in spinal cord injury." *J. Pineal Res.,* 2009, 46: 79-86.
Healthwise Staff, "Age-related Macular Degeneration." *University of Michigan Health System,* Aug. 2015, https://www.uofmhealth.org/health-library/hw176039.
Herrera, M.B., et al., "Exogenous mesenchymal stem cells localize to the kidney by means of CD44 following acute tubular injury," *Kidney International,* 2007; 72:430-441.
Jiao, C., et al., "Researchers find nerve damage may precede diabetic retinopathy." *EurekAlert? Science News,* Apr. 2016, https://www.eurekalert.org/pub_releases/2016-04/uoih-rfv042616.php.
Kawabata, H., et al., "High Mobility Group Box 1 Is Upregulated After Spinal Cord Injury and Is Associated With Neuronal Cell Apoptosis." *Spine,* 2010, 35(11): 1109-1115.
Morosetti, R., et al., "MyoD expression restores defective myogenic differentiation of human mesoangioblasts from inclusion-body myositis muscle." *PNAS,* Nov. 7, 2006, 103(45): 16995-17000.
Slater, M., et al., "Endometriotic cells exhibit metaplastic change and oxidative DNA damage as well as decreased function, compared to normal endometrium." *Journal of Molecular Histology,* 2005, 36(4): 257-263.
Tang, Daolin, et al., "High-Mobility Group Box 1, Oxidative Stress, and Disease," Antioxidants & Redox Signaling, 2011; 14(7): 1315-1335. DOI: 10.1089/ars.2010.3356.
Wolf, G., et al., "From the Periphery of the Glomerular Capillary Wall Toward the Center of Disease." *Diabetes,* Jun. 2005, 54(6): 1626-1634.
Woodbury, Dale et al., "Adult Rat and Human Bone Marrow Stromal Cells Differentiate Into Neurons," *Journal of Neuroscience Research,* Aug. 15, 2000; 61(4):364-370.
Arminan, Ana et al., "Mesenchymal Stem Cells Provide Better Results Than Hematopoietic Precursors for the Treatment of Myocardial Infarction." *JACC,* May 18, 2010, 55(20): 2244-2253.

(56) References Cited

OTHER PUBLICATIONS

Berry, Mark F., et al., "Mesenchymal stem cell injection after myocardial infarction improves myocardial compliance." *Am J Physiol Heart Circ Physiol*, Jun. 2006, 290(6): H2196-H2203.

HMGbiotech, "BoxA from HMGB1, human & mouse, LPS-free." *HMGBiotech Srl*, 2008, C.F. e P.IVA 04942740962, http://www.hmgbiotech.com/products.php?ID=91.

HMGbiotech, "BoxA from HMGB1, human & mouse LPS-free—Datasheet." *HMGBiotech Srl*, 2008, Via Moretto da Brescia 25, 20133—Milano, Italy, http://www.hmgbiotech.com/upload/documenti/0515122144_boxa.

Ishikane, Shin, "Therapeutic application of allogenic fetal membrane-derived mesenchymal stem cells transplantation in regenerative medicine." Pharmaceutical Bulletin of Fukuoka University, Mar. 2011, 11(0): 17-25.

Li, Ying et al., "Advancement of Human Multiply, Sex health and Reproductive Medical Science." *Peking University Medical Press*, Mar. 2007, $1^{st}$ Edition, 270-271.

Takahashi, Kunihiko, et al., "Modulated Inflammation by Injection of High-Mobility Group Box 1 Recovers Post-Infarction Chronically Failing Heart." *Circulation*, Sep. 2008, 118(14 Suppl): S106-S114.

Wang, Wei et al., "Intravenous administration of bone marrow mesenchymal stromal cells is safe for the lung in a chronic myocardial infarction model." *Regen Med*, Mar. 2011,6(2): 179-190.

Wang, Yaping, "Biology of hematopoietic stem cell and the research method thereof." Science Press, Mar. 2007, 1st Edition, 56-58.

Chen, T., et al., "Involvement of high mobility group box-1 in imiquimod-induced psoriasis-like mice model" Journal of Dermatology, 2017, 44: 573-581.

Goto, et al., "Investigation of the application of myocardial regeneration inducing therapy using HMGB1 to cardiac infarction." Regenerative Medicine, Feb. 1, 2017, 16: 289.

Ishikane, Shin, et al., "Development of multi-growth factor secreted fetal membrane-derived mesenchymal stem cell sheets." Grants-in-Aid for Scientific Research, 2014, pp. 1-6.

Kikuchi, et al., "Systemic administration of HMGB1 improves bleomycin-induced skin fibrosis by locally accumulating bone marrow mesenchymal stem cells." Regenerative Medicine, Feb. 1, 2017,16:422.

Komurasaki, et al., "HMGB1 ameliorates bleomycin-induced skin fibrosis by promoting accumulation of mesenchymal stem cells to the lesion." The 48th Annual Meeting of The Japanese Society of Matrix Biology and Medicine, 2016, p. 78.

Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science ), 2015, 33(2): 126-127. http://www.lib.yamagata-u.ac.jp/alllib/elib/kiyou/kiyoum/kiyoum-33-2/image/kiyoum-33-2-125to131.pdf.

Panepucci, R. A. et al., "Comparison of Gene Expression of Umbilical Cord Vein and Bone Marrow-Derived Mesenchymal Stem Cells." Stem Cells, Dec. 2004, 22 (7): 1263-1278.

Saver, J.L., "Time Is Brain-Quantified." Stroke, 2006, 37: 263-266.

Tamai, K., "Development of regeneration-inducing medicine utilizing the in vivo injured tissue regeneration mechanism of peripheral circulating mesenchymal cells." BIO Clinica, Sep. 10, 2016, 31(10): 1042-1046.

Tamai, et al., "Tissue repair mechanism by bone-marrow-derived stem cells." Experimental Mediciner, 2013, 31(5) 655-661.

Wang, F.-C., et al., "Overexpression of HMGB1 A-box reduced lipopolysaccharide-induced intestinal inflammation via HMGB1/TLR4 signaling in vitro." World J Gastroenterol, Jul. 7, 2015, 21(25): 7764-7776.

Yamaoka, S., et al., "1043 Systemic delivery of HMGB1 peptide ameliorates imiquimod-induced psoriasis-like dermatitis." Journal of Investigative Dermatology, 2018, 138(5): S177.

Kang, H., et al., "Reversing established sepsis with antagonists of endogenous high-mobility group box 1." Proceedings of the National Academy of Sciences, 2004, 101(1): 296-301.

Zheng, X., et al., "Adeno-associated virus-mediated colonic secretory expression of HMGB1 A box attenuates experimental colitis in mice." J Gene Med, 2016, 18(10): 261-272.

Brunner, S., et al., "Erythropoientin Administration After Myocardial Infarction in Mice Attenuates Ischemic Cardiomyopathy Associated with Enhanced Homing of Bone Marrow-Derived Progenitor Cells Via the CXCR-4/SDF-1 Axis." The FASEB Journal, 2009, 23: 351-361.

"Cardiomegaly" Merriam Webster, 2015 archived page, accessed via Wayback Machine [online] [accessed at https://web.archive.org/web/20150107154504/https://www.merriam-webster.com/medical/cardiomegaly on May 21, 2020]. (Year 2015).

Fritsch, A., et al., "A Hypomorphic Mouse Model of Dystrophic Epidermolysis Bullosa Reveals Mechanisms of Disease and Response to Fibroblast Therapy." The Journal of Clinical Investigation, 2008, 118(5): 1669-1679.

Fukushima, N., et al., "Registry Report on Heart Transplantation in Japan (Jun. 2016)." Circulation Journal, 2016 CJ-16.

Guillot, L., et al., "Response of Human Pulmonary Epithelial Cells to Lipopolysaccharide Involves Toll-like Receptor 4 (TLR4)-dependent Signaling Pathways." Journal of Biological Chemistry, 2004, 279(4): 2712-2718.

Guo, J., et al., "Monocyte Chemotactic Protein-1 Promotes the Myocardial Homing of Mesenchymal Stem Cells in Dilated Cardiomyopathy." International Journal of Molecular Sciences, 2013, 14: 8164-8178.

Hornef, M., et al., "Toll-Like Receptor 4 Resides in the Golgi Apparatus and Colocalizes with Internalized Lipopolysaccharide in Intestinal Epithelial Cells." The Journal of Experimental Medicine, 2002, 195(5): 559-570.

Kokkola, R., et al., "RAGE is the Major Receptor for the Proinflammatory Activity of HMGB1 in Rodent Macrophages." Scandinavian Journal of Immunology, 2005, 61:1-9.

Komurasaki, Y., et al., "555 Systemic HMGB1 Administration Ameliorated Bleomycin-Induced Skin Fibrosis by Promoting Accumulation of Bone Marrow-Derived Mesenchymal Stem Cells to the Lesion." Journal of Investigative Dermatology, 2016, 136(9): S255.

Li, L., et al., "Emerging Role of HMGB 1 in Fibrotic Diseases." Journal of Cellular and Molecular Medicine, 2014, 18 (12): 2331-2339.

Lund, L., et al., "The Registry of the International Society for Heart and Lung Transplantation: Thirty-Third Adult Heart Transplantation Report-2016; Focus Theme: Primary Diagnostic Indications for Transplant." The Journal of Heart and Lung Transplantation, 2016, 35(10): 1158-1169.

Narumi, T., et al., "High-Mobility Group Box 1-Mediated Heat Shock Protein Beta 1 Expression Attenuates Mitochondrial Dysfunction and Apoptosis." Journal of Molecular and Cellular Cardiology, 2015, 82: 1-12.

Park, J., et al., "Involvement of Toll-Like Receptors 2 and 4 in Cellular Activation by High Mobility Group Box 1 Protein." Journal of Biological Chemistry, 2004, 279(9): 7370-7377.

Racanelli, V., et al., "The Liver as an Immunological Organ." Hepatology, 2006, 43(2): Suppl. 1—S54-S62.

Raucci, A., et al., "The Janus Face of HMGB1 in Heart Disease: A Necessary Update." Cellular and Molecular Life Sciences, 2019, 76: 211-229.

Tamai, K. et al., U.S. Appl. No. 16/713,202, "Peptide for Inducing Regeneration of Tissue and Use Thereof." filed Dec. 13, 2019.

Tamai, K. et al., U.S. Appl. No. 16/768,654, "Therapeutic Agent for Inflammatory Bowel Disease." filed May 30, 2020.

Tao, A., et al., "Cardiomyocyte-Fibroblast Interaction Contributes to Diabetic Cardiomyopathy in Mice: Role of HMGB1/TLR4/IL-33 Axis" Biochimica et Biophysica Acta, 2015, 1852: 2075-2085.

Teoh, N., et al., "Low-Dose TNF-Alpha Protects Against Hepatic Ischemia-Reperfusion Injury In Mice: Implications for Preconditioning." Hepatology, 2003, 37(1): 118-128.

Tsung, A., et al., "Hepatic Ischemia/Reperfusion Injury Involves Functional TLR4 Signaling in Nonparenchymal Cells." The Journal of Immunology, 2005, 175(11): 7661-7668.

Ueta, M., et al., "Intracellularly Expressed TLR2s and TLR4s Contribution to an Immunosilent Environment at the Ocular Mucosal Epithelium." The Journal of Immunology, 2004, 173(5): 3337-3347.

(56) References Cited

OTHER PUBLICATIONS

Uronen-Hansson, H., et al., "Toll-like Receptor 2 (TLR2) and TLR4 are Present Inside Human Dendritic Cells, Associated with Microtubules and the Golgi Apparatus but are not Detectable on the Cell Surface: Integrity of Microtubules is Required for lnterieukin-12 Production in Response to Internalized Bacteria." Immunology, 2004, 111: 173-178.

Watanabe, T., et al., "The Role of HMGB-1 on the Development of Necrosis During Hepatic Ischemia and Hepatic Ischemia/Reperfusion Injury in Mice." Journal of Surgical Research, 2005, 124: 59-66.

Yang, S., et al., "Does Pretreatment of Bone Marrow Mesenchymal Stem Cells with 5-Azacytidine or Double Intravenous Infusion Improve Their Therapeutic Potential for Dilated Cardiomyopathy?" Medical Science Monitor Basic Research, 2013, 19: 20-31.

Yu, Q., et al., "Impact of Repeated Intravenous Bone Marrow Mesenchymal Stem Cells Infusion on Myocardial Collagen Network Remodeling in a Rat Model of Doxorubicin-Induced Dilated Cardiomyopathy." Molecular and Cellular Biochemistry, 2014: 279-285.

Hruby, V.J., "Designing peptide receptor agonists and antagonists" Nature Reviews Drug Discovery, 2002, 1(11) 847-858.

O'Callaghan, A., et al., "HMGB1 as a key mediator of tissueresponse to injury: roles ininflammation and tissue repair." European Surgery, 2006, 38(4): 283-292.

Tamai, K et al., U.S. Appl. No. 16/967,919, "Therapeutic Agent for Psoriasis." filed Aug. 6, 2020.

De Santis, S., et al., "TNFα deficiency results in increased IL-1β in an early onset of spontaneous murine colitis." Cell Death and Disease, 2017, e2993; doi: 10.1038/cddis.2017.397, pp. 1-7.

Seffernick, J.L., et al., "Melamine Deaminase and Atrazine Chlorohydrolase: 98 Percent Identical but Functionally Different." Journal of Bacteriology, Apr. 2001, 183(8): 2405-2410.

Whisstock, J.C., "Prediction of protein function from protein sequence and structure." Quarterly reviews of biophysics, 2003, 36(3): 307-340.

Witkowski, A., et al., "Conversion of a β-ketoacyl synthase to a malonyl decarboxylase by replacement of the active-site cysteine with glutamine " Biochemistry, 1999, 38(36): 11643-11650.

Zhou, Y.-H., et al., "High mobility group box 1 protein attenuates myocardial ischemia reperfusion injury via inhibition of the p38 mitogen-activated protein kinase signaling pathway." Experimental and Therapeutic Medicine, 2017, 14: 1582-1588.

Andersson, U., et al., "HMGB1 as a DNA-binding cytokine." Journal of Leukocyte Biology, Dec. 2002, 72(6) 1084-1091.

Tamai, K. et al., U.S. Appl. No. 17/281,862, "Peptide Possessing Mesenchymal-Stem-Cell Mobilizing Activity." filed Mar. 31, 2021.

Tamai, K. et al., U.S. Appl. No. 17/282,872, "Disease Treatment Drug Based On Mesenchymal-Stem-Cell Mobilization." filed Apr. 5, 2021.

Zhou, X., et al., "Section 2 The translation process of genetic information." Molecular Genetics, 1992, pp. 141-143.

\* cited by examiner

Nickel column-adsorbed fraction

←GST-His-HMGB-1

Heparin column-adsorbed fraction

←HMGB-1

Q column-adsorbed fraction

HMGB-1→

NaCl concentration (20mM→500mM)

S100A8

14 15 16 17 18 19 20 21 22 23 24 25 26 M 27 28 29 30 31 32 33 34 35 36 37 38 39 40

S100A9

14 15 16 17 18 19 20 21 22 23 24 25 26 M 27 28 29 30 31 32 33 34 35 36 37 38 39 40

SEQUENCE LISTING

```
<160> NUMBER OF SEQ ID NOS: 32

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Lys Gln Pro Tyr
        130                 135                 140

Glu Lys Lys Ala Ala Lys Leu Lys Glu Lys Tyr Glu Lys Asp Ile Ala
```

```
                145                 150                 155                 160
Ala Tyr Arg Ala Lys Gly Lys Pro Asp Ala Ala Lys Lys Gly Val Val
                    165                 170                 175

Lys Ala Glu Lys Ser Lys Lys Lys Glu Glu Glu Asp Glu Glu
                180                 185                 190

Asp Glu Glu Asp Glu Glu Glu Asp Glu Asp Glu Asp Glu
                195                 200                 205

Glu Glu Asp Asp Asp Asp Glu
        210                 215

<210> SEQ ID NO 2
<211> LENGTH: 648
<212> TYPE: DNA
<213> ORGANISM: Homo sapiens

<400> SEQUENCE: 2
atgggcaaag gagatcctaa gaagccgaga ggcaaaatgt catcatatgc atttttgtg      60 caaacttgtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaagcgga caaggcccgt tatgaaagag aaatgaaaac ctatatccct    240
cccaaagggg agacaaaaaa gaagttcaag gatcccaatg cacccaagag gcctccttcg    300
gccttcttcc tcttctgctc tgagtatcgc ccaaaaatca aggagaaca tcctggcctg    360 tccattggtg atgttgcgaa gaaactggga gagatgtgga ataacactgc tgcagatgac    420
aagcagcctt atgaaaagaa ggctgcgaag ctgaaggaaa atacgaaaa ggatattgct    480 gcatatcgag ctaaaggaaa gcctgatgca gcaaaaaagg gagttgtcaa ggctgaaaaa    540
agcaagaaaa agaaggaaga ggaggaagat gaggaagatg aagaggatga ggaggaggag    600
gaagatgaag aagatgaaga tgaagaagaa gatgatgatg atgaataa                 648

<210> SEQ ID NO 3
<211> LENGTH: 215
<212> TYPE: PRT
<213> ORGANISM: Mus musculus

<400> SEQUENCE: 3

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140
```

```
Glu Lys Lys Ala Ala Lys Leu Lys Glu Lys Tyr Glu Lys Asp Ile Ala
            145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
        210                 215

<210> SEQ ID NO 4
<211> LENGTH: 648
<212> TYPE: DNA
<213> ORGANISM: Mus musculus

<400> SEQUENCE: 4
atgggcaaag gagatcctaa aaagccgaga ggcaaaatgt cctcatatgc attctttgtg      60
caaacttgcc gggaggagca agaagaag caccccggatg cttctgtcaa cttctcagag     120
ttctccaaga agtgctcaga gaggtggaag accatgtctg ctaaagaaaa ggggaaattt     180
gaagatatgg caaaggctga caaggctcgt tatgaaagag aaatgaaaac ctacatcccc     240
cccaaagggg agaccaaaaa gaagttcaag accccaatg cacccaagag gcctccttcg     300
gccttcttct tgttctgttc tgagtaccgc cccaaaatca aggcgagca tcctggctta     360
tccattggtg atgttgcaaa gaaactagga gagatgtgga caacactgc agcagatgac     420
aagcagccct atgagaagaa agctgccaag ctgaaggaga agtatgagaa ggatattgct     480
gcctacagag ctaaaggaaa acctgatgca gcgaaaaagg gggtggtcaa ggctgaaaag     540
agcaagaaaa agaaggaaga ggaagatgat gaggaggatg aagaggatga ggaagaggag     600
gaagaagagg aagacgaaga tgaagaagaa gatgatgatg atgaataa                  648

<210> SEQ ID NO 5
<211> LENGTH: 215
<212> TYPE: PRT
<213> ORGANISM: Rattus norvegicus

<400> SEQUENCE: 5

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140
```

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Lys Lys Gly Val Val
            165                 170                 175

Lys Ala Glu Lys Ser Lys Lys Lys Glu Glu Glu Asp Asp Glu Glu
        180                 185                 190

Asp Glu Glu Asp Glu Glu Glu Glu Glu Glu Asp Glu Asp Glu
        195                 200                 205

Glu Glu Asp Asp Asp Asp Glu
    210                 215

<210> SEQ ID NO 6
<211> LENGTH: 648
<212> TYPE: DNA
<213> ORGANISM: Rattus norvegicus

<400> SEQUENCE: 6
atgggcaaag gagatcctaa gaagccgaga ggcaaaatgt cctcatatgc attctttgtg      60
caaacctgcc gggaggagca caagaagaag caccccggatg cttctgtcaa cttctcagag    120
ttctccaaga agtgctcaga gaggtggaag accatgtctg ctaaagaaaa ggggaaattt     180
gaagatatgg caaaggctga caaggctcgt tatgaaagag aaatgaaaac ctacatcccc     240
cccaaagggg agaccaaaaa gaagttcaag acccccaatg cccccaagag gcctccttcg     300
gccttcttct tgttctgttc tgagtaccgc ccaaaaatca aggcgagca tcctggctta     360 tccattggtg atgttgcgaa gaaactagga gagatgtgga caacactgc tgcggatgac     420 aagcagccct atgaaaagaa ggccgccaag ctgaaggaga gtatgagaa ggatattgct     480 gcctacagag ctaaaggaaa acctgatgca gcgaaaaagg gggtggtcaa ggctgagaag    540
agcaagaaaa agaaggaaga ggaagacgac gaggaggatg aagaggatga ggaagaggag    600
gaagaggagg aagacgaaga tgaagaagaa gatgatgatg atgaataa                  648

<210> SEQ ID NO 7
<211> LENGTH: 209
<212> TYPE: PRT
<213> ORGANISM: Homo sapiens

<400> SEQUENCE: 7

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
            85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr

-continued

```
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Glu Asp Glu Asp Glu
        195                 200                 205

Glu

<210> SEQ ID NO 8
<211> LENGTH: 630
<212> TYPE: DNA
<213> ORGANISM: Homo sapiens

<400> SEQUENCE: 8
atgggtaaag gagaccccaa caagccgcgg ggcaaaatgt cctcgtacgc cttcttcgtg      60
cagacctgcc gggaagagca caagaagaaa cacccggact cttccgtcaa tttcgcggaa     120
ttctccaaga agtgttcgga gagatggaag accatgtctg caaaggagaa gtcgaagttt     180
gaagatatgg caaaaagtga caaagctcgc tatgacaggg agatgaaaaa ttacgttcct     240
cccaaaggtg ataagaaggg gaagaaaaag gaccccaatg ctcctaaaag gccaccatct     300
gccttcttcc tgttttgctc tgaacatcgc ccaaagatca aaagtgaaca ccctggccta     360
tccattgggg atactgcaaa gaaattgggt gaaatgtggt ctgagcagtc agccaaagat     420
aaacaaccat atgaacagaa agcagctaag ctaaaggaga aatatgaaaa ggatattgct     480
gcatatcgtg ccaagggcaa aagtgaagca ggaaagaagg gccctggcag gccaacaggc     540
tcaaagaaga agaacgaacc agaagatgag gaggaggagg aggaagaaga agatgaagat     600
gaggaggaag aggatgaaga tgaagaataa                                      630

<210> SEQ ID NO 9
<211> LENGTH: 210
<212> TYPE: PRT
<213> ORGANISM: Mus musculus

<400> SEQUENCE: 9

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Leu Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu Asn Arg Pro Lys
            100                 105                 110

Ile Lys Ile Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
```

```
            130                 135                 140
Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190

Glu Glu Glu Glu Glu Glu Glu Glu Asp Asp Glu Glu Glu Glu Glu Asp
            195                 200                 205

Glu Glu
    210

<210> SEQ ID NO 10
<211> LENGTH: 633
<212> TYPE: DNA
<213> ORGANISM: Mus musculus

<400> SEQUENCE: 10
atgggcaagg gtgaccccaa caagccgcgg ggcaaaatgt cctcgtacgc cttcttcgtg      60
cagacctgcc gcgaggagca caagaagaag catcccgact cgtcggtgaa cttcgccgag     120
ttctccaaga aatgctccga gagatggaag accatgtctg caaaggaaaa gtccaagttt     180
gaagatttgg ccaagagcga caaagctcgt tatgacaggg agatgaagaa ctatgttcct     240
cccaaagggg ataagaaagg aaagaaaaaa gaccccaatg ctccgaagag accaccgtct     300
gccttcttcc tgttttgctc tgaaaatcgc ccaaagatca aaattgaaca cccaggcctg     360
tctattggag atactgcgaa gaaactgggt gagatgtggt ctgagcaatc tgccaaagat     420
aaacaaccgt atgagcagaa agcagctaaa ctaaaggaga gtatgaaaaa ggatattgct     480
gcataccgtg ccaagggcaa aagtgaagca ggaaagaagg gtcctggtag ccaacaggc     540 tcaaagaaga gaacgaacc agaagatgag gaggaggaag agaggagga agaggaggaa      600 gatgacgagg aagaagagga ggatgaagaa taa                                   633

<210> SEQ ID NO 11
<211> LENGTH: 210
<212> TYPE: PRT
<213> ORGANISM: Rattus norvegicus

<400> SEQUENCE: 11

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ser Ser Val Asn Phe Ala Glu Phe Ser Lys Lys Cys Ser Glu Arg
            35                  40                  45

Trp Lys Thr Met Ser Ala Lys Glu Lys Ser Lys Phe Glu Asp Leu Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
            115                 120                 125
```

```
Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Val Gly Lys Lys Gly Pro Gly
            165                 170                 175

Arg Pro Thr Gly Ser Lys Lys Asn Glu Pro Glu Asp Glu Glu Glu
            180                 185                 190

Glu Glu Glu Glu Glu Asp Asp Glu Asp Glu Glu Glu Asp Glu Asp
                195                 200                 205

Glu Glu
210
```

<210> SEQ ID NO 12
<211> LENGTH: 633
<212> TYPE: DNA
<213> ORGANISM: Rattus norvegicus

<400> SEQUENCE: 12

```
atgggcaagg gggaccccaa caagccgcgg ggcaagatgt cctcgtacgc cttcttcgtg      60
cagacctgcc gggaggagca caagaagaag catcccgact cgtcggtcaa cttcgccgag     120
ttctcgaaga atgttcgga gagatggaag accatgtctg ccaaggaaaa gtcgaagttt     180
gaggatttgg ccaagagcga caaagctcgt tatgacaggg agatgaagaa ctatgttcct     240
cccaaaggtg ataagaaagg aaagaaaaaa gatccaaatg ctcccaagag accaccgtct     300
gccttcttcc tgttttgctc tgaacatcgc ccaaagatca aaagtgaaca ccccggcctg     360
tctattggag atactgcaaa gaaactgggg gagatgtggt ctgagcaatc tgccaaagat     420
aaacaaccgt atgagcagaa agcagctaaa ctaaaggaga gtatgaaaaa ggatattgct     480
gcataccgtg ccaagggcaa aagtgaagta ggaaagaagg gtcctggtag gccaacaggc     540
tcaaagaaga gaatgaacc agaagatgag gaagaggagg aggaggaaga agatgatgaa     600
gatgaagagg aggaagatga ggatgaagaa taa                                 633
```

<210> SEQ ID NO 13
<211> LENGTH: 200
<212> TYPE: PRT
<213> ORGANISM: Homo sapiens

<400> SEQUENCE: 13

```
Met Ala Lys Gly Asp Pro Lys Lys Pro Lys Gly Lys Met Ser Ala Tyr
1               5                  10                  15

Ala Phe Phe Val Gln Thr Cys Arg Glu Glu His Lys Lys Lys Asn Pro
                20                  25                  30

Glu Val Pro Val Asn Phe Ala Glu Phe Ser Lys Lys Cys Ser Glu Arg
            35                  40                  45

Trp Lys Thr Met Ser Gly Lys Glu Lys Ser Lys Phe Asp Glu Met Ala
    50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Lys Leu Gly
        115                 120                 125
```

Glu Met Trp Asn Asn Leu Asn Asp Ser Glu Lys Gln Pro Tyr Ile Thr
            130                 135                 140
Lys Ala Ala Lys Leu Lys Glu Lys Tyr Glu Lys Asp Val Ala Asp Tyr
145                 150                 155                 160
Lys Ser Lys Gly Lys Phe Asp Gly Ala Lys Gly Pro Ala Lys Val Ala
                165                 170                 175
Arg Lys Lys Val Glu Glu Asp Glu Glu Glu Glu Glu Glu Glu
                180                 185                 190
Glu Glu Glu Glu Glu Glu Asp Glu
            195                 200

<210> SEQ ID NO 14
<211> LENGTH: 603
<212> TYPE: DNA
<213> ORGANISM: Homo sapiens

<400> SEQUENCE: 14
atggctaaag gtgacccaa gaaaccaaag gcaagatgt ccgcttatgc cttctttgtg      60
cagacatgca gagaagaaca taagaagaaa aacccagagg tccctgtcaa ttttgcggaa     120
ttttccaaga agtgctctga gaggtggaag acgatgtccg ggaaagagaa atctaaattt     180
gatgaaatgg caaaggcaga taaagtgcgc tatgatcggg aaatgaagga ttatggacca     240
gctaagggag gcaagaagaa gaggatcct aatgctccca aaggccacc gtctggattc     300 ttcctgttct gttcagaatt ccgccccaag atcaaatcca caacccccgg catctctatt     360
ggagacgtgg caaaaaagct gggtgagatg tggaataatt taaatgacag tgaaaagcag     420
ccttacatca ctaaggcggc aaagctgaag gagaagtatg agaaggatgt tgctgactat     480
aagtcgaaag gaaagtttga tggtgcaaag ggtcctgcta agttgcccg gaaaaggtg      540 gaagaggaag atgaagaaga ggaggaggaa gaagaggagg aggaggagga ggaggatgaa    600
taa                                                                  603

<210> SEQ ID NO 15
<211> LENGTH: 200
<212> TYPE: PRT
<213> ORGANISM: Mus musculus

<400> SEQUENCE: 15

Met Ala Lys Gly Asp Pro Lys Pro Lys Gly Lys Met Ser Ala Tyr
1               5                   10                  15
Ala Phe Phe Val Gln Thr Cys Arg Glu Glu His Lys Lys Lys Asn Pro
                20                  25                  30
Glu Val Pro Val Asn Phe Ala Glu Phe Ser Lys Lys Cys Ser Glu Arg
            35                  40                  45
Trp Lys Thr Met Ser Ser Lys Glu Lys Ser Lys Phe Asp Glu Met Ala
        50                  55                  60
Lys Ala Asp Lys Val Arg Tyr Asp Arg Glu Met Lys Asp Tyr Gly Pro
65                  70                  75                  80
Ala Lys Gly Gly Lys Lys Lys Asp Pro Asn Ala Pro Lys Arg Pro
                85                  90                  95
Pro Ser Gly Phe Phe Leu Phe Cys Ser Glu Phe Arg Pro Lys Ile Lys
                100                 105                 110
Ser Thr Asn Pro Gly Ile Ser Ile Gly Asp Val Ala Lys Lys Leu Gly
            115                 120                 125
Glu Met Trp Asn Asn Leu Ser Asp Asn Glu Lys Gln Pro Tyr Val Thr

```
                130               135                140
Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Glu Glu Glu Glu Glu Glu Glu Glu Glu
            180                 185                 190

Glu Glu Glu Glu Glu Glu Asp Glu
        195                 200

<210> SEQ ID NO 16
<211> LENGTH: 603
<212> TYPE: DNA
<213> ORGANISM: Mus musculus

<400> SEQUENCE: 16
atggctaaag gtgaccccaa gaaaccaaag ggcaagatgt ctgcttatgc cttctttgtg      60
cagacatgca ggaagaaca taagaagaaa acccagagg ttcccgtcaa ttttgctgag       120
ttctccaaga agtgctcgga gaggtggaag accatgtcta gcaaagagaa atcaaagttt    180
gatgaaatgg caaaggcaga taaagtccga tatgatcggg agatgaaaga ttatggacca    240
gctaaaggag gcaagaagaa gaaggaccca atgcccccca aaagacctcc gtctggattt    300
ttcttattct gctctgaatt ccgccccaag atcaaatcca caacccctgg catctccatt    360
ggagatgtgg caaaaaagct gggtgagatg tggaataact taagtgacaa tgaaaagcag    420
ccttatgtca ccaaggcagc aaagctgaag gagaagtatg agaaggatgt tgctgactat    480
aagtctaaag ggaagtttga tggtgccaag ggtcctgcta agttgcccg gaaaaaggtg     540 gaagaagagg aagaggagga ggaagaggaa gaagaggagg aggaagagga ggaagatgaa    600
taa                                                                  603

<210> SEQ ID NO 17
<211> LENGTH: 89
<212> TYPE: PRT
<213> ORGANISM: Mus musculus

<400> SEQUENCE: 17

Met Pro Ser Glu Leu Glu Lys Ala Leu Ser Asn Leu Ile Asp Val Tyr
1                 5                  10                  15

His Asn Tyr Ser Asn Ile Gln Gly Asn His His Ala Leu Tyr Lys Asn
                20                  25                  30

Asp Phe Lys Lys Met Val Thr Thr Glu Cys Pro Gln Phe Val Gln Asn
            35                  40                  45

Ile Asn Ile Glu Asn Leu Phe Arg Glu Leu Asp Ile Asn Ser Asp Asn
        50                  55                  60

Ala Ile Asn Phe Glu Glu Phe Leu Ala Met Val Ile Lys Val Gly Val
65                  70                  75                  80

Ala Ser His Lys Asp Ser His Lys Glu
                85

<210> SEQ ID NO 18
<211> LENGTH: 270
<212> TYPE: DNA
<213> ORGANISM: Mus musculus

<400> SEQUENCE: 18
atgccgtctg aactggagaa ggccttgagc aacctcattg atgtctacca caattattcc      60
```
aatatacaag gaaatcacca tgccctctac aagaatgact tcaagaaaat ggtcactact    120
gagtgtcctc agtttgtgca gaatataaat atcgaaaact tgttcagaga attggacatc    180
aatagtgaca atgcaattaa cttcgaggag ttccttgcga tggtgataaa agtgggtgtg    240
gcatctcaca agacagcca caaggagtag                                     270

<210> SEQ ID NO 19
<211> LENGTH: 89
<212> TYPE: PRT
<213> ORGANISM: Rattus norvegicus

<400> SEQUENCE: 19

Met Ala Thr Glu Leu Glu Lys Ala Leu Ser Asn Val Ile Glu Val Tyr
1               5                   10                  15

His Asn Tyr Ser Gly Ile Lys Gly Asn His His Ala Leu Tyr Arg Asp
            20                  25                  30

Asp Phe Arg Lys Met Val Thr Thr Glu Cys Pro Gln Phe Val Gln Asn
        35                  40                  45

Lys Asn Thr Glu Ser Leu Phe Lys Glu Leu Asp Val Asn Ser Asp Asn
    50                  55                  60

Ala Ile Asn Phe Glu Glu Phe Leu Ala Leu Val Ile Arg Val Gly Val
65                  70                  75                  80

Ala Ala His Lys Asp Ser His Lys Glu
                85

<210> SEQ ID NO 20
<211> LENGTH: 270
<212> TYPE: DNA
<213> ORGANISM: Rattus norvegicus

<400> SEQUENCE: 20
atggcaactg aactggagaa ggccttgagc aacgtcattg aagtctacca caattattct     60
ggtataaaag gaatcacca tgccctctac agggatgact tcaggaaaat ggtcactact    120
gagtgccctc agtttgtgca gaataaaaat accgaaagct tgttcaaaga attggacgtc    180
aatagtgaca acgcaattaa cttcgaagag ttccttgcgt tggtgataag ggtgggcgtg    240
gcagctcata agacagcca caaggagtaa                                     270

<210> SEQ ID NO 21
<211> LENGTH: 93
<212> TYPE: PRT
<213> ORGANISM: Homo sapiens

<400> SEQUENCE: 21

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 22
<211> LENGTH: 282
<212> TYPE: DNA
<213> ORGANISM: Homo sapiens

<400> SEQUENCE: 22

```
atgttgaccg agctggagaa agccttgaac tctatcatcg acgtctacca caagtactcc      60
ctgataaagg ggaatttcca tgccgtctac agggatgacc tgaagaaatt gctagagacc     120
gagtgtcctc agtatatcag gaaaaagggt gcagacgtct ggttcaaaga gttggatatc     180
aacactgatg gtgcagttaa cttccaggag ttcctcattc tggtgataaa gatgggcgtg     240
gcagcccaca aaaaaagcca tgaagaaagc cacaaagagt ag                        282
```

<210> SEQ ID NO 23
<211> LENGTH: 113
<212> TYPE: PRT
<213> ORGANISM: Mus musculus

<400> SEQUENCE: 23

```
Met Ala Asn Lys Ala Pro Ser Gln Met Glu Arg Ser Ile Thr Thr Ile
1               5                   10                  15

Ile Asp Thr Phe His Gln Tyr Ser Arg Lys Glu Gly His Pro Asp Thr
            20                  25                  30

Leu Ser Lys Lys Glu Phe Arg Gln Met Val Glu Ala Gln Leu Ala Thr
        35                  40                  45

Phe Met Lys Lys Glu Lys Arg Asn Glu Ala Leu Ile Asn Asp Ile Met
    50                  55                  60

Glu Asp Leu Asp Thr Asn Gln Asp Asn Gln Leu Ser Phe Glu Glu Cys
65                  70                  75                  80

Met Met Leu Met Ala Lys Leu Ile Phe Ala Cys His Glu Lys Leu His
                85                  90                  95

Glu Asn Asn Pro Arg Gly His Gly His Ser His Gly Lys Gly Cys Gly
            100                 105                 110

Lys
```

<210> SEQ ID NO 24
<211> LENGTH: 342
<212> TYPE: DNA
<213> ORGANISM: Mus musculus

<400> SEQUENCE: 24

```
atggccaaca aagcaccttc tcagatggag cgcagcataa ccaccatcat cgacaccttc      60
catcaatact ctaggaagga aggacaccct gacaccctga gcaagaagga attcagacaa     120
atggtggaag cacagttggc aacctttatg aagaaagaga gagaaatgaa gccctcata     180 aatgacatca tggaggacct ggacacaaac caggacaatc agctgagctt tgaggagtgt     240
atgatgctga tggcaaagtt gatctttgcc tgtcatgaga agctgcatga gaacaaccca     300
cgtgggcatg gccacagtca tggcaaaggc tgtgggaagt aa                        342
```

<210> SEQ ID NO 25
<211> LENGTH: 113
<212> TYPE: PRT
<213> ORGANISM: Rattus norvegicus

<400> SEQUENCE: 25

```
Met Ala Ala Lys Thr Gly Ser Gln Leu Glu Arg Ser Ile Ser Thr Ile
1               5                   10                  15
```

```
Ile Asn Val Phe His Gln Tyr Ser Arg Lys Tyr Gly His Pro Asp Thr
             20                  25                  30

Leu Asn Lys Ala Glu Phe Lys Glu Met Val Asn Lys Asp Leu Pro Asn
         35                  40                  45

Phe Leu Lys Arg Glu Lys Arg Asn Glu Asn Leu Leu Arg Asp Ile Met
 50                  55                  60

Glu Asp Leu Asp Thr Asn Gln Asp Asn Gln Leu Ser Phe Glu Cys
 65                  70                  75                  80

Met Met Leu Met Gly Lys Leu Ile Phe Ala Cys His Glu Lys Leu His
                 85                  90                  95

Glu Asn Asn Pro Arg Gly His Asp His Arg His Gly Lys Gly Cys Gly
                100                 105                 110

Lys
```

<210> SEQ ID NO 26
<211> LENGTH: 342
<212> TYPE: DNA
<213> ORGANISM: Rattus norvegicus

<400> SEQUENCE: 26

```
atggctgcca aaacaggatc tcagctggag cgcagcataa gcaccatcat caatgttttc    60
catcagtact ctaggaagta tggacatcct gacaccctga caaggcgga attcaaagaa    120
atggtgaata aggacttgcc aaattttctg aagagggaga aagaaatga aatctccta    180
agagacatca tggaggacct ggacacaaac caggacaatc aactgtcctt tgaggagtgt    240
atgatgctga tgggaaagtt gatctttgcc tgtcatgaga gctgcatga gaacaaccca    300
cgtgggcatg accacaggca cggcaaaggc tgtgggaagt aa                      342
```

<210> SEQ ID NO 27
<211> LENGTH: 116
<212> TYPE: PRT
<213> ORGANISM: Homo sapiens

<400> SEQUENCE: 27

```
Met Thr Cys Lys Met Ser Gln Leu Glu Arg Asn Ile Glu Thr Ile Ile
 1               5                  10                  15

Asn Thr Pro His Glu His Gln Tyr Ser Val Lys Leu Gly His Pro Asp
             20                  25                  30

Thr Leu Asn Gln Gly Glu Phe Lys Glu Leu Val Arg Lys Asp Leu Gln
         35                  40                  45

Asn Phe Leu Lys Lys Glu Asn Lys Asn Glu Lys Val Ile Glu His Ile
 50                  55                  60

Met Glu Asp Leu Asp Thr Asn Ala Asp Lys Gln Leu Ser Phe Glu Glu
 65                  70                  75                  80

Phe Ile Met Leu Met Ala Arg Leu Thr Trp Ala Ser His Glu Lys Met
                 85                  90                  95

His Glu Gly Asp Glu Gly Pro Gly His His Lys Pro Gly Leu Gly
                100                 105                 110

Glu Gly Thr Pro
        115
```

<210> SEQ ID NO 28
<211> LENGTH: 345
<212> TYPE: DNA
<213> ORGANISM: Homo sapiens

<400> SEQUENCE: 28

```
atgacttgca aaatgtcgca gctggaacgc aacatagaga ccatcatcaa caccttccac    60
caatactctg tgaagctggg gcacccagac accctgaacc aggggggaatt caaagagctg   120
gtgcgaaaag atctgcaaaa ttttctcaag aaggagaata agaatgaaaa ggtcatagaa   180
cacatcatgg aggacctgga cacaaatgca gacaagcagc tgagcttcga ggagttcatc   240
atgctgatgg cgaggctaac ctgggcctcc cacgagaaga tgcacgaggg tgacgagggc   300
cctggccacc accataagcc aggcctcggg gagggcaccc cctaa                    345
```

<210> SEQ ID NO 29
<211> LENGTH: 63
<212> TYPE: DNA
<213> ORGANISM: Artificial
<220> FEATURE:
<223> OTHER INFORMATION: An artificially synthesized nucleotide sequence

<400> SEQUENCE: 29

```
atgcagacag acacactcct gctatgggta ctgctgctgt gggttccagg ttccactggt    60
gac                                                                   63
```

<210> SEQ ID NO 30
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 30

```
Asp Tyr Lys Asp Asp Asp Lys
1               5
```

<210> SEQ ID NO 31
<211> LENGTH: 220
<212> TYPE: PRT
<213> ORGANISM: Artificial
<220> FEATURE:
<223> OTHER INFORMATION: An artificially synthesized peptide sequence

<400> SEQUENCE: 31

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
```

```
                145                 150                 155                 160
Val Val Leu Tyr Met Asp Pro Met Cys Leu Asp Ala Phe Pro Lys Leu
                    165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp
        210                 215                 220

<210> SEQ ID NO 32
<211> LENGTH: 660
<212> TYPE: DNA
<213> ORGANISM: Artificial
<220> FEATURE:
<223> OTHER INFORMATION: An artificially synthesized nucleotide sequence

<400> SEQUENCE: 32
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgtttttaaa    540 aaacgtattg aagctatccc acaaattgat aagtacttga aatccagcaa gtatatagca     600
tggcctttgc agggctggca agccacgttt ggtggtggcg accatcctcc aaaatcggat     660
```

AGENTS FOR PROMOTING TISSUE REGENERATION BY RECRUITING BONE MARROW MESENCHYMAL STEM CELLS AND/OR PLURIPOTENT STEM CELLS INTO BLOOD

CROSS REFERENCE TO A RELATED APPLICATION

This application is a National Stage Application of International Application Number PCT/JP2010/069133, filed Oct. 28, 2010; which claims priority to Japanese Application No. 2009-247143, filed Oct. 28, 2009; all of which are incorporated herein by reference in their entirety.

TECHNICAL FIELD

The present invention relates to tissue regeneration-promoting agents that are administered to a tissue other than a tissue in need of regeneration.

BACKGROUND ART

Regenerative medicine aims at functional and structural regeneration of damaged organs, utilizing cells or tissues cultured and processed ex vivo. For example, a cultured skin sheet is produced by collecting skin cells from a patient or another person, culturing them outside the body, and processing them into a sheet form, and is then grafted onto damaged skin. In regenerative medicine, the ex vivo culture and proliferation of cells are required to obtain cells used for treatment. Since the culture procedure could cause deterioration of cells (senescence, tumorigenesis, or contamination with bacteria, viruses, etc.), it is essential for maintenance of safety that manufacturing be conducted in a facility certified as meeting the standards of Good Manufacturing Practice (GMP). This is expected to lead to the problem of high treatment costs.

Meanwhile, the living body has regeneration mechanisms for damage repair in case of organ damage. However, it is known that if damaged areas are large, they become filled with nonfunctional scar tissues. Damage healing with such scar tissues becomes an inhibitory factor for nerve regeneration in cerebral infarction or spinal cord damage, becomes a causative factor for cardiac rupture in myocardial infarction, or results in keloid formation in surgical wounds or extensive burns, thereby causing remarkably poor prognosis and QOL in the cosmetic aspect. If the body's own regeneration mechanisms for repairing tissue damage can be activated, it is expected to be possible to induce the regeneration of damaged tissues (organs) with functional tissues, rather than cicatrization.

The bone marrow is known to contain mesenchymal stem cells which can differentiate into bone, cartilage, adipose, and others, as well as hematopoietic stem cells which differentiate into leukocytes, erythrocytes, and the like. Recently, it has been revealed that the bone marrow also contains pluripotent stem cells that can differentiate into epithelial cells and nerve cells.

PRIOR-ART DOCUMENTS

Patent Documents

Patent Document 1: WO 2008/053892

DISCLOSURE OF THE INVENTION

Problems to be Solved by the Invention

An objective of the present invention is to develop a novel therapeutic method by which the physiological regeneration/repair mechanism is activated to induce the healing of damaged tissues, thereby treating intractable diseases such as extensive skin ulcer, intractable bone fracture, and cerebral infarction, which are difficult to cure by conventional therapeutic methods.

Means for Solving the Problems

The effect of HMGB-1 and S100A8 in recruiting bone marrow-derived cells to a skin ulcer in the process of skin ulcer healing was assessed using mice. The result demonstrated that the administration of HMGB-1 or S100A8 into venous blood, which was a non-target site distant from the skin ulcer, resulted in recruitment of bone marrow-derived cells to the skin ulcer. Then, the effect of the intravenous administration of HMGB-1 and S100A8 in promoting the healing of skin ulcer was assessed. As a result, the healing of the skin ulcer was successfully promoted by HMGB-1 and S100A8 administered to a blood vessel, which was a non-target site distant from the ulceration site. In addition, the assessment of their effect of promoting the scarless healing of skin ulcer showed that the intravenous administration of HMGB-1 could promote the early closure and scarless healing of skin ulcer by augmenting the further recruitment of bone marrow-derived cells recruited to the blood into the ulceration site.

Furthermore, cerebral infarction model mice were tested for the presence of bone marrow-derived cells in their brains. As a result, bone marrow-derived cells expressing nerve cell markers were detected in the brain of mice to which HMGB-1 was intravenously administered after creation of cerebral infarction. Then, the assessment of the cerebral infarct-reducing effect showed that the cerebral infarction was remarkably improved in the mice to which HMGB-1 was intravenously administered, as compared to control mice. In addition, the assessment for the improvement of the post-cerebral infarction survival rate revealed that the intravenous HMGB-1 administration resulted in an increase in the mouse survival rate.

Further assessment was carried out using mice to clarify whether bone marrow pluripotent stem cells from regions other than the bone fracture site were involved in the process of bone fracture healing. The result showed that bone marrow-derived cells migrated from regions distant from the damaged site into the bone fracture site to repair the damaged tissue.

Moreover, another test was performed using bone fracture model mice to assess the activity of intravenously administered HMGB1 in recruiting bone marrow mesenchymal stem cells to the damaged site. It was revealed that the intravenous administration of HMGB1 resulted in the accumulation of bone marrow mesenchymal stem cells recruited to the blood at the bone fracture site.

Based on these findings, the present application provides the following inventions:

[1] a tissue regeneration-promoting agent, comprising any one of:
   (a) an HMGB1 protein;
   (b) a cell that secretes an HMGB1 protein;
   (c) a vector into which a DNA encoding an HMGB1 protein is inserted;

(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;
(o) a vector into which a DNA encoding an S100A9 protein is inserted;
(p) a cell or tissue extract; and
(q) a heparin-binding fraction of a cell or tissue extract; wherein the agent is administered to a tissue other than a tissue in need of regeneration.
[2] the agent of [1], which is administered parenterally;
[3] the agent of [2], which is administered by injection;
[4] the agent of [1], which is administered intravascularly, intramuscularly, subcutaneously, intradermally, or intraperitoneally;
[5] the agent of any one of [1] to [4], wherein the cell or tissue extract is produced by a method comprising the step of immersing a cell or tissue in a solvent;
[6] the agent of any one of [1] to [4], wherein the heparin-binding fraction of a cell or tissue extract is produced by a method comprising the steps of:
  (a) immersing a cell or tissue in a solvent;
  (b) contacting immobilized heparin with the extract prepared in step (a); and
  (c) eluting a heparin-binding fraction from the immobilized heparin;
[7] the agent of any one of [1] to [6] for use in promoting the regeneration of a nerve, bone, or skin tissue;
[8] a kit for promoting tissue regeneration, which comprises a composition comprising any one of:
  (a) an HMGB1 protein;
  (b) a cell that secretes an HMGB1 protein;
  (c) a vector into which a DNA encoding an HMGB1 protein is inserted;
  (d) an HMGB2 protein
  (e) a cell that secretes an HMGB2 protein;
  (f) a vector into which a DNA encoding an HMGB2 protein is inserted;
  (g) an HMGB3 protein;
  (h) a cell that secretes an HMGB3 protein;
  (i) a vector into which a DNA encoding an HMGB3 protein is inserted;
  (j) an S100A8 protein;
  (k) a cell that secretes an S100A8 protein;
  (l) a vector into which a DNA encoding an S100A8 protein is inserted;
  (m) an S100A9 protein;
  (n) a cell that secretes an S100A9 protein;
  (o) a vector into which a DNA encoding an S100A9 protein is inserted;
  (p) a cell or tissue extract; and
  (q) a heparin-binding fraction of a cell or tissue extract; wherein the composition is administered to a tissue other than a tissue in need of regeneration.
[9] the kit of [8], which is administered parenterally;
[10] the kit of [9], which is administered by injection;
[11] the kit of [8], which is administered intravascularly, intramuscularly, subcutaneously, intradermally, or intraperitoneally;
[12] the kit of any one of [8] to [11], which is used to promote the regeneration of a nerve, bone, or skin tissue;
[13] a method for promoting tissue regeneration, which comprises the step of administering an effective amount of a composition to a tissue other than a tissue in need of regeneration, wherein the composition comprises any one of:
  (a) an HMGB1 protein;
  (b) a cell that secretes an HMGB1 protein;
  (c) a vector into which a DNA encoding an HMGB1 protein is inserted;
  (d) an HMGB2 protein
  (e) a cell that secretes an HMGB2 protein;
  (f) a vector into which a DNA encoding an HMGB2 protein is inserted;
  (g) an HMGB3 protein;
  (h) a cell that secretes an HMGB3 protein;
  (i) a vector into which a DNA encoding an HMGB3 protein is inserted;
  (j) an S100A8 protein;
  (k) a cell that secretes an S100A8 protein;
  (l) a vector into which a DNA encoding an S100A8 protein is inserted;
  (m) an S100A9 protein;
  (n) a cell that secretes an S100A9 protein;
  (o) a vector into which a DNA encoding an S100A9 protein is inserted;
  (p) a cell or tissue extract; and
  (q) a heparin-binding fraction of a cell or tissue extract;
[14] the method of [13], wherein the administration is parenteral administration;
[15] the method of [14], wherein the administration is injection;
[16] the method of [13], wherein the administration is intravascular, intramuscular, subcutaneous, intradermal, or intraperitoneal administration;
[17] the method of any one of [13] to [16], which promotes the regeneration of a nerve, bone, or skin tissue;
[18] use of a composition in producing a tissue regeneration-promoting agent, wherein the composition comprises any one of:
  (a) an HMGB1 protein;
  (b) a cell that secretes an HMGB1 protein;
  (c) a vector into which a DNA encoding an HMGB1 protein is inserted;
  (d) an HMGB2 protein
  (e) a cell that secretes an HMGB2 protein;
  (f) a vector into which a DNA encoding an HMGB2 protein is inserted;
  (g) an HMGB3 protein;
  (h) a cell that secretes an HMGB3 protein;
  (i) a vector into which a DNA encoding an HMGB3 protein is inserted;
  (j) an S100A8 protein;
  (k) a cell that secretes an S100A8 protein;
  (l) a vector into which a DNA encoding an S100A8 protein is inserted;
  (m) an S100A9 protein;
  (n) a cell that secretes an S100A9 protein;
  (o) a vector into which a DNA encoding an S100A9 protein is inserted;
  (p) a cell or tissue extract; and
  (q) a heparin-binding fraction of a cell or tissue extract;

wherein the agent is administered to a tissue other than a tissue in need of regeneration;

[19] the use of [18], wherein the agent is administered parenterally;

[20] the use of [19], wherein the administration is injection;

[21] the use of [18], wherein the agent is administered intravascularly, intramuscularly, subcutaneously, intradermally, or intraperitoneally;

[22] the use of any one of [18] to [21], wherein the agent is an agent for promoting the regeneration of a nerve, bone, or skin tissue;

[23] a composition for use in a method of promoting tissue regeneration, comprising any one of:
  (a) an HMGB1 protein;
  (b) a cell that secretes an HMGB1 protein;
  (c) a vector into which a DNA encoding an HMGB1 protein is inserted;
  (d) an HMGB2 protein
  (e) a cell that secretes an HMGB2 protein;
  (f) a vector into which a DNA encoding an HMGB2 protein is inserted;
  (g) an HMGB3 protein;
  (h) a cell that secretes an HMGB3 protein;
  (i) a vector into which a DNA encoding an HMGB3 protein is inserted;
  (j) an S100A8 protein;
  (k) a cell that secretes an S100A8 protein;
  (l) a vector into which a DNA encoding an S100A8 protein is inserted;
  (m) an S100A9 protein;
  (n) a cell that secretes an S100A9 protein;
  (o) a vector into which a DNA encoding an S100A9 protein is inserted;
  (p) a cell or tissue extract; and
  (q) a heparin-binding fraction of a cell or tissue extract;
wherein the composition is administered to a tissue other than a tissue in need of regeneration;

[24] the composition of [23], which is administered parenterally;

[25] the composition of [24], which is administered by injection;

[26] the composition of [23], which is administered intravascularly, intramuscularly, subcutaneously, intradermally, or intraperitoneally; and

[27] the composition of any one of [23] to [26], wherein the method for promoting tissue regeneration is a method for promoting the regeneration of a nerve, bone, or skin tissue.

Effects of the Invention

Cell growth factors such as HGF, EGF, VEGF, and FGF are known as pharmaceutical agents for regenerating damaged tissues. These are used with an expectation that they will promote cell growth when administered directly to a damaged site and its surrounding tissues.

HMGB1, HMGB2, HMGB3, S100A8, and S100A9 have activity of recruiting bone marrow pluripotent stem cells. Bone marrow pluripotent stem cells can differentiate into epithelial and nerve cells as well as mesenchymal cells. In the case of extensive tissue damage, if it is possible to recruit bone marrow pluripotent stem cells to the damaged site via bloodstream, they are expected to promote the functional regeneration/repair of damaged tissues.

The present invention provides methods for promoting repair of damaged tissues, in which HMGB1, HMGB2, HMGB3, S100A8, and S100A9, which are recruitment factors for bone marrow pluripotent stem cells, are administered at a site distant from a damaged site by intravenous administration or such, thereby recruiting bone marrow pluripotent stem cells to the peripheral blood. For example, in the treatment of a disease of deep-seated organ, such as cerebral infarction, it is difficult to administer a therapeutic agent directly to a damaged site (brain). On the other hand, in the present invention, such treatment can be carried out by intravenous administration, which is widely used in general medical practice. It is therefore possible to administer a therapeutic agent at any concentration and frequency in a safe and simple manner. This is a superior effect as compared to conventional therapeutic methods.

Meanwhile, a recently developed bone marrow cell-based method that is known to be effective in treating cerebral infarction involves the collection of cells from patient's bone marrow and re-administration of the cells into the bloodstream. This method is inevitably associated with severe invasion because bone marrow cells need to be aspirated with a large-bore needle inserted into the bone marrow, which is located deep inside the body. In contrast, the present invention allows bone marrow cells to be recruited directly to the bloodstream by intravenous administration of an agent, and therefore does not involve severe invasion even when the agent is frequently administered to cerebral infarction patients.

Bone marrow-derived pluripotent stem cells have the potential ability to differentiate into various types of cells such as mesenchymal cells, epithelial cells, and nerve cells. After migrating to a damaged site, they may differentiate depending on a niche environment surrounding the damaged site, and then induce tissue repair. In regenerative medicine and cell therapy, bone marrow pluripotent stem cells, which are rare cells, are expanded by ex vivo culture before use in the treatment. However, this requires adequate safety control because, unlike conventional pharmaceutical agents, there is a risk of deterioration of cells (canceration and contamination with bacteria, viruses, etc.) which may be caused during the culturing process. In the present invention, bone marrow pluripotent stem cells are recruited to the peripheral circulating blood by administration of HMGB1, HMGB2, HMGB3, S100A8, and/or S100A9. This is a highly safe therapeutic method because the cells are not removed from the body for artificial manipulation.

GFP expression was hardly detectable in the CD11b-positive cells. In contrast, GFP expression was observed in almost all CD11b-negative cells. This indicates that CD11b-positive cells are negative for PDGF receptor α while CD11b-negative cells are positive for PDGF receptor α.

Figure 43:
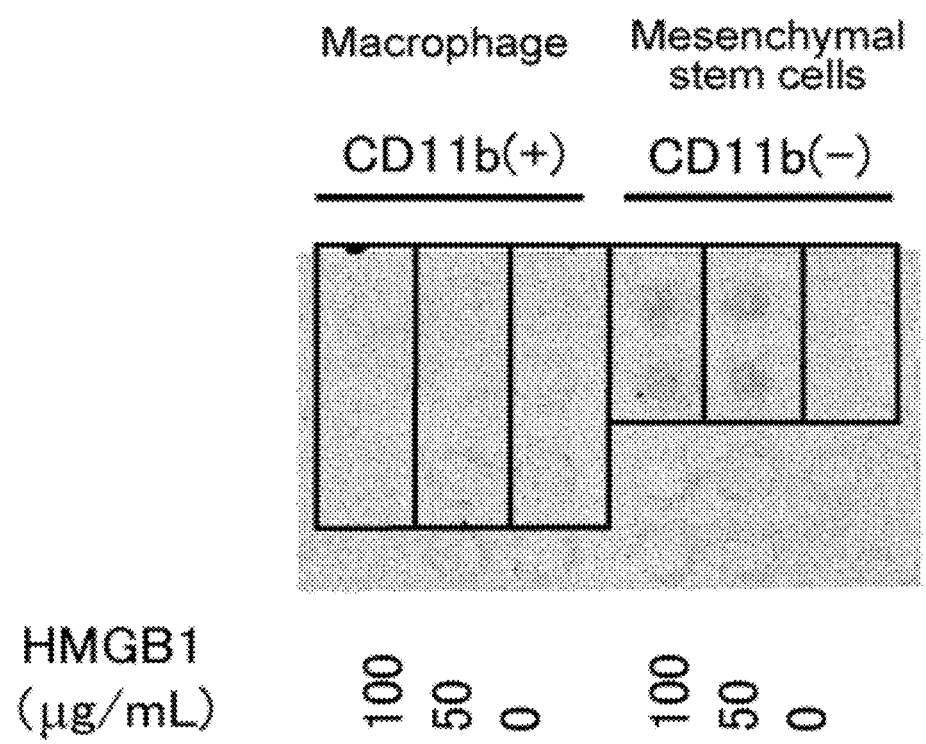

FIG. 43 is a photograph demonstrating that HMGB1 has migration-inducing activity on mesenchymal stem cells, which are CD11b-negative cells, while exhibiting little migration-inducing activity on macrophages, which are CD11b-positive cells.

Figure 44:
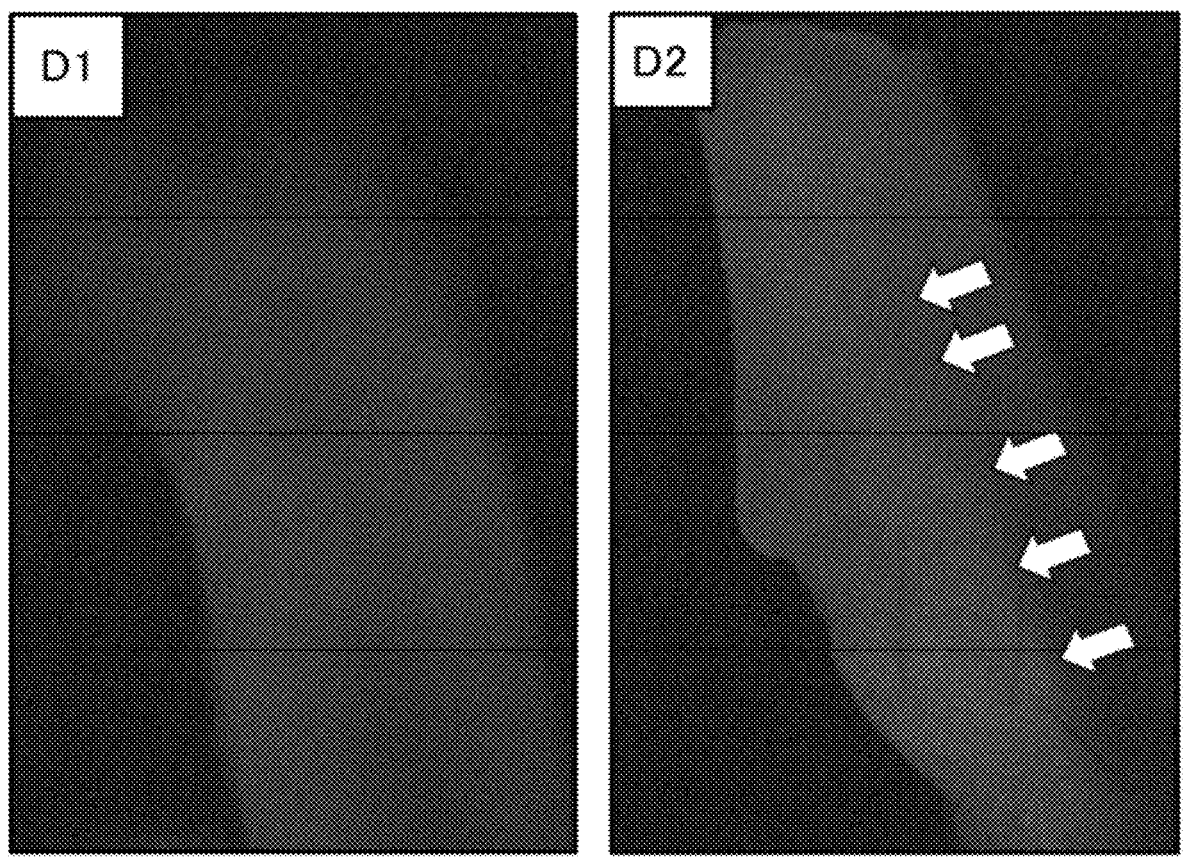

FIG. 44 is a photograph showing the result of GFP fluorescence (green fluorescence) observation of bone marrow mesenchymal cells accumulated at a site of bone fracture created in a PDGF receptor α-GFP mouse. It shows that more bone marrow mesenchymal cells were accumulated at the bone fracture site in the mouse to which HMGB1 was intravenously administered, than the negative control-administered mouse.

MODE FOR CARRYING OUT THE INVENTION

The present invention provides tissue regeneration-promoting agents comprising any one of the following substances, which are administered to a tissue other than a tissue in need of regeneration:

(a) an HMGB1 protein;
(b) a cell that secretes an HMGB1 protein;
(c) a vector into which a DNA encoding an HMGB1 protein is inserted;
(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;
(o) a vector into which a DNA encoding an S100A9 protein is inserted;
(p) a cell or tissue extract; and
(q) a heparin-binding fraction of a cell or tissue extract;

The tissue regeneration-promoting agents are characterized in that, when administered to a tissue other than a tissue in need of regeneration, they recruit (also referred to as "attract" or "locally attract") bone marrow cells from the bone marrow to the tissue in need of regeneration via the peripheral circulation. Herein, "peripheral circulation" is also referred to as "blood circulation" or "circulating peripheral bloodstream".

The tissue regeneration-promoting agents of the present invention preferably suppress scar healing and induce scarless healing. Scar healing refers to a state in which fibrillar collagen replaces functional tissues. On the other hand, scarless healing refers to a state in which a damaged site regenerates functional tissues composed of cellular components, and this is functionally and aesthetically superior to scar healing. The tissue regeneration-promoting agents of the present invention include such scarless tissue regeneration-promoting agents.

Accordingly, the agents of the present invention can also be referred to as:
tissue regeneration-promoting agents, which are administered to a tissue other than a tissue in need of regeneration, and which promote tissue regeneration by recruiting bone marrow cells to peripheral blood from the bone marrow and as a result recruiting bone marrow-derived cells to the tissue in need of regeneration via the peripheral circulation system;
scarless tissue regeneration-promoting agents, which are administered to a tissue other than a tissue in need of regeneration; or
scarless tissue regeneration-promoting agents, which are administered to a tissue other than a tissue in need of regeneration, and which promote tissue regeneration by recruiting bone marrow cells to peripheral blood from the bone marrow and as a result recruiting bone marrow-derived cells to the tissue in need of regeneration via the peripheral circulation system.

The tissue in need of regeneration includes, for example, damaged tissues, necrotic tissues, tissues after surgery, tissues with reduced function, fibrosing tissues, aged tissues, and diseased tissues. Examples of the tissues include live skin tissues and defect tissues caused by internal biopsy (surgery) (brain, lung, heart, liver, stomach, small intestine, large intestine, pancreas, kidney, urinary bladder, spleen, uterus, testis, blood, etc.).

In the present invention, administration to a tissue other than a tissue in need of regeneration refers to administration to a site that is not a site in need of regeneration (a site other than a site in need of regeneration). Accordingly, "a tissue other than a tissue in need of regeneration" can also be referred to as:
a site other than a tissue in need of regeneration; a site other than a site in need of regeneration; a site distant from a tissue in need of regeneration; a site distant from a site in need of regeneration; a site distal to a site in need of regeneration; a tissue distal to a tissue in need of regeneration; a distal site; or a distal tissue.

In particular, the agents of the present invention are effectively used to regenerate tissues (brain, heart, etc.) to which it is difficult to directly administer pharmaceutical agents from outside of the body.

Bone marrow-derived cells recruited to a tissue in need of regeneration differentiate into various types of cells to contribute to functional regeneration of the tissue in need of regeneration and maintenance/enhancement of the functions. In the present invention, examples of tissue in need of regeneration include, but are not limited to, tissues damaged by various pathological conditions due to ischemic/hypoperfusive/hypoxic conditions, trauma, burns, inflammation, autoimmunity, gene abnormalities, and the like.

Tissues in the present invention are not particularly limited as long as they are tissues into which bone marrow-derived cells can differentiate. Examples include all types of tissues in the living body, such as skin tissue, bone tissue, cartilage tissue, muscle tissue, adipose tissue, cardiac muscle tissue, neurological tissue, pulmonary tissue, gastrointestinal tissues, hepatic/biliary/pancreatic tissues, and genitourinary organs. Moreover, with use of the above tissue regeneration-promoting agents, treatments for inducing functional tissue regeneration becomes possible not only in cutaneous diseases such as intractable cutaneous ulcers, skin wounds, bullosis, and alopecia, but also in tissues in need of regeneration such as cerebral infarction, myocardial infarction, bone fracture, pulmonary infarction, gastric ulcers, and enteritis. Animal species to be administered with the above tissue regeneration-promoting agent are not particularly limited, and include mammals, birds, fish, and such. Mammals include human and non-human animals, which can be exemplified by, but are not limited to, humans, mice, rats, monkeys, pigs, dogs, rabbits, hamsters, guinea pigs, horses, sheep, and whales.

Examples of the tissue other than a tissue in need of regeneration include blood tissues, muscle tissues, subcutaneous tissues, intradermal tissues, abdominal cavity, and such.

Accordingly, the agents of the present invention include agents for promoting the regeneration of the above-described tissues.

The agents of the present invention preferably include agents for promoting the regeneration of nerve tissues, bone tissues, and skin tissues, but are not limited thereto. Such nerve tissue regeneration-promoting agents include agents for promoting regeneration of tissues of the central nervous system, but are not limited thereto. Nerve tissue regeneration-promoting agents can also be used to treat, for example, without limitation, cerebral infarction, brain hemorrhage, and brain contusion. Furthermore, bone tissue regeneration-promoting agents can be used to treat, for example, without limitation, bone fracture. In addition, skin tissue regeneration-promoting agents can be used to treat, for example, without limitation, skin ulcers, insufficient suture closure of surgical wounds, burns, cuts, bruises, skin erosions, and abrasions.

Herein, "bone marrow cells" and "bone marrow-derived cells" are cells other than hematopoietic stem cells, or cells derived therefrom such as leukocytes, erythrocytes, and platelets, and are stem cells represented by cells which have been hitherto called bone marrow mesenchymal stem cells, bone marrow stromal pluripotent stem cells, or bone marrow pluripotent stem cells. "Bone marrow cells" include cells containing tissue progenitor cell populations existing in the bone marrow. "Bone marrow cells" and "bone marrow-derived cells can be isolated by bone marrow collection (bone marrow cell collection) or peripheral blood collection. Hematopoietic stem cells are nonadherent, while some of the "bone marrow cells" and "bone marrow-derived cells" are obtained as adherent cells by means of a cell culture of a monocyte fraction of blood obtained by the bone marrow collection (bone marrow cell collection) or peripheral blood collection. Moreover, "bone marrow cells" and "bone marrow-derived cells" include mesenchymal stem cells, and have a potential to differentiate into, preferably, osteoblasts (the induction of differentiation can be identified by observing calcification), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. The cells to be differentiated into are not limited to the above cells, and the potential to differentiate into cells of parenchymatous organs such as liver, kidney, and pancreas is also included.

Herein, "bone marrow cells" refer to cells existing within the bone marrow, while "bone-marrow derived cells" refer to "bone marrow cells" recruited outside the bone marrow.

Herein, "bone marrow mesenchymal stem cells", "bone marrow stromal pluripotent cells" or "bone marrow pluripotent stem cells" refer to cells existing in the bone marrow, which are directly collected from the bone marrow or indirectly collected from other tissues (blood, skin, fat, and other tissues), and can be cultured and proliferated as adherent cells on a culture dish (made of plastic or glass). These cells are characterized in having a potential to differentiate into mesenchymal tissues such as bone, cartilage, and fat (mesenchymal stem cells), or into skeletal muscle, heart muscle, nervous tissues, and epithelial tissues (pluripotent stem cells), and can be obtained by collection of bone marrow cells. "Bone marrow mesenchymal stem cells", "bone marrow stromal pluripotent cells", or "bone marrow pluripotent stem cells" recruited from bone marrow are cells that can be obtained by collection from peripheral blood, mesenchymal tissues such as fat, epithelial tissues such as skin, or nervous tissues such as brain. Bone marrow mesenchymal stem cells, bone marrow stromal pluripotent stem cells, bone marrow pluripotent stem cells, or these cells recruited from bone marrow are also characterized in having a potential to differentiate into epithelial tissues such as keratinocytes that constitute skin, or nervous tissues that constitute brain, when administered to a lesion area of the living body immediately after collection or after once being adhered onto a culture dish. Examples of bone marrow mesenchymal stem cells, bone marrow stromal pluripotent stem cells, bone marrow pluripotent stem cells, or these cells recruited from bone marrow, include cells having the property of CD11b negative, but are not limited thereto.

Bone marrow mesenchymal stem cells, bone marrow stromal pluripotent stem cells, bone marrow pluripotent stem cells, or these cells recruited from bone marrow preferably have a potency to differentiate into: osteoblasts (the induction of differentiation can be identified by observing calcification), chondrocytes (which can be identified by alcian blue positive staining, safranin O positive staining, or the like), adipocytes (which can be identified by Sudan III positive staining), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further preferably into cells of parenchymatous organs such as liver, kidney, and pancreas. However, differentiated cells are not limited to the above cells.

Moreover, human bone marrow mesenchymal stem cells, bone marrow stromal pluripotent stem cells, bone marrow pluripotent stem cells, or these cells recruited from bone marrow can be exemplified by, but are not limited to, cells which can be directly obtained by collecting bone marrow (cells), peripheral blood, or fat, or obtained as adherent cells through culturing of an isolated monocyte fraction. Markers for human bone marrow mesenchymal stem cells, bone marrow stromal pluripotent stem cells, bone marrow pluripotent stem cells or these cells recruited from bone marrow can be, for example, all or some of the following but are not limited thereto: Lin-negative, CD45-negative, CD44-positive, CD90-positive, and CD29-positive.

Moreover, mouse bone marrow mesenchymal stem cells, bone marrow stromal pluripotent stem cells, bone marrow pluripotent stem cells, or these cells recruited from bone marrow can be exemplified by, but are not limited to, cells which can be obtained by methods described in the Examples. Markers for mouse bone marrow mesenchymal stem cells, bone marrow stromal pluripotent stem cells, bone marrow pluripotent stem cells, or these cells recruited from bone marrow can be for example, all or some of the following but are not limited thereto: CD44-positive, PDGFRα-positive, PDGFRβ-positive, CD45-negative, Lin-negative, Sca-1 positive, c-kit negative, CD90-positive, and CD29-positive.

Tissue progenitor cells are defined as undifferentiated cells having a unidirectional potency to differentiate into cells of a specific tissue other than the blood system, and include undifferentiated cells having the potency to differentiate into mesenchymal tissues, epithelial tissues, nerve tissues, parenchymatous organs, and vascular endothelium as mentioned above.

For tissue regeneration-promoting agents of the present invention, there is no particular limitation in substances other than at least one of the substances (a) to (q) mentioned above, so long as they do not inhibit the attraction of bone marrow-derived cells and the promotion of tissue regeneration. For example, in addition to at least one of the substances (a) to (q) mentioned above, the tissue regeneration-promoting agents of the present invention may contain: related molecule(s) enhancing the function of substances (a) to (q) mentioned above to induce functional tissue regeneration; molecule(s) which inhibit unanticipated actions of substances (a) to (q) mentioned above; factors which regulate proliferation and differentiation of bone marrow-derived cells; and other factors which enhance/maintain these factors or cellular functions.

Animal species which serve as a source of the HMGB1, HMGB2, HMGB3, S100A8, or S100A9 protein, the extract mentioned above, or the heparin binding fraction mentioned above for the tissue regeneration-promoting agents of the present invention, include human and non-human animals, such as humans, mice, rats, monkeys, pigs, dogs, rabbits, hamsters, and guinea pigs, but are preferably the same as the animal species to be administered with the substances and the like.

The HMGB1 protein of the present invention can be exemplified by, but is not limited to proteins comprising the amino acid sequence of SEQ ID NO: 1, 3, or 5. HMGB1 proteins of the present invention can also include proteins which are functionally equivalent to the protein comprising the amino acid sequence of SEQ ID NO: 1, 3, or 5. Examples of such proteins include: 1) isolated proteins which comprise an amino acid sequence with one or more amino acid substitutions, deletions, insertions, and/or additions in the amino acid sequence of SEQ ID NO: 1, 3, or 5, and which are functionally equivalent to the protein comprising the amino acid sequence of SEQ ID NO: 1, 3, or 5; and 2) isolated proteins which are encoded by DNAs that hybridize under stringent conditions with DNAs comprising the nucleotide sequence of SEQ ID NO: 2, 4, or 6, and which are functionally equivalent to the protein comprising the amino acid sequence of SEQ ID NO: 1, 3, or 5.

The HMGB2 protein of the present invention can be exemplified by, but is not limited to proteins comprising the amino acid sequence of SEQ ID NO: 7, 9, or 11. HMGB2 proteins of the present invention can also include proteins which are functionally equivalent to the protein comprising the amino acid sequence of SEQ ID NO: 7, 9, or 11. Examples of such proteins include: 1) isolated proteins which comprise an amino acid sequence with one or more amino acid substitutions, deletions, insertions, and/or additions in the amino acid sequence of SEQ ID NO: 7, 9, or 11, and which are functionally equivalent to the protein comprising the amino acid sequence of SEQ ID NO: 7, 9, or 11; and 2) isolated proteins which are encoded by DNAs that hybridize under stringent conditions with DNAs comprising the nucleotide sequence of SEQ ID NO: 8, 10, or 12, and which are functionally equivalent to the protein comprising the amino acid sequence of SEQ ID NO: 7, 9, or 11.

The HMGB3 protein of the present invention can be exemplified by, but is not limited to proteins comprising the amino acid sequence of SEQ ID NO: 13 or 15. HMGB3 proteins of the present invention can also include proteins which are functionally equivalent to the protein comprising the amino acid sequence of SEQ ID NO: 13 or 15. Examples of such proteins include: 1) isolated proteins which comprise an amino acid sequence with one or more amino acid substitutions, deletions, insertions, and/or additions in the amino acid sequence of SEQ ID NO: 13 or 15, and which are functionally equivalent to the protein comprising the amino acid sequence of SEQ ID NO: 13 or 15; and 2) isolated proteins which are encoded by DNAs that hybridize under stringent conditions with DNAs comprising the nucleotide sequence of SEQ ID NO: 14 or 16, and which are functionally equivalent to the protein comprising the amino acid sequence of SEQ ID NO: 13 or 15.

The S100A8 protein of the present invention can be exemplified by, but is not limited to proteins comprising the amino acid sequence of SEQ ID NO: 17, 19, or 21. S100A8 proteins of the present invention can also include proteins which are functionally equivalent to the protein comprising the amino acid sequence of SEQ ID NO: 17, 19, or 21. Examples of such proteins include: 1) isolated proteins which comprise an amino acid sequence with one or more amino acid substitutions, deletions, insertions, and/or additions in the amino acid sequence of SEQ ID NO: 17, 19, or 21, and which are functionally equivalent to the protein comprising the amino acid sequence of SEQ ID NO: 17, 19, or 21; and 2) isolated proteins which are encoded by DNAs that hybridize under stringent conditions with DNAs comprising the nucleotide sequence of SEQ ID NO: 18, 20, or 22, and which are functionally equivalent to the protein comprising the amino acid sequence of SEQ ID NO: 18, 20, or 22.

The S100A9 protein of the present invention can be exemplified by, but is not limited to, proteins comprising the amino acid sequence of SEQ ID NO: 23, 25, or 27. S100A9 proteins of the present invention can also include proteins which are functionally equivalent to the protein comprising the amino acid sequence of SEQ ID NO: 23, 25, or 27. Examples of such proteins include: 1) isolated proteins which comprise an amino acid sequence with one or more amino acid substitutions, deletions, insertions, and/or additions in the amino acid sequence of SEQ ID NO: 23, 25, or 27, and which are functionally equivalent to the protein comprising the amino acid sequence of SEQ ID NO: 23, 25, or 27; and 2) isolated proteins which are encoded by DNAs that hybridize under stringent conditions with DNAs comprising the nucleotide sequence of SEQ ID NO: 24, 26, or 28, and which are functionally equivalent to the protein comprising the amino acid sequence of SEQ ID NO: 23, 25, or 27.

Isolated proteins which are functionally equivalent to the protein comprising the amino acid sequence of SEQ ID NO: 1, 3, 5, 7, 9, 11, 13, 15, 17, 19, 21, 23, 25, or 27 may be homologues or paralogues to the protein comprising the amino acid sequence of SEQ ID NO: 1, 3, 5, 7, 9, 11, 13, 15, 17, 19, 21, 23, 25, or 27. Those skilled in the art can isolate proteins which are functionally equivalent to the protein comprising the amino acid sequence of SEQ ID NO: 1, 3, 5, 7, 9, 11, 13, 15, 17, 19, 21, 23, 25, or 27, by known methods (supplementary volume of "Jikken Igaku (Experimental Medicine), Idenshi Kougaku Handbook (Genetic Engineering Handbook)", pp 246-251, published by Yodosha Co., Ltd., 1991).

Examples of proteins which are functionally equivalent to the protein comprising the amino acid sequence of SEQ ID NO: 1, 3, 5, 7, 9, 11, 13, 15, 17, 19, 21, 23, 25, or 27 include proteins having activity of recruiting bone marrow-derived cells into tissues in need of regeneration, or activity of migrating bone marrow-derived cells.

Proteins which comprise an amino acid sequence with one or more amino acid substitutions, deletions, insertions, and/or additions in the amino acid sequence of SEQ ID NO: 1, 3, 5, 7, 9, 11, 13, 15, 17, 19, 21, 23, 25, or 27, and which are functionally equivalent to the protein comprising the amino acid sequence of SEQ ID NO: 1, 3, 5, 7, 9, 11, 13, 15, 17, 19, 21, 23, 25, or 27 include naturally-occurring proteins. Generally, eukaryotic genes have polymorphism as known in interferon genes and such. Alterations in nucleotide sequence caused by the polymorphism may result in one or more amino acid substitutions, deletions, insertions, and/or additions. Naturally-occurring proteins such as those comprising an amino acid sequence with one or more amino acid substitutions, deletions, insertions, and/or additions in the amino acid sequence of SEQ ID NO: 1, 3, 5, 7, 9, 11, 13, 15, 17, 19, 21, 23, 25, or 27, and which are functionally equivalent to the protein comprising the amino acid sequence of SEQ ID NO: 1, 3, 5, 7, 9, 11, 13, 15, 17, 19, 21, 23, 25, or 27 are included in HMGB1, HMGB2, HMGB3, S100A8, or S100A9 proteins of the present invention.

The present invention also includes artificially-produced mutant proteins as long as they are functionally equivalent to the protein comprising the amino acid sequence of SEQ ID NO: 1, 3, 5, 7, 9, 11, 13, 15, 17, 19, 21, 23, 25, or 27. Known methods which cause random mutations to a given nucleotide sequence include substitution(s) of base pair(s) through nitrous acid treatment of DNA (Hirose, S. et al., Proc. Natl. Acad. Sci. USA., 79: 7258-7260, 1982). This method enables random introduction of substitution(s) of base pair(s) into a specific segment by nitrous acid treatment of the segment desired to be mutated. Alternatively, technologies for site-directing a target mutation include the gapped duplex method (Kramer W. and Fritz H J., Methods in Enzymol., 154: 350-367, 1987) and the like. A cyclic double stranded vector in which a gene to be introduced with a mutation is cloned, is separated into single strands. These single strands are hybridized with a synthetic oligonucleotide mutated at the target site. A vector-derived complementary single strand DNA linearized by a restriction enzyme is annealed with the cyclic single stranded vector, and the gap between the oligonucleotide and the vector is filled by using a DNA polymerase, which is then made into a complete double stranded vector by ligation.

The number of amino acids to be modified would be typically 50 or less, preferably 30 or less, and more preferably 5 amino acids or less (for example, one amino acid).

When an amino acid is artificially substituted, substitution with an amino acid having similar properties would result in maintaining the activity of the original protein. Proteins of the present invention include proteins resulting from a conservative substitution in the above substitution of amino acid(s), and which are functionally equivalent to the protein comprising the amino acid sequence of SEQ ID NO: 1, 3, 5, 7, 9, 11, 13, 15, 17, 19, 21, 23, 25, or 27. Conservative substitution is considered important when substituting amino acid(s) of domains important for protein activities. Such a conservative substitution of amino acid(s) is well known to those skilled in the art.

Examples of amino acid groups suitable for conservative substitution include basic amino acids (such as lysine, arginine, and histidine), acidic amino acids (such as aspartic acid and glutamic acid), uncharged polar amino acids (such as glycine, asparagine, glutamine, serine, threonine, tyrosine, and cysteine), nonpolar amino acids (such as alanine, valine, leucine, isoleucine, proline, phenylalanine, methionine, and tryptophane), β branched amino acids (such as threonine, valine, and isoleucine), and aromatic amino acids (such as tyrosine, phenylalanine, tryptophane, and histidine).

Moreover, non-conservative substitution may increase protein activities (for example, constitutively activated proteins).

In addition, proteins which are functionally equivalent to the protein comprising the amino acid sequence of SEQ ID NO: 1, 3, 5, 7, 9, 11, 13, 15, 17, 19, 21, 23, 25, or 27 can be obtained by methods that utilize hybridization. That is to say, a DNA encoding HMGB1, HMGB2, HMGB3, S100A8, or S100A9 protein of the present invention as shown in the SEQ ID NO: 2, 4, 6, 8, 10, 12, 14, 16, 18, 20, 22, 24, 26, or 28 or a fragment thereof is used as a probe, and then DNAs that can hybridize to them are isolated. A hybridization reaction performed under stringent conditions leads to the selection of highly homologous DNA as a nucleotide sequence. This increases the chances of isolated proteins containing proteins that are functionally equivalent to the HMGB1, HMGB2, HMGB3, S100A8, or S100A9 protein. Examples of a highly homologous nucleotide sequence include those having 70% or more, and desirably. 90% or more identity.

In a specific example, the term "stringent conditions" refers to hybridization conditions with 6×SSC, 40% formamide at 25° C. and subsequent washing with 1×SSC at 55° C. The stringency depends on conditions such as salt concentration, formamide concentration, or temperature; however it is obvious for those skilled in the art to set these conditions so as to obtain necessary stringency.

With the use of hybridization, for example, DNAs encoding homologues of the HMGB1, HMGB2, HMGB3, S100A8, or S100A9 proteins other than those proteins comprising the amino acid sequence of SEQ ID NO: 1, 3, 5, 7, 9, 11, 13, 15, 17, 19, 21, 23, 25, or 27 can be isolated.

Proteins which are functionally equivalent to a protein comprising the amino acid sequence of SEQ ID NO: 1, 3, 5, 7, 9, 11, 13, 15, 17, 19, 21, 23, 25, or 27 normally have a high homology with the amino acid sequence of SEQ ID NO: 1, 3, 5, 7, 9, 11, 13, 15, 17, 19, 21, 23, 25, or 27. The term "high homology" refers to a sequence identity of at least 30% or more, preferably 50% or more, more preferably 80% or more (for example, 95% or more). The identity of the nucleotide sequences and amino acid sequences can be determined using a homology search site via the internet (For example, homology searches such as FASTA, BLAST, PSI-BLAST, and SEARCH can be used in the DNA Data Bank of Japan (DDBJ) [examples of which include the homology search page (Search and Analysis) at the DNA Data Bank of Japan (DDBJ) website; http://www.ddbj.nig.ac.jp/E-mail/homology-j.html]). Furthermore, searches using BLAST can be carried out through the web site of the National Center for Biotechnology Information (NCBI) (examples of which include BLAST page at the homepage of NCBI website; http://www.ncbi.nlm.nih.gov/BLAST7; Altschul, S. F. et al., J. Mol. Biol., 1990, 215(3): 403-10; Altschul, S. F. & Gish, W., Meth. Enzymol., 1996, 266: 460-480; Altschul, S. F. et al., Nucleic Acids Res., 1997, 25: 3389-3402)).

For example, in the calculation of the identity of amino acid sequences using Advanced BLAST 2.1, the identity value (%) can be obtained by the following: blastp is used as the program, expect value is set at 10, all filters are set at OFF, BLOSUM62 is used for matrix, and gap existence cost, per residue gap cost, and lambda ratio are set at 11, 1, and 0.85, respectively (default parameters) (Karlin, S, and S. F. Altschul (1990) Proc. Natl. Acad. Sci. USA 87: 2264-68; Karlin, S, and S. F. Altschul (1993) Proc. Natl. Acad. Sci. USA 90: 5873-7).

In addition, proteins functionally equivalent to a protein comprising the amino acid sequence of SEQ ID NO: 1, 3, 5, 7, 9, 11, 13, 15, 17, 19, 21, 23, 25, or 27 may be fragments of the amino acid sequence of SEQ ID NO: 1, 3, 5, 7, 9, 11, 13, 15, 17, 19, 21, 23, 25, or 27.

Proteins of the present invention, or proteins functionally equivalent thereto may be proteins subjected to various modifications such as physiological modification with sugar chains and the like, labeling with fluorescence or radioactive substances, or fusion with other proteins. Particularly in recombinants that will be described later, sugar chain modification may vary depending on the hosts used for expression. However, even if there is a difference in sugar chain modifications, all proteins having properties similar to those of HMGB1, HMGB2, HMGB3, S100A8, or S100A9 proteins disclosed herein are HMGB1, HMGB2, HMGB3, S100A8, or S100A9 proteins of the present invention or proteins functionally equivalent thereto.

HMGB1, HMGB2, HMGB3, S100A8, or S100A9 proteins can be obtained not only from living materials, but also in the form of recombinants by incorporating genes that encode these proteins into an appropriate expression system. In order to obtain HMGB1, HMGB2, HMGB3, S100A8, or S100A9 proteins by genetic engineering techniques, the above-mentioned DNAs which encode HMGB1, HMGB2, HMGB3, S100A8, or S100A9 proteins may be incorporated into an appropriate expression system, and they can then be expressed. Examples of host/vector systems applicable to the present invention include the expression vector pGEX and E. coli. With pGEX, foreign genes can be expressed as a fusion protein with glutathione-S-transferase (GST) (Gene, 67: 31-40, 1988). pGEX incorporated with a gene encoding the HMGB1, HMGB2, HMGB3, S100A8, or S100A9 protein is introduced into an E. coli strain such as BL21 by heat shock, incubated for an appropriate time and then isopropylthio-β-D-galactoside (IPTG) is added to induce the expression of GST-fused HMGB1, GST-fused HMGB2, GST-fused HMGB3, GST-fused S100A8, or GST-fused S100A9 proteins. Since GST of the present invention adsorbs onto Glutathione Sepharose 4B, the expression product is readily separated and purified by affinity column chromatography.

In addition, the following may also be applied as host/vector systems to obtain recombinants of HMGB1, HMGB2, HMGB3, S100A8, or S100A9 proteins. First, when bacteria are used as hosts, expression vectors for fusion proteins that utilize histidine-tag, HA-tag, a FLAG-tag, and the like are commercially available. The recombinants of the present invention also include those to which a tag or a partial peptide thereof is attached.

Regarding yeasts, yeasts belonging to the genus *Pichia* are known to be effective for the expression of sugar chain-containing proteins. In terms of the addition of sugar chains, expression systems that utilize baculovirus vector with insect cells as a host are also useful (Bio/Technology, 6: 47-55, 1988). Further, using mammalian cells, transfection of a vector is carried out using promoters such as CMV, RSV, and SV40. Any of these host/vector systems can be used as an expression system of HMGB1, HMGB2, HMGB3, S100A8, or S100A9 proteins. Moreover, genes can also be introduced using viral vectors such as retrovirus vectors, adenovirus vectors, and adeno-associated virus vectors.

Thus obtained proteins of the present invention may be isolated intracellularly or extracellularly (medium and such), and can be purified as proteins that are substantially pure and homogenous. Proteins may be separated and purified using separation and purification methods which are commonly used in protein purification, and are not particularly limited. For example, proteins can be separated and purified by appropriately selecting and combining a chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Examples of chromatographies include affinity chromatography, ion-exchange chromatography, hydrophobic chromatoaraphy, gel filtration, reverse phase chromatography, and adsorption chromatography (Marshak et al., Strategies for Protein Purification and Characterization: A Laboratory Course Manual. Ed Daniel R. Cold Spring Harbor Laboratory Press, 1996). These chromatographies can be performed using liquid phase chromatographies such as HPLC and FPLC.

Moreover, proteins of the present invention are preferably substantially purified proteins. Here, the term "substantially purified" means that the protein purity of the present invention (proportion of the protein of the present invention in total protein components) is 50% or more, 60% or more, 70% or more, 80% or more, 90% or more, 95% or more, 100% or close to 100%. The upper limit for "close to 100%" depends on the purification techniques and analytical techniques of those skilled in the art, of which examples are 99.999%, 99.99%, 99.9%, 99%, and the like.

Moreover, a substantially purified protein includes any protein purified by any purification method as long as the protein purity is as mentioned above. Examples include, but are not limited to, proteins substantially purified by appropriately selecting and combining the above-mentioned chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Cells where HMGB1, HMGB2, HMGB3, S100A8, or S100A9 proteins of the present invention are released or secreted basically include all types of tissue-derived cells in vivo. Cells which can be readily collected and cultured are exemplified by, but are not limited to, fibroblasts (such as normal skin fibroblasts and cell lines derived therefrom). Moreover, cells secreting HMGB), HMGB2, HMGB3, S100A8, or S100A9 proteins can also be produced by the following manner. A vector is produced by inserting an HMGB1, HMGB2, HMGB3, S100A8, or S100A9 protein-encoding DNA, or an HMGB1, HMGB2, HMGB3, S100A8, or S100A9 protein-encoding DNA linked with a secretion signal-encoding DNA (ATG CAG ACA GAC ACA CTC CTG CTA TGG GTA CTG CTG CTG TGG GTT CCA GGT TCC ACT GGT GAC; SEQ ID NO: 29), into a known expression vector or a gene therapy vector. The produced vector is introduced into mammalian cells such as fibroblasts (such as normal skin fibroblasts and cell lines derived therefrom), insect cells, and other cells. Examples of secretion signal-encoding DNAs include, but are not limited to, DNAs with the above-described sequences. Furthermore, there are no particular limitations in the animal type from which these cells derive, although cells from the animal type of the target animal subjected to vector administration, cells from the target itself, or cells derived from a blood relative of the target subjected to vector administration are preferably used.

DNAs which encode HMGB1, HMGB2, HMGB3, S100A8, or S100A9 proteins of the inducers or tissue regeneration-promoting agents of the present invention may be cDNAs, genomic DNAs, natural DNAs, or artificially-synthesized DNAs so long as they encode the HMGB1, HMGB2, HMGB3, S100A8, or S100A9 protein. DNAs which encode HMGB HMGB2, HMGB3, S100A8, or S100A9 proteins are normally administered in a form inserted in vectors.

Examples of the vectors of the present invention include, but are not limited to, plasmid vectors, retrovirus vectors, lentivirus vectors, adenovirus vectors, adeno-associated virus vectors, Sendai virus vectors, Sendai virus envelope vectors, and papilloma virus vectors. The vectors may contain promoter DNA sequences which effectively induce gene expression, factors that regulate gene expression, and molecules which are necessary for maintaining DNA stability.

In the present invention, the following vectors may also be used: partial peptides of HMGB1, HMGB2, HMGB3, S100A8, or S100A9 protein which have an activity of recruiting bone marrow-derived cells; cells secreting these partial peptides; or vectors inserted with the DNAs encoding these partial peptides.

Extracts of cells or tissues used in the present invention can be produced by methods comprising the step of immersing cells or tissues in a solvent.

Cells and tissues to be immersed in a solvent are not particularly limited, but include, for example, tissue-derived cells, cells of cell lines established from tissue-derived cells (including, but not limited to, for example, HeLa and HEK293), isolated cells, non-isolated cells (for example, cells in isolated tissues), and cells transfected with DNA encoding HMGB1, HMGB2, HMGB3, S100A8, or S100A9 protein. The above tissues may be any types of tissue, and include, but are not limited to, for example, live skin tissues and tissues obtained by internal biopsy (surgery) (brain, lung, heart, liver, stomach, small and large intestines, pancreas, kidney, urinary bladder, spleen, uterus, testis, blood, etc.).

Examples of the above solvent include, but are not limited to, physiological saline, phosphate-buffered saline (PBS), and Tris-buffered saline (TBS). Moreover, the immersion time of cells or tissue in a solvent should be a duration necessary and sufficient for inducing cell necrosis, that is, 1 hour to 48 hours (such as 6 to 48 hours), and preferably 12 hours to 24 hours, but is not limited thereto. Therefore, the "step of immersing cells in a solvent" can be rephrased as a "step of immersing cells in a solvent for a duration necessary and sufficient for inducing necrosis" or "step of necrosing cells". Moreover, examples of the temperature for immersing cells or tissue in a solvent include, but are not limited to, 4° C. to 25° C. (such as 4° C. to 8° C.), and preferably 4° C. Further, examples of the pH for immersing cells or tissue in a solvent include, without limitation, pH 7 to 8, and preferably pH 7.5. Examples of the buffer include, without limitation, a phosphate buffer solution at a concentration of 10 mM to 50 mM, preferably 10 to 20 mM, but are not limited thereto.

Moreover, in the present invention, cells or tissues can be removed from a solvent containing them after they are immersed in the solvent. The method for removing cells or tissues from a solvent is not particularly limited as long as the method is well known to those skilled in the art. For example, cells or tissues can be removed from a solvent by centrifugation at a gravity acceleration of from 10 G to 100,000 G (for example, 440 G) at 4° C. to 25° C. (for example, 4° C.), followed by separation of the supernatant, but the removal method is not limited thereto. The supernatant can be used as an extract of cells or tissues.

The extracts of cells or tissues in the present invention include, for example, skin extract and peripheral blood mononuclear cell extract (peripheral blood extract), but are not limited thereto.

The peripheral blood extract is prepared by the following method: after collecting blood with a syringe or the like, the cells are frozen in a freezer or liquid nitrogen, on dry ice, or such, and then thawed at a temperature of 0° C. or higher. Then, to remove insoluble cellular components, the sample is centrifuged, for example, at a gravity of 10 to 100,000 G (for example, at 440 G) and 4° C. to 25° C. (for example, at 4° C.), and the resulting supernatant is collected. The insoluble cellular components can be removed from the solvent by the method described above. However, methods for removing insoluble cellular components are not limited to the above example. The resulting supernatant can be used as an extract of cells or tissues. Alternatively, instead of centrifugation, insoluble cellular components can be removed by filtration through a nitrocellulose filter with micropores of 0.45 or the like. Alternatively, collected peripheral blood may be allowed to stand for three to 48 hours at 4° C. to induce cell necrosis. The intracellular components can be released from peripheral blood cells by this treatment. Then, to remove insoluble cellular components from the solvent, the sample is centrifuged at a gravity of 10 to 100,000 G (for example, at 440 G), and the resulting supernatant is collected. The insoluble cellular components can be removed from the solvent by the method described above, but are not limited thereto. The resulting supernatant can be used as an extract of cells or tissues. Alternatively, instead of centrifugation, insoluble cellular components can be removed by filtration through a nitrocellulose filter with micro pores of 0.45 μm of the like.

Meanwhile, a method for preparing cell extract from peripheral mononuclear cells is as follows: peripheral whole blood is collected using a syringe or the like, and then diluted with PBS to a total volume of 4 ml. After 3 ml of Ficoll-Paque Plus (GE) is placed in a centrifuge tube, the diluted blood is overlaid thereon. Following 40 minutes of centrifugation at 400 G (18° C.), the middle layer containing mononuclear cells is collected in a new centrifuge tube, and 45 ml of PBS is added thereto. After 5 minutes of centrifugation at 800 G (18° C.), the supernatant is discarded, and 45 ml of PBS is added to the cells. Following 5 minutes of centrifugation at 800 G (18° C.), the supernatant is discarded, and 200 μl of PBS is added to suspend the precipitated cells. The cell suspension is frozen for 30 minutes at −80° C. in a freezer, and then taken out of the freezer and thawed on ice. This freeze-thaw treatment is repeated three times, and the suspension is centrifuged at 800 G (4° C.) for 15 minutes to collect the supernatant. Instead of freezing, the cells can be placed in a refrigerator at 4° C. for 3 to 48 hours to induce necrosis of the cells and release intracellular components. Alternatively, intracellular components can be released outside of the cells by disrupting them using sonication while cooling on ice. After any of these treatments to release the intracellular components outside of the cells, the sample is centrifuged at a gravitational acceleration of 440 G to 1,000,000 G, preferably 20,000 G to 100,000 G, and the supernatant is collected as a cell extract. Instead of centrifugation, the sample may be filtered through a 0.45-μm micropore nitrocellulose filter, cellulose acetate, or such to remove insoluble components and prepare a cell extract.

Heparin-binding fractions from the extracts of cells or tissues in the present invention can be produced by a method comprising the following steps.

(a) immersing a cell or tissue in a solvent;
(b) contacting an extract obtained by the step (a) with immobilized heparin; and
(c) eluting a heparin-binding fraction (may also be expressed as heparin-purified fraction or heparin-column purified fraction) from the immobilized heparin.

"Immobilized heparin" refers to heparin covalently bound to an insoluble carrier. Examples of the insoluble carrier include, but are not limited to, Sepharose beads (such as Sepharose 4B, Sepharose 6B and such: GE Healthcare). In the present invention, a commercially available immobilized heparin (Hitrap Heparin HP column: GE Healthcare) may also be used.

Examples of conditions for contacting an extract of cells or tissues with immobilized heparin include, but are not limited to, about pH 7 to 8 (preferably pH 7.5), and a salt concentration of 0 to 200 mM, and preferably about 100 to 200 mM. The time the extract is in contact with immobilized heparin is not specifically limited, but the contact is preferably retained for 5 minutes or more in view of sufficient adsorption of the heparin-binding fraction onto immobilized heparin. Examples of the temperature include, but are not limited to, 4 to 8° C., and preferably 4° C. Further, examples of the elution condition of the heparin-binding fraction adsorbed onto the immobilized heparin include, but are not limited to, a pH of about 7 to 8 and a salt concentration of 200 to 1,000 mM (preferably about 1,000 mM).

Methods for administering the tissue regeneration-promoting agents of the present invention include parenteral administration, more specifically include administration by injection, but are not limited thereto. In addition, methods for administering the tissue regeneration-promoting agents of the present invention are not particularly limited as long as they allow the tissue regeneration-promoting agents to enter the blood circulation without remaining at the administration site. The methods for administering the tissue regeneration-promoting agents of the present invention include, for example, intravascular administration (intraarterial administration, intravenous administration, etc), administration into blood, intramuscular administration, subcutaneous administration, intradermal administration, and intraperitoneal administration, but are not limited thereto.

The method of administration may be appropriately selected according to the age and the symptoms of the patient. When an HMGB1, HMGB2, HMGB3, S100A8, or S100A9 protein is administered, the dose per time of the protein can be selected within a range of 0.0000001 ma to 1000 mg per kg body weight of a patient. Alternatively, the dose can be selected within a range of 0.00001 mg to 100000 mg per body of patient, for example. When administering cells secreting HMGB1, HMGB2, HMGB3, S100A8, or S100A9 protein or gene therapy vectors inserted with DNAs encoding HMGB1, HMGB2, HMGB3, S100A8, or S100A9 proteins they may be administered such that the amounts of HMGB1, HMGB2, HMGB3, S100A8, or S100A9 protein in the tissues in need of regeneration are within the above range. However, the dosage of the tissue regeneration-promoting agents of the present invention are not limited thereto.

Tissue regeneration-promoting agents of the present invention can be formulated according to the usual methods (for example, Remington's Pharmaceutical Science, latest edition, Mark Publishing Company, Easton, U.S.A), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

The present invention also provides kits for promoting tissue regeneration comprising a composition containing a substance of any one of (a) to (q) described below, wherein the composition is administered to a tissue other than a tissue in need of regeneration:
(a) an HMGB1 protein;
(b) a cell that secretes an HMGB1 protein;
(c) a vector into which a DNA encoding an HMGB1 protein is inserted;
(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;
(o) a vector into which a DNA encoding an S100A9 protein is inserted;
(p) a cell or tissue extract; and
(q) a heparin-binding fraction of a cell or tissue extract;

The kits for promoting tissue regeneration are characterized in that, when administered to a tissue other than a tissue in need of regeneration, they recruit bone marrow cells from the bone marrow to the tissue in need of regeneration via the peripheral circulation.

The kits of the present invention also include kits for treating tissues in need of regeneration as mentioned above. The kits of the present invention preferably include kits for parenteral administration, more preferably kits for administration by injection. The kits of the present invention also preferably include kits for intravascular, intramuscular, subcutaneous, intradermal, or intraperitoneal administration.

Furthermore, the kits of the present invention preferably include kits used for promoting regeneration of nerve, bone, or skin tissues.

The kits for promoting tissue regeneration include, for example, those containing: (1) the above-described substance dissolved in fibrinogen and (2) thrombin; or (1) the above-described substance, (2) fibrinogen, and (3) thrombin.

In the present invention, it is possible to use commercially-available fibrinogen and thrombin, including, for example, fibrinogen HT-Wf (Benesis-Mitsubishi Pharma), Beriplast (ZLB Behring), Tisseel (Baxter), Bolheal (KAKET-SUKEN), and TachoComb (ZLB Behring); however, they are not limited to these examples.

Meanwhile, the use of the above-described cell extract or tissue extract; heparin-binding fraction of the cell extract or tissue extract; HMGB1, HMGB2, HMGB3, S100A8, or S100A9 protein; cells expressing the HMGB1, HMGB2, HMGB3, S100A8, or S100A9 protein; vector inserted with a DNA encoding the HMGB1, HMGB2, HMGB3, S100A8, or S100A9 protein; partial peptide of the HMGB1, HMGB2, HMGB3, S100A8, or S100A9 protein; cell expressing the partial peptide; or vector inserted with a DNA encoding the partial peptide, may be referred to as follows:

(1) a method for promoting tissue regeneration, which comprises the step of administering an effective amount of a composition containing the substance of any one of (a) to (q) below to a tissue other than a tissue in need of regeneration:
(a) an HMGB1 protein;
(b) a cell that secretes an HMGB1 protein;
(c) a vector into which a DNA encoding an HMGB1 protein is inserted;
(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;
(o) a vector into which a DNA encoding an S100A9 protein is inserted;
(p) a cell or tissue extract; and
(q) a heparin-binding fraction of a cell or tissue extract;
(2) use of a composition containing the substance of any one of (a) to (q) below in producing a tissue regeneration-promoting agent, wherein the tissue regeneration-promoting agent is administered to a tissue other than a tissue in need of regeneration:
(a) an HMGB1 protein;
(b) a cell that secretes an HMGB1 protein;
(c) a vector into which a DNA encoding an HMGB1 protein is inserted;
(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;

(o) a vector into which a DNA encoding an S100A9 protein is inserted;
(p) a cell or tissue extract; and
(q) a heparin-binding fraction of a cell or tissue extract;
(3) a composition for use in a method for promoting tissue regeneration, which contains the substance of any one of (a) to (q) below and is administered to a tissue other than a tissue in need of regeneration:
(a) an HMGB1 protein;
(b) a cell that secretes an HMGB1 protein;
(c) a vector into which a DNA encoding an HMGB1 protein is inserted;
(d) an HMGB2 protein
(e) a cell that secretes an HMGB2 protein;
(f) a vector into which a DNA encoding an HMGB2 protein is inserted;
(g) an HMGB3 protein;
(h) a cell that secretes an HMGB3 protein;
(i) a vector into which a DNA encoding an HMGB3 protein is inserted;
(j) an S100A8 protein;
(k) a cell that secretes an S100A8 protein;
(l) a vector into which a DNA encoding an S100A8 protein is inserted;
(m) an S100A9 protein;
(n) a cell that secretes an S100A9 protein;
(o) a vector into which a DNA encoding an S100A9 protein is inserted;
(p) a cell or tissue extract; and
(q) a heparin-binding fraction of a cell or tissue extract.
All prior art documents cited herein are incorporated herein by reference.

Example 1

Purification of HMGB-1 and S100A8

RNA was extracted from newborn mouse skin using Trizol (Invitrogen), and then cDNA was synthesized using SuperScript III cDNA synthesis kit (Invitrogen). Using this cDNA as a template, HMGB1 cDNA was amplified by polymerase chain reaction (PCR). The resulting cDNA was inserted into pCAGGS, a plasmid vector for protein expression in mammalian cells, such that the vector would express the protein attached with GST tag and 6×His tag sequences at the N terminus of its amino acid sequence for the convenience of purification.

pCAGGS-Flag-His-S100A8 was transfected into a human fetal kidney cell-derived cultured cell line HEK 293 using polyethyleneimine (PEI). After 48 hours, the cells and culture supernatant were separately collected by centrifugation at 4,400 G at 4° C. for five minutes. Then, the collected supernatant was filtered through a cellulose acetate filter having pores with a diameter of 0.8 µm and then through a nitrocellulose filter having pores with a diameter of 0.45 µm to prepare a sample removed of insoluble fractions. The sample was loaded onto 5-ml HisTrap FF (GE) equilibrated with 50 ml of 50 mM Tris HCl (pH 8.0) containing 50 mM NaCl, and then the absorbed components were washed with 50 mM Tris HCl (pH 8.0) containing 50 mM NaCl and 10 mM imidazole to remove nonspecifically adsorbed components. The specifically adsorbed components were eluted from the column using 50 mM Tris HCl (pH 8.0) containing 50 mM NaCl and 100 mM imidazole. The adsorbed fractions were fractionated into silicone-coated plastic tubes (500 µl/tube). Protein-containing fractions were combined together, and then imidazole was removed using a desalting column PD10 (GE). The fractions were eluted using 50 mM Tris HCl (pH. 7.5) containing 150 mM NaCl. HRV3C (Novagen) was added to the eluted samples and the mixture was incubated at 4° C. for eight hours. After cleavage, the sample was loaded onto a 1-ml HiTrap Heparin column (GE) equilibrated with 50 mM Tris HCl (pH 7.5) containing 150 mM NaCl. The inside of the column was washed with 50 mM Tris HCl (pH 7.5) containing 150 mM NaCl. The protein bound to the column was eluted with 50 mM Tris HCl (pH 7.5) containing 1,000 mM NaCl. The eluted sample was diluted 50 times with 50 mM Tris HCl (pH 8.8) containing 20 mM NaCl, and adsorbed onto 1 mL of HiTrap 0 FF (GE) equilibrated with the same buffer. The adsorbed protein was eluted with 50 mM Tris HCl (pH 8.8) containing 500 mM NaCl while gradually increasing the concentration of NaCl. The presence of protein bound to the nickel column, heparin column, and Q column was confirmed by SDS-PAGE followed by Coomassie brilliant blue staining.

Figure 1:
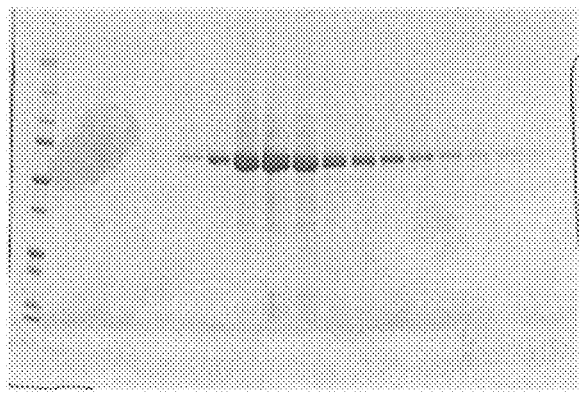
FIG. 1 is a set of photographs showing the process of purifying HMGB1. HEK293 was transfected with an expression vector containing a GST-tag, 6×His-tag, and HRV3C cleavage sequence at the N terminus of HMGB1. The culture supernatant was loaded onto a nickel column, and the binding fraction was eluted with imidazole. The nickel column-bound fraction was treated with HRV3C to cleave the GST-tag and 6×His tag from HMGB1. The fraction was then allowed to bind to a heparin-affinity column, and eluted with sodium chloride. The heparin-binding fraction was loaded onto a Q column, and eluted with sodium chloride. To detect the degree of purification in each purification step, each column-binding fraction was subjected to SDS-PAGE followed by Coomassie staining.
Figure 1:
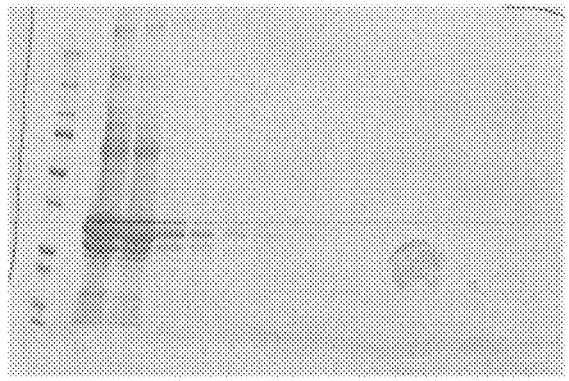
Figure 1:
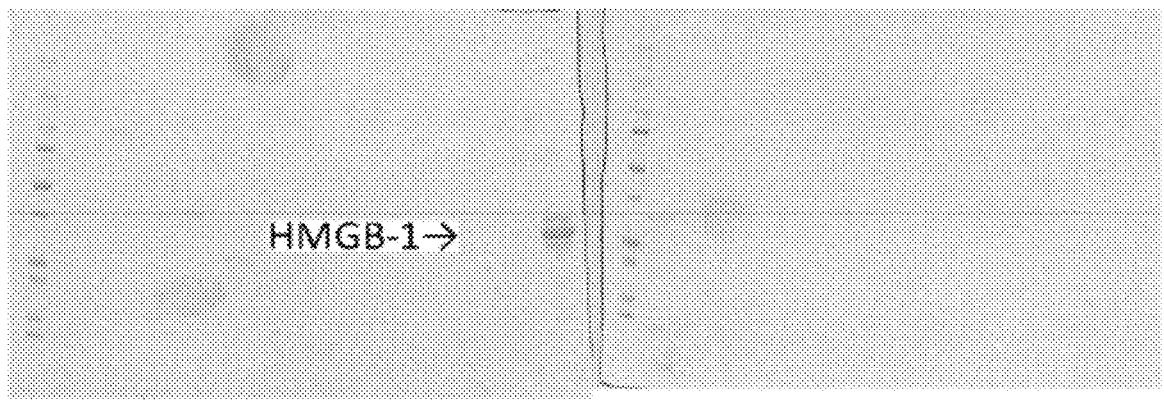

As a result, highly pure HMGB-1 was purified as shown in FIG. 1. In the following Examples, HMGB-1 prepared by this purification method was used.

Figure 39:
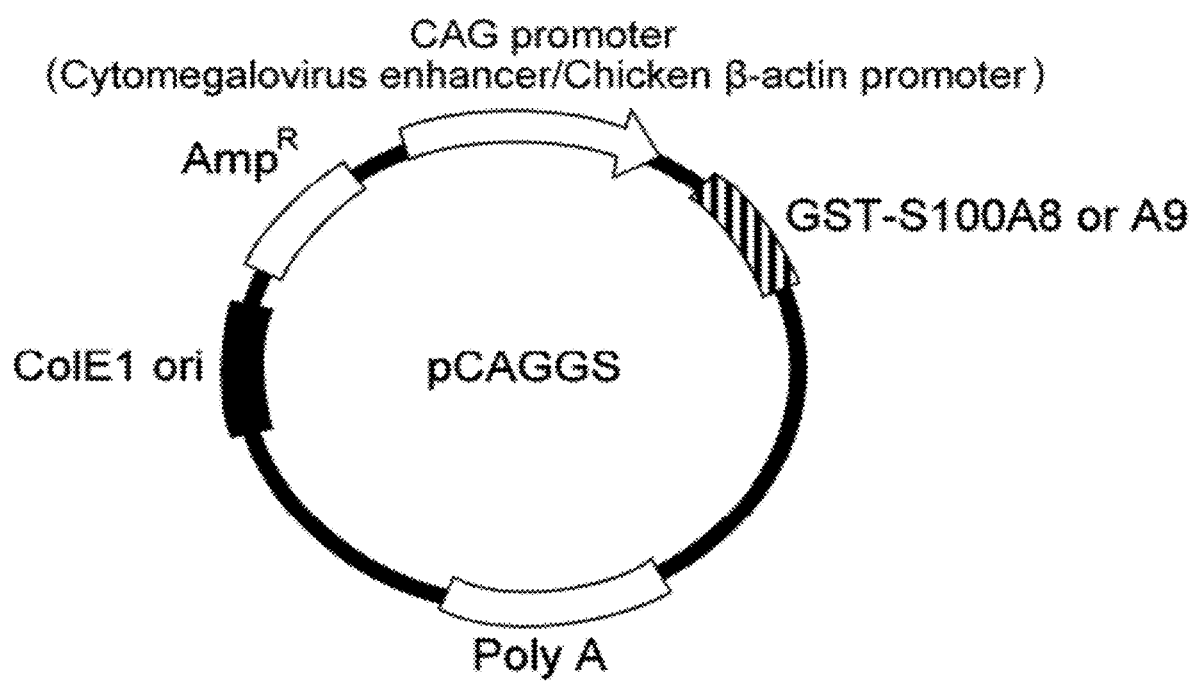
FIG. 39 shows in a diagram the expression vector for S100A8 or S100A9.

RNA was extracted from newborn mouse skin using Trizol (Invitrogen), and then cDNA was synthesized using SuperScript III cDNA synthesis kit (Invitrogen). Using this cDNA as a template, S100A8 cDNA was amplified by polymerase chain reaction (PCR). The resulting cDNA was inserted into pCAGGS, a plasmid vector for protein expression in mammalian cells, such that the vector would express the protein attached with a GST tag sequence (SEQ ID NO: 31 (amino acid sequence); SEQ ID NO: 32 (DNA sequence)) (FIG. 39).

Human fetal kidney cell-derived culture cell line HEK293 was transfected with pCAGGS-GST-S100A8 using a lipofection reagent (Invitrogen), and the cells and culture supernatant were collected after 48 hours. The cell and culture supernatant were centrifuged at 4400 g for 5 minutes at 4° C. to collect the supernatant (supernatant A) and cells separately. PBS containing 0.1% Tween 20 was added to the cells, and subjected to sonication for 30 seconds while on ice to disrupt the cell membrane. After centrifugation at 4400 g for 5 minutes at 4° C., the supernatant was collected (supernatant B). Supernatant A and B were combined together, and loaded onto HiTrap GST FF column (GE healthcare; 5 ml) in which the buffer had been replaced with 30 ml of PBS in advance. After loading, the column was washed with 100 ml of PBS, and the adsorbed protein was eluted with 20 mM phosphate buffer (pH 8) containing reduced glutathione. To remove glutathione, the buffer was replaced with PBS using gel filtration column PD-10 (GE).

Example 2

Effect of Intravenous Administration of HMGB-1 and S100A8 in Recruiting Bone Marrow-Derived Cells to Skin Ulceration Site During Skin Ulcer Healing Process Male C57BL/6 mice (6 weeks old) were irradiated at a lethal dose (10 Gy). Immediately; bone marrow cells ($5 \times 10^6$ cells/0.1 ml physiological phosphate buffer (pH 7.4)) derived from a green fluorescent protein (GFP) transgenic mouse (Okabe M. et al., FEBS Lett. 407, 313-319, 1997) were transplanted via the caudal vein. After 8 weeks, a round-shaped skin ulcer with a diameter of 6 mm was created on the back. To prevent shrinkage of the skin of the mice, a silicone ring with an outer diameter of 10 mm, inner diameter of 6 mm, and thickness of 1 mm was attached to the ulcer site using two-sided adhesive tape and medical adhesive Aron alpha A (Sankyo). The ulcer was covered with a silicone disc with a diameter of 10 mm and a thickness of 1 mm to prevent desiccation and bacterial infection at the ulcer. In addition, the ulcer was masked with Tegaderm (3M) for protection.

HMGB-1 (40 μg) or S100A8 (250 ng) was administered via the caudal vein five times at 24-hour intervals from the day of skin ulcer creation. Two weeks after the creation of skin ulcer, the mice were anesthetized by isoflurane inhalation, and then the degree of GFP fluorescence at the site of skin ulcer created on the back was observed using a fluorescent stereoscopic microscope. Then, the skin at the ulcer creation site was excised in a circular shape and fixed in PBS (phosphate buffer; Nacalai) containing 4% paraformaldehyde. After embedding in OCT compound, the skin was sliced into 8-μm sections using a microtome with a cooling apparatus (Leica). The sections were affixed onto glass slides. Then, the compound was washed off with PBS, and the nuclei were stained with DAPI. Next, the sections were washed with PBS to remove excess DAPI, and mounted with a mounting medium containing an anti-fading reagent. GFP fluorescence of each sample was detected using a fluorescent microscope.

Figure 2:
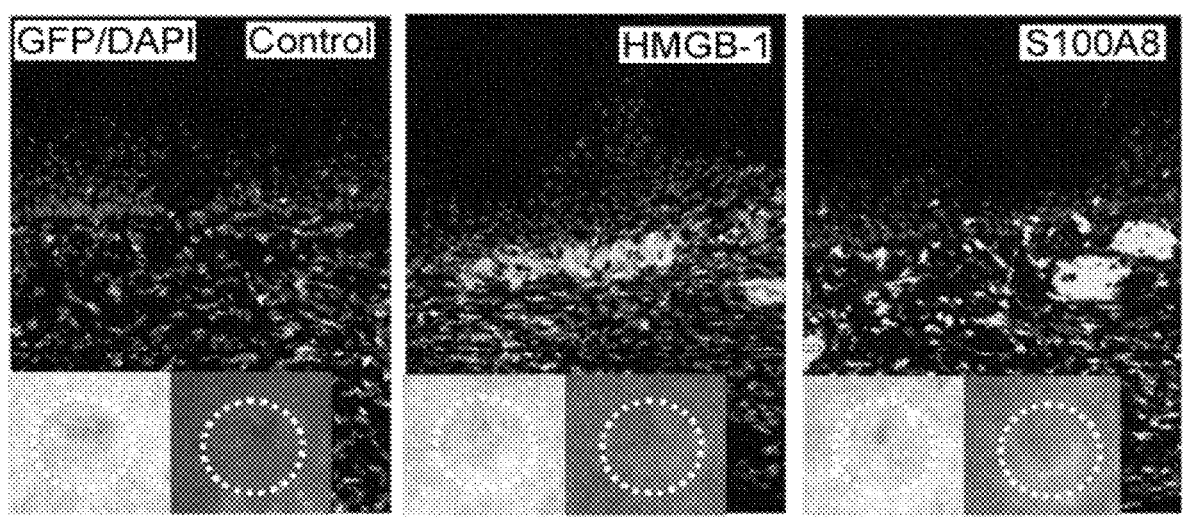
FIG. 2 is a set of photographs showing GFP signals in skin and skin thin sections after closure of ulcer. A skin ulcer was created on the back of GFP bone marrow-transplanted mice, and HMGB1 or S100A8 was intravenously administered to the mice. As compared to the control, many GFP-positive bone marrow-derived cells were detected on the skin of mice to which HMGB1 or S100A8 was intravenously administered.

The result is shown in FIG. 2. In the mice administered with HMGB-1 or S100A8, many bone marrow-derived cells (GFP-positive cells) as compared to the control were found to accumulate in the dermis, in particular in the upper layer, after closure of the skin ulcer.

Bone marrow pluripotent stem cells can differentiate into osteoblasts, chondrocytes, adipocytes, and others. In skin tissues, they are also believed to be able to differentiate into epidermal cells, hair follicle cells, dermal fibroblasts, and such. It has already been revealed that HMGB-1 and S100A8 have activity of recruiting bone marrow pluripotent stem cells and have a skin ulcer-reducing effect in mice when they are administered directly to a skin ulcer site. However, the present result has for the first time demonstrated that bone marrow-derived cells are recruited to the site of skin ulceration by administration of HMGB-1 and S100A8 into the venous blood, which is a non-target site and distant from the ulceration site.

Example 3

Effect of Intravenous Administration of HMGB-1 and S100A8 in Promoting Skin Ulcer Healing In male C57BL/6 mice (8 weeks old), a round-shaped skin ulcer with a diameter of 6 mm was created on the back. To prevent shrinkage of the skin of the mice, a silicone ring with an outer diameter of 10 mm, inner diameter of 6 mm, and thickness of 1 mm was attached to the ulcer site using two-sided adhesive tape and medical adhesive Aron alpha A (Sankyo). The ulcer was covered with a silicone disc with a diameter of 10 mm and a thickness of 1 mm to prevent desiccation and bacterial infection at the ulcer site. In addition, the ulcer was masked with Tegaderm (3M) for protection.

HMGB-1 (40 μg) or S100A8 (250 ng) was administered via the caudal vein five times at 24-hour intervals from the day of skin ulcer creation. The ulcer size was measured on days 3, 5, and 10 after creation of ulcer.

Figure 3:
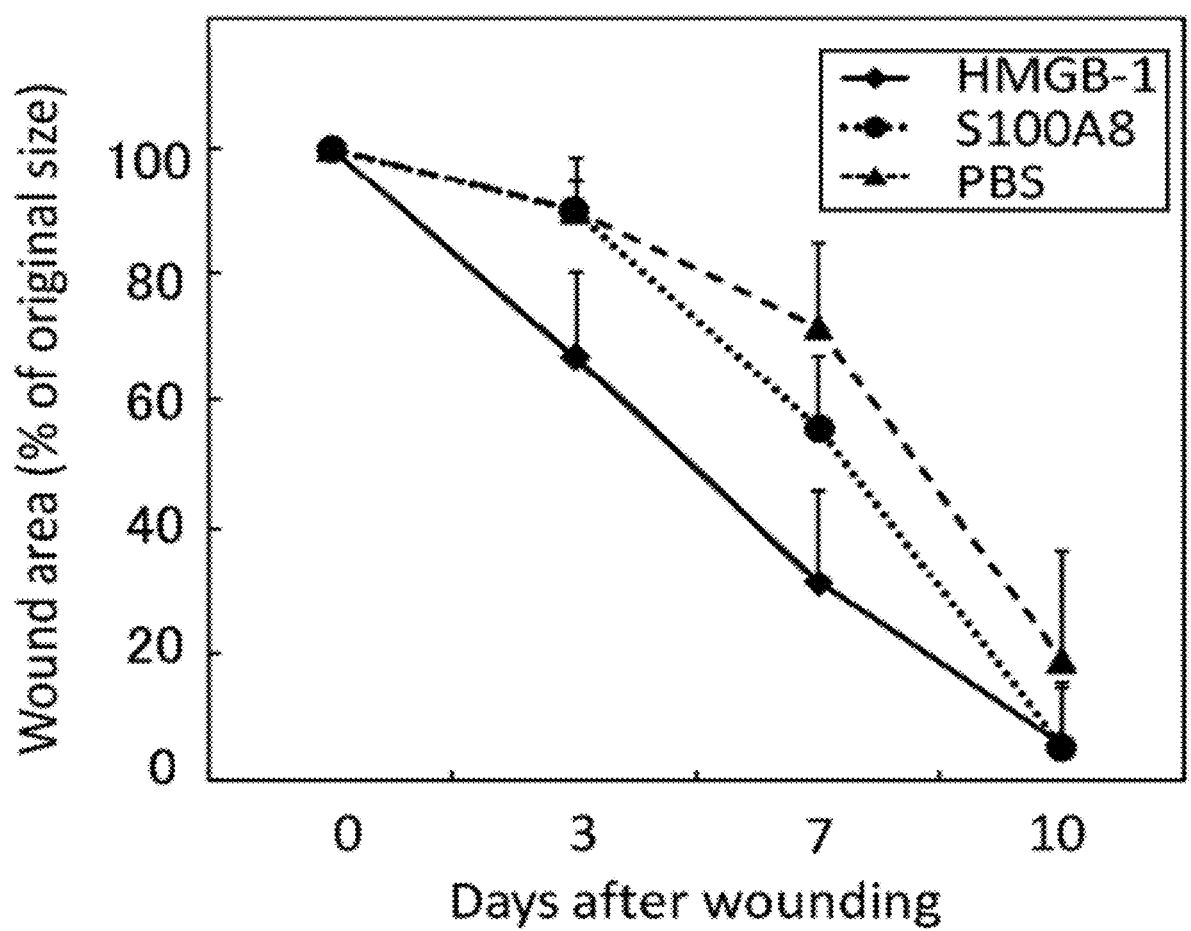
FIG. 3 is a graph showing the area of skin ulcer measured overtime. A skin ulcer was created on the back of mice, and HMGB1 or S100A8 was intravenously administered to the mice. After 3 days of the ulcer creation, the skin ulcer-reducing effect was observed in the HMGB1 administration group as compared to the control group. After 7 days of the ulcer creation, the skin ulcer-reducing effect was observed in the S100A8 administration group as compared to the control group (vertical axis, [ulcer area]/[ulcer area at the time of creation]×100; horizontal axis, days after ulcer creation).

The result is shown in FIG. 3. HMGB-1 reduced the ulcer size on day 3 after creation of ulcer as compared to the negative control (PBS administration). Meanwhile, S100A8 reduced the ulcer size on day 7 after creation of ulcer as compared to the negative control (PBS administration).

The skin ulcer healing-promoting effect has been conventionally achieved by administering HMGB-1 or S100A8 directly to a skin ulcer site. However, the present research for the first time succeeded in promoting the healing of a skin ulcer by administering HMGB-1 or S100A8 into a blood vessel, which was a non-target site and distant from the ulceration site. The present invention enables the treatment of skin ulcers without direct administration to the site of ulceration. Thus, it is possible to develop pharmaceutical agents that can be used even for conditions where the direct administration to the ulceration site is difficult, such as extensive skin ulcer, ulcer associated with skin loss, infected lesions, or necrotizing lesions, and such.

Example 4

Effect of Intravenous Administration of HMGB-1 in Promoting Scarless Healing of Skin Ulcer In male C57BL/6 mice (8 weeks old), a round-shaped skin ulcer with a diameter of 6 mm was created on the back. To prevent shrinkage of the skin of the mice, a silicone ring with an outer diameter of 10 mm, inner diameter of 6 mm, and thickness of 1 mm was attached to the ulcer site using two-sided adhesive tape and medical adhesive Aron alpha A (Sankyo). The ulcer was covered with a silicone disc with a diameter of 10 mm and a thickness of 1 mm to prevent desiccation and bacterial infection at the ulcer. In addition, the ulcer was masked with Tegaderm (3M) for protection.

HMGB-1 (40 μg) was administered via the caudal vein five times at 24-hour intervals from the day of skin ulcer creation. Four weeks after, creation of ulcer, the ulcer portion was sampled and fixed in 10% buffered formaldehyde. The samples were paraffin-embedded and then sliced into thin sections using a microtome. After deparaffinization, the sections were processed by hematoxylin-eosin (HE) staining and Masson's trichrome (MT) staining.

Figure 4:
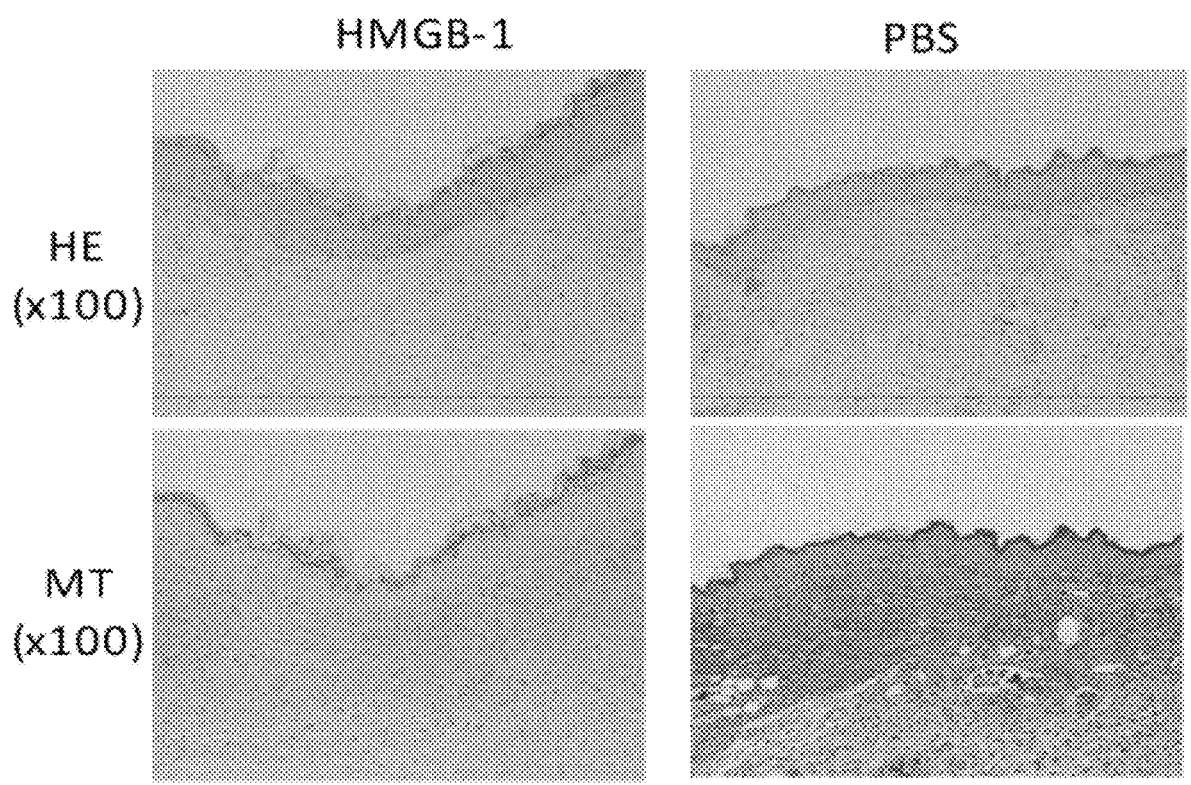
FIG. 4 is a set of photographs showing the results of hematoxylin-eosin staining (HE) and Masson's trichrome staining (MT) of thin skin sections after closure of skin ulcer. A skin ulcer was created on the back of mice, and HMGB1 was intravenously administered to the mice. An abnormal increase of collagen fiber was seen in the control mice, while such an abnormal increase of collagen fiber was suppressed in the mice to which HMGB1 was intravenously administered.

The result is shown in FIG. 4. In the skin of the HMGB-1-administered mice, an area strongly positive for Masson's trichrome staining as compared to the control mice (PBS administration) was seen in the upper layer of dermis.

It is known that in the process of skin ulcer healing, ulcer is closed by scar healing if the reconstruction of skin tissues is insufficient. Scar healing refers to the closure of ulcer with non-cellular components such as collagen fiber secreted by fibroblasts and the like. As scar has no functional tissue structure unlike normal tissues, it is associated with the hardening and shrinking of tissue even after healing. Thus, the suppression of scar formation is an important task from the functional and cosmetic point of view. The present result demonstrates that it is possible to promote the early closure and scarless healing of skin ulcers by administering HMGB-1 intravenously and thereby recruiting bone marrow-derived cells to the site of ulceration.

Example 5

Observation of Bone Marrow-Derived Cells in the Brain of Cerebral Infarction Model Animals Intravenously Administered with HMGB-1

Cerebral infarction was created in GFP-bone marrow-transplanted mice (an intraluminal filament model of middle cerebral artery occlusion). Specifically, GFP-bone marrow-transplanted mice produced by the method of the above-mentioned Example were anesthetized by isoflurane inhalation. Then, the head skin was opened, and the probe of a laser Doppler blood flowmeter was directly attached to the cranial bone to monitor the cerebral blood flow. Next, a median skin incision was made from the sternum to the lower jaw. The right common carotid artery was detached and ligated loosely with a #4 silk suture. The right external carotid artery was ligated at a distal position using a #6 silk suture. A puncture was made on the right external carotid artery at a proximal position while applying tension to the suture around the common carotid artery. A #6 monofilament nylon suture (intraluminal filament) with a tip of 700 μm shaped by heat was inserted at the puncture site. The filament was advanced toward the internal carotid artery until about 8 mm of the suture tip was inserted. Then, the suture around the common carotid artery was loosened. It was confirmed that the reading of the laser Doppler blood flowmeter was reduced by 10 times after the blockage of blood flow.

After 30 minutes of blood flow blockage, the intraluminal filament was withdrawn to restore the blood flow. After 12 hours, purified HMGB-1 (100 μg) diluted with 500 μl of PBS was administered to the prepared disease model mice from the caudal vein. HMGB-1 was then administered four times at 24-hour intervals in the same manner. Control mice were administered with PBS.

Two weeks after the last day of the treatment, perfusion fixation was carried out using 2% paraformaldehyde under isoflurane inhalation anesthesia. The brain was removed from the cranial bone, and dehydrated by immersion in 10% sucrose solution for 12 hours and then in 20% sucrose solution for 24 hours. After dehydration, the brain was placed in OTC compound, and frozen on dry ice to prepare a block. The block was sliced into 8-μm sections with a microtome for cryosectioning, and the sections were spread on silane-coated glass slides. After spreading, the sections were thoroughly dried, and washed with PBS to remove the compound.

PBS containing 2% skim milk was allowed to infiltrate the samples, and then an anti-mouse Nestin antibody and βIII tubulin antibody diluted 500 times with PBS containing 2% skim milk were allowed to infiltrate the samples at 4° C. for 8 hours. After thoroughly washing the samples with PBS for 5 minutes five times, a PE-labeled anti-rat IgG antibody diluted 500 times with PBS containing 2% skim milk was allowed to infiltrate the samples for one hour at room temperature. After thorough wash with PBS in the same manner, a DAPI solution was allowed to infiltrate the samples for 10 minutes at room temperature. Then, the samples were thoroughly washed with PBS. The samples were mounted with a mounting medium containing an anti-fading agent, and observed for GFP, DAPI, and PE fluorescence using a confocal laser microscope.

Figure 5:
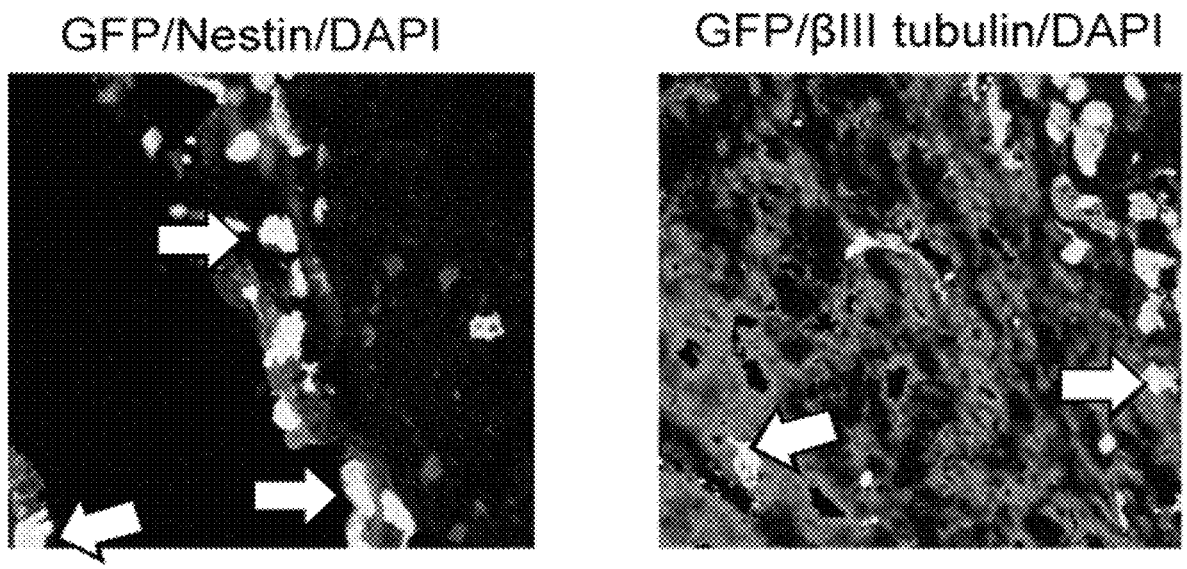
FIG. 5 is a set of photographs showing a result of detecting cells expressing Nestin (nerve stem cell marker) and β III tubulin (neuron marker). Cerebral infarction was created in GFP-bone marrow-transplanted mice, and then treated by intravenous administration of HMGB). After the treatment, thin brain sections were prepared and subjected to immunohistochemistry. In the left photograph, arrows indicate GFP-positive, Nestin-positive cells. In the right panel, arrows indicate GFP-positive, β III tubulin-positive cells. The bone marrow-derived cells were demonstrated to express neuron markers.

The result is shown in FIG. 5. In the brain of HMGB-1-administered mice, many bone marrow-derived cells (GFP-positive cells) were observed, and some bone marrow-derived cells were positive for Nestin (yellow cells in the right panel) as well as others were positive for βIII tubulin (yellow cells in the left panel). Bone marrow-derived cells were also observed in the PBS administration group; however, none of the cells expressed Nestin or βIII-tubulin (photographs not shown).

Bone marrow-derived cells are known to differentiate into nerve cells in vitro (in the culture system). Furthermore, bone marrow-derived cells in vivo (in the body) are known to express neuronal markers in the brain on rare occasions. However, it is not clear whether such bone marrow-derived cells have neurological functions in the brain. Meanwhile, non-inflammatory bone marrow cells such as bone marrow mesenchymal stein cells have been demonstrated to produce a therapeutic effect when administered in the pathological condition of cerebral infarction. However, the healing mechanism remains to be clarified.

The present result demonstrated that bone marrow-derived cells expressing nerve cell markers were present in the brain of mice which received intravenous administration of HMGB-1 after creation of cerebral infarction. These GFP-positive cells are presumably derived from non-inflammatory cells such as bone marrow mesenchymal stem cells.

Example 6

Effect of HMGB-1 Administration in Reducing Cerebral Infarct Size

Eight-week-old female C57/B16 mice were anesthetized by isoflurane inhalation. Then, the head skin was opened, and the probe of a laser Doppler blood flowmeter was directly attached to the cranial bone to monitor the cerebral blood flow. Next, a median skin incision was made from the sternum to the lower jaw. The right common carotid artery was detached and ligated loosely with a #4 silk suture. The right external carotid artery was ligated at a distal position using a #6 silk suture. A puncture was made on the right external carotid artery at a proximal position while applying tension to the suture around the common carotid artery. A #6 monofilament nylon suture (intraluminal filament) with a tip of 700 μm shaped by heat was inserted at the puncture site. The filament was advanced toward the internal carotid artery until about 8 mm of the suture tip was inserted. Then, the suture around the common carotid artery was loosened. It was confirmed that the reading of the laser Doppler blood flowmeter was reduced by 10 times after the blockage of blood flow.

After 30 minutes of blood flow blockage, the intraluminal filament was withdrawn to restore the blood flow. After 12 hours, purified HMGB-1 (10 μg) diluted with 500 μl of PBS was administered to the prepared disease model mice via the caudal vein. HMGB-1 was then administered four times at 24-hour intervals in the same manner. Control mice were administered with PBS.

Five days after the last day of the treatment, perfusion fixation was carried out using 2% paraformaldehyde under isoflurane inhalation anesthesia. The brain was removed from the cranial bone. After dehydration, the brain was placed in OTC compound, and frozen on dry ice to prepare a block. The block was sliced into 8-μm sections with a microtome for cryosectioning, and the sections were spread on silane-coated glass slides. After spreading, the sections were thoroughly dried, and washed with PBS to remove OCT compound. Following 10 minutes of fixation with PBS containing 4% paraformaldehyde, the sections were washed with phosphate buffer for 5 minutes, and immersed in distilled water for 10 minutes. Then, the samples were stained for 13 minutes with a 0.5% Cresyl Violet solution. After one minute of wash with distilled water, the sections were immersed in 50% ethanol, 75% ethanol, 95% ethanol, and 100% ethanol for 10 seconds each, twice in xylene for two minutes, and finally mounted using Entellan.

Figure 6:
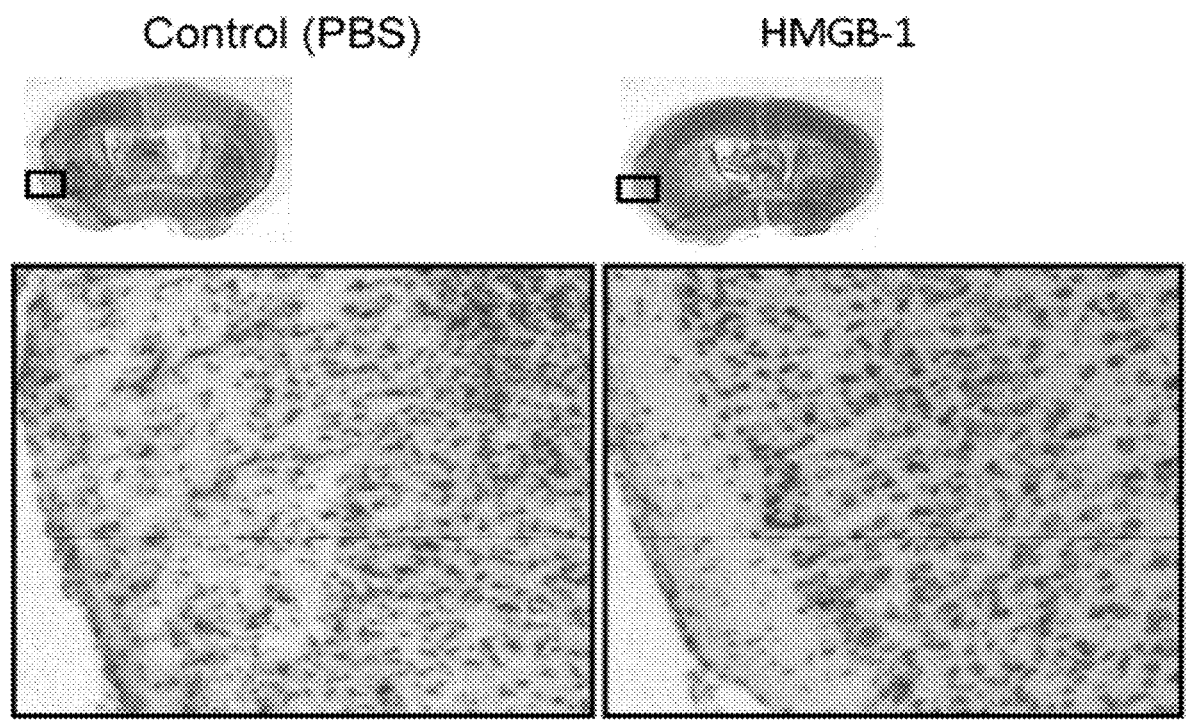
FIG. 6 is a set of photographs showing a result of detecting infarction sites. Disease model mice for cerebral infarction were produced, and then HMGB1 was intravenously administered to them. After the treatment, thin brain sections were prepared and subjected to Nissl staining. In the PBS administration (control) case, necrotic tissues were observed in the cortex. In the HMGB1-treated case, no necrotic tissue was found in the cortex.

The result is shown in FIG. 6. Significant improvement of the cerebral infarction was observed in mice administered with HMGB-1 as compared to mice administered with PBS.

In the experiment described above, a cerebral infarct-reducing effect was produced by intravascular administration of HMGB-1 after creation of cerebral infarction. It has been previously known that the intravenous administration of patient's own bone marrow cells after cerebral infarction provides a cerebral infarct-ameliorating effect. Since HMGB-1 has the activity of recruiting bone marrow-derived pluripotent stem cells, it is expected to produce the same effect as that of the intravenous administration of bone marrow cells. In addition, since the direct administration of HMGB-1 to the site of cerebral infarction may potentially cause damages and inflammation in brain tissues, the administration at a non-target site, for example, intravascular administration and subcutaneous administration as used in the experiments described above, is an excellent administration method that enables therapeutic treatment of cerebral infarction.

Example 7

Improvement of Post-Cerebral Infarction Survival Rate by Administration of HMGB-1

Eight-week-old male C57/B16 mice were anesthetized by isoflurane inhalation. Then, the head skin was opened, and the probe of a laser Doppler blood flowmeter was directly attached to the cranial bone to monitor the cerebral blood flow. Next, a median skin incision was made from the sternum to the lower jaw. The right common carotid artery was detached and ligated loosely with a #4 silk suture. The right external carotid artery was ligated at a distal position using a #6 silk suture. A puncture was made on the right external carotid artery at a proximal position while applying tension to the suture around the common carotid artery. A #6 monofilament nylon suture (intraluminal filament) with a tip of 700 μm shaped by heat was inserted at the puncture site. The filament was advanced toward the internal carotid artery until about 8 mm of the suture tip was inserted. Then, the suture around the common carotid artery was loosened. It was confirmed that the reading of the laser Doppler blood flowmeter was reduced by 10 times after the blockage of blood flow.

After a certain period of blood flow blockage (45 or 60 minutes) in each mouse, the intraluminal filament was withdrawn to restore the blood flow. After 12 hours, purified HMGB-1 (10 μg) diluted with 500 μl of PBS was administered to the prepared disease model mice via the caudal vein. HMGB-1 was then administered four times at 24-hour intervals in the same manner. Control mice were administered with PBS. The survival rate was monitored for 7 days after creation of infarction.

Figure 7:
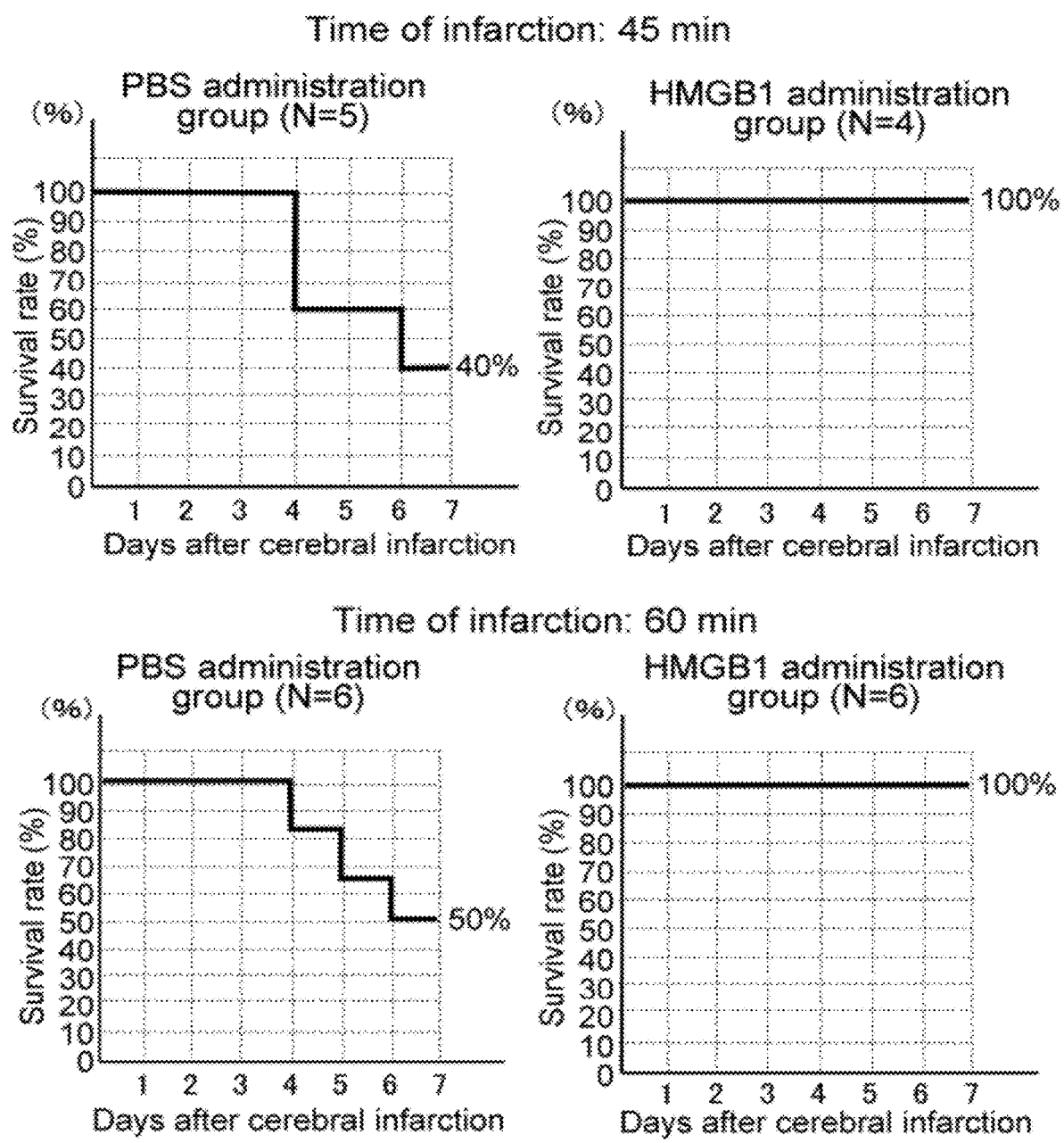
FIG. 7 is a set of graphs showing survival rates during 7 days after creation of cerebral infarction. Disease model mice for cerebral infarction were produced (by 45-minute or 60-minute ischemia) and then treated by intravenous administration of HMGB1. The HMGB1 treatment was demonstrated to improve the survival rate in both 45-minute and 60-minute ischemia cases.

The result is shown in FIG. 7. All mice that underwent 30 minutes of infarction survived for 7 days (N=3) (figure not shown). In the mice subjected to 45-minute infarction, the 7-day survival rate was 40% in the PBS administration group, whilst all mice survived in the HMGB-1 administration group. In the mice that underwent 60-minute infarction, the 7-day survival rate was 50% in the PBS administration group, whilst all mice survived in the HMGB-1 administration group.

In both of the 45-minute and 60-minute infarction models, only about half of the mice in the control group (PBS administration group) survived for 7 days. When the HMGB-1 administration was started 12 hours after the creation of cerebral infarction, the rate of survival after 7 days of the creation of infarction was improved. Cerebral infarction affects the vital prognosis depending on the site, area, and duration of infarction. Furthermore, cerebral infarction often involves paralysis, loss of consciousness, and such, which could cause a delay in treatment by a medical institution. Current pharmaceutical agents with demonstrated effectiveness, such as t-PA preparation, must be administered within 3 to 4 hours after the onset. Therefore, only a very small proportion of total cerebral infarction cases are indications for such preparations. To date, there are few therapeutic agents that can be administered and effective even if a long time has passed since the onset of cerebral infarction. The present invention can improve the vital prognosis by intravenous administration, which is a very simple, less-invasive method, even when the administration is started long time (12 hours) after the onset of cerebral infarction. It is therefore possible to develop novel therapeutic agents for treating cerebral infarction that can be administered in many cerebral infarction cases.

Example 8

Involvement of Bone Marrow Pluripotent Stem Cells from Sites Other than a Bone Fracture Site in Bone Fracture Healing Process A male C57BL/6 mouse (6 weeks old) was irradiated at a lethal dose (10 Gy). Immediately, bone marrow cells ($5\times10^6$ cells/0.1 ml physiological phosphate buffer (pH 7.4)) derived from a green fluorescent protein (GFP) transgenic mouse were transplanted via the caudal vein (GFP-bone marrow chimeric mouse). After 8 weeks, the GFP bone marrow chimeric mouse (mouse on the left in FIG. 8) and a wild type mouse (mouse on the right in FIG. 8) were conjoined via the skin for parabiosis. Then, a bone fracture was created in the right lower limb of the wild type mouse (mouse at the right in FIG. 8). Tissue sections were prepared after healing of the bone fracture. The sections were blocked with PBS containing 4% skim milk, and then reacted with an anti-mouse osteocalcin antibody diluted with PBS containing 4% skim milk. After washing with PBS, the sections were reacted at room temperature for one hour with a PE-labeled anti-rat IgG antibody diluted with PBS containing 4% skim milk. Following wash with PBS, the nuclei were stained with DAPI. Then, the samples were washed with PBS. After mounting, the fluorescence was observed using a confocal laser microscope.

Figure 8:
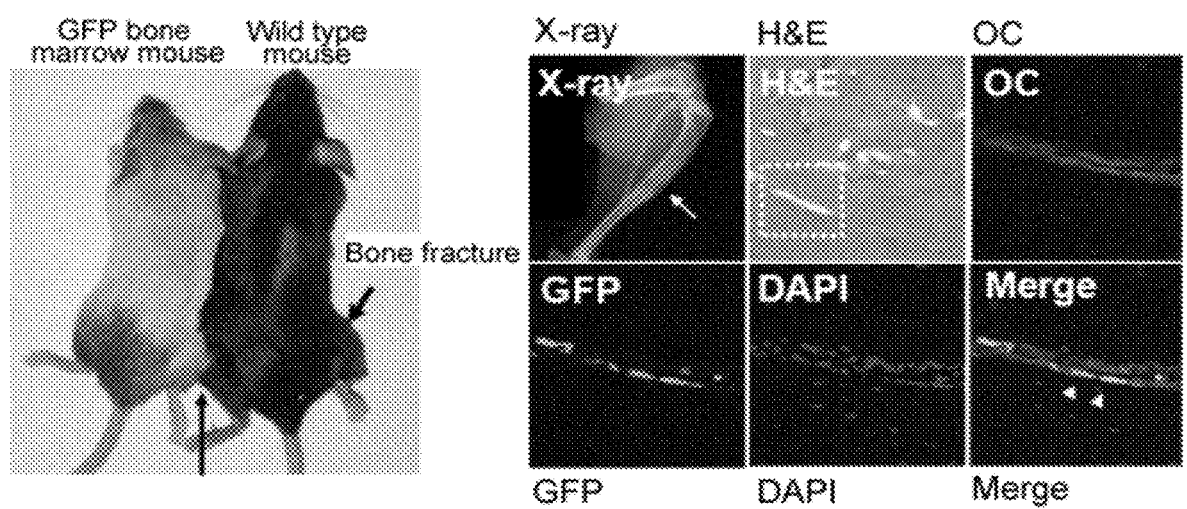
FIG. 8 is a set of photographs showing that, when a GFP-bone marrow-transplanted mouse was conjoined via the skin with a wild type mouse, bone marrow cells migrated from the GFP-bone marrow chimeric mouse to a bone fracture site of the right leg in the wild type mouse and differentiated into osteoblasts. A GFP-bone marrow-transplanted mouse was conjoined via the skin with a wild type mouse. Then, bone fracture was created in the wild type mice. After healing of bone fracture, some osteocalcin-expressing osteoblasts were found to be GFP-positive cells. This suggests that, in the process of bone fracture healing, bone marrow-derived cells distant from a damaged site migrate to the bone fracture site and then differentiate into osteoblasts for physiological healing of the damage.

The result is shown in FIG. 8. Osteocalcin (OC) is visualized as red fluorescence, while GFP-positive cells, i.e. bone marrow-derived cells, are visualized as green fluorescence. On the superimposed image (Merge), yellow cells are osteocalcin-positive bone marrow-derived cells. Thus, FIG. 8 demonstrates that bone marrow cells of the GFP-bone marrow chimeric mouse on the left migrated to the bone fracture site in the right leg of the wild type mouse, and differentiated into osteoblasts.

It has been previously believed that, in the process of bone fracture healing, osteoblasts in the vicinity of a damaged site accumulate at the damaged site and promote healing. The present result, however, demonstrates that bone marrow-derived cells distant from the damaged site migrate to the bone fracture site and repair the damaged tissues. The mouse on the right has subcutaneous and intradermal vascular connection with the mouse on the left. Therefore, if a considerable number of bone marrow pluripotent stein cells such as bone marrow mesenchymal stem cells can be successfully recruited to blood from bone marrows throughout the body, it is expected to be possible to promote the healing of the site of bone fracture.

Example 9

Figure 42:
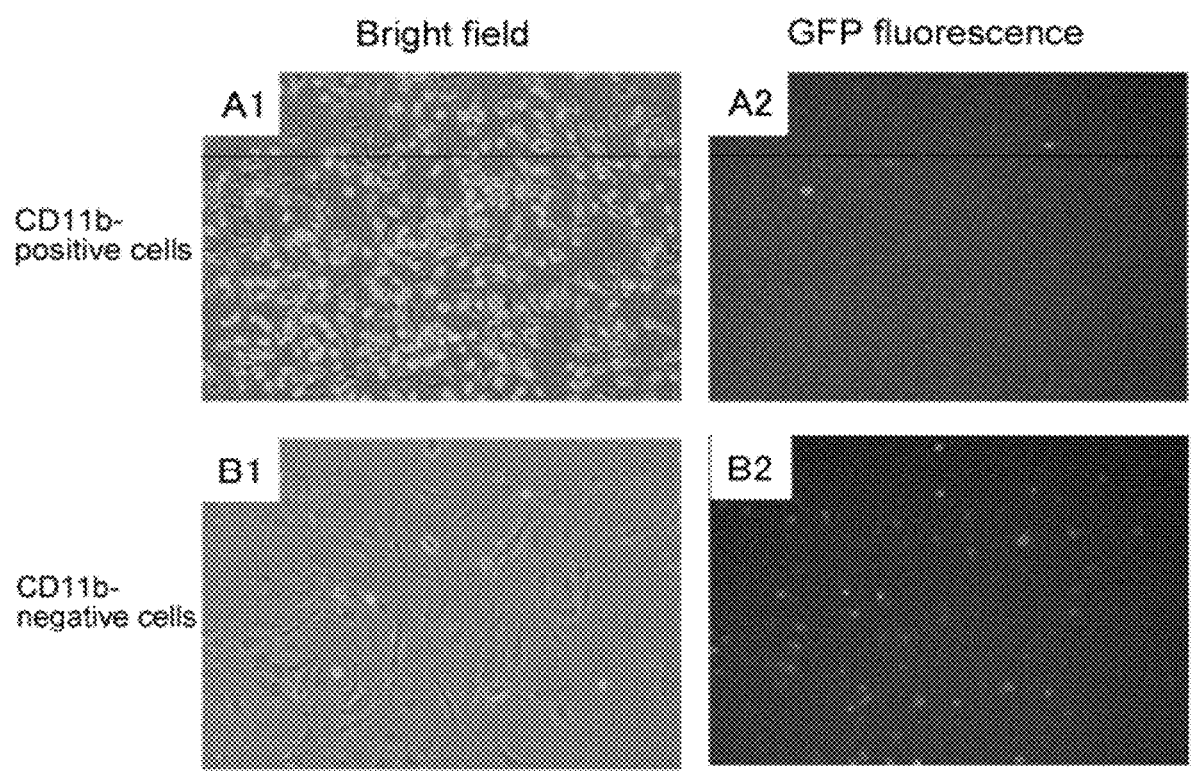
FIG. 42 is a set of photographs of cells obtained after sorting bone marrow-derived adherent cells of PDGF receptor α-GFP knock-in mouse using anti-CD11b MACS beads.

Objectives: Assessment of Intravenously Administered HMGB1 for the Activity of Recruiting Bone Marrow Mesenchymal Stem Cells to a Damaged Site in Bone Fracture Model Mice Methods: Studies were Carried Out by the Following Methods to Achieve the Above Objective:
(1) Mice in which GFP was knocked-in downstream of the promoter of PDGF receptor α in the genome (PDGFRα-GFP mice) (reference: Hamilton et al., Mol Cell Biol. 2003 June; 23(11):4013-25) were used in the experiment. The mice express GFP in cells expressing PDGF receptor α, which can be detected as green fluorescence when observed with a fluorescent microscope.
(2) Bone marrow cells were collected from PDGFRα-GFP mice, and plated in cell culture dishes. The cells were cultured in α-MEM containing 10% FBS. The medium was changed every three or four days, and the adhered cells were harvested after about 14 days. The harvested cells were sorted into CD11b-positive cells and CD11b-negative cells using anti-CD11b MACS beads. Fluorescent microscopy demonstrated that the CD11b-positive cells were negative for GFP (FIG. 42, A1 and A2) while the CD11b-negative cells were positive for GFP (FIG. 42, B1 and B2). The Boyden chamber method was carried out to test whether HMGB1 would induce the migration of these cells. The CD11b-positive cells or CD11b-negative cells were placed in the upper layer of a Boyden chamber. HMGB1 was diluted to 0, 50, or 100 µg/ml with DMEM containing 10% FBS, and added to the lower layer. The chamber was allowed to stand at 37° C. under 5% $CO_2$ in an incubator. After four hours, the membrane was removed from the chamber, and cells that migrated to the lower layer were detected by staining (FIG. 43).
(3) 12-week-old male PDGFRα-GFP mice were subjected to general anesthesia using isoflurane and a bone fracture model was made on the tibia of the left lower leg. Ten µg of HMGB1 diluted with 500 µl of PBS was administered via the caudal vein immediately, 24 hours, and 48 hours after creation of bone fracture. In negative controls, 500 µl of PBS was administered via the caudal vein (N=6).
(4) After 72 hours of bone fracture creation, the left tibial bone was removed, and allowed to stand for 24 hours in PBS containing 4% paraformaldehyde to fix the tissue. The bone was washed with PBS, and then observed under a fluorescent stereoscopic microscope to detect GFP fluorescence (FIG. 44).

Results: CD11b-positive cells were negative for GFP, suggesting that the cells did not express PDGF receptor α (FIG. 42; A1 and A2). CD11b-negative cells were positive for GFP, suggesting that they express PDGF receptor α (FIG. 42; B1 and B2). HMGB1 did not induce the migration of CD11b-positive (PDGF receptor α-negative) cells; however, it induced the migration of CD11b-negative (PDGF receptor α-positive) cells (FIG. 43).

As compared to the negative control mice of the PBS administration group (FIG. 44; D1), in four out of the six mice of the HMGB1 administration group (FIG. 44; D2), GFP-positive (PDGF receptor α-positive) cells were found in the bone around the bone fracture site.

Discussion: In the present experiment, mice (PDGFRα-GFP mice) whose cells positive for PDGF receptor α, which is one of the bone marrow mesenchymal stem cell markers, express GFP, were used to observe live bone marrow mesenchymal stem cells. Bone marrow cells include hematopoietic cells (erythrocytes, leukocytes, macrophages, etc.) and mesenchymal cells. Of these, macrophages (CD11b-positive) and bone marrow mesenchymal stem cells (CD11b-negative) are known to adhere to cell culture dishes. Meanwhile, since PDGF receptor α is a marker for bone marrow mesenchymal stem cells, the CD11b-negative, GFP-positive (PDGF receptor α-positive) cells found in this experiment may be bone marrow mesenchymal stem cells. The result of the Boyden chamber method demonstrated that HMGB1 induced the migration of bone marrow mesenchymal stem cells (PDGF receptor α-positive, CD11b-negative) without inducing the migration of macrophages (CD11b-positive cells). In addition, in the bone fracture model using PDGFRα-GFP mice, GFP-positive cells (PDGF receptor α-positive cells) were found to gather around the bone fracture site in the HMGB1 administration group, as compared to the negative control group. These GFP-positive cells are considered to be bone marrow mesenchymal stem cells recruited by HMGB1.

Bone marrow mesenchymal stem cells are known to be pluripotent stem cells, which differentiate into osteoblasts, chondrocytes, adipocytes, and others. Meanwhile, it is generally believed that bone fracture is healed by osteoblasts migrating from a bone fracture site or surrounding areas. However, as shown by the result of the parabiosis experiment in Example 8, bone marrow mesenchymal stem cells in bones other than the bone fracture site may contribute to regeneration of the bone fracture site.

The present experimental result revealed that bone marrow mesenchymal stem cells that were recruited to blood by intravenous administration of HMGB1 accumulated at the bone fracture site. This suggests that HMGB1 can be used as a therapeutic agent for bone fracture.

Macrophages, which are CD11b-positive (PDGF receptor α-negative), are inflammatory cells. Accordingly, allowing no macrophage to migrate will lead to prevention of excessive inflammation. Excessive inflammation is disadvantageous for tissue regeneration, because it can enlarge tissue damage and prolong the duration of healing. The above result demonstrates that HMGB1 has the activity of specifically inducing the migration of mesenchymal stem cells, which are effective in tissue regeneration.

Conventionally, bone fracture is mostly treated by non-invasive reduction, surgery, and casting. There are few pharmaceutical agents for actively promote the healing of bone fracture. Since the present method is performed by intravenous administration of an agent, it is also applicable to intractable bone fractures, bone fractures that are difficult to treat by surgery, and such. The present method therefore provides a novel breakthrough therapy.

Reference Example 1

Objective: Assessment of the contribution of bone marrow-derived cells towards functional regeneration of skin tissue transplanted to a living body.
Methods: In view of the above objective, studies were carried out by the following methods.
1) Utilizing the live skin transplant system of GFP bone marrow-transplanted mice, the degree of contribution of bone marrow-derived cells towards functional regeneration of grafted skin was examined. Specifically, 6 to 8-week-old male C57BL/6 mice were irradiated with a lethal dose of radiation (10 Gy), and immediately after that, GFP (green fluorescent protein) transgenic mouse-derived bone marrow cells ($5 \times 10^6$ cells/0.1 ml of physiological phosphate buffer solution at pH 7.4) were transplanted through the caudal vein.

2) The transplanted bone marrow cells were allowed to engraft (for 6 weeks), and as a result, a GFP bone marrow-transplanted mice was obtained. Then, skin of a neonatal mouse (female) was transplanted to the dorsal skin of the GFP bone marrow-transplanted mice.

3) The skin graft was, allowed to engraft and having had satisfactory skin tissue regeneration (4 weeks), the degree of GFP fluorescence accumulation in the grafted skin area was observed using a fluorescence stereoscopic microscope.

4) Under inhalational anesthesia, the skin graft was collected by biopsy. Then, frozen skin sections (6 µm) were prepared using a microtome with a cooling apparatus, and then were fixed with 4% paraformaldehyde (for 30 minutes). Cell nuclei in the tissue were stained with DAPI. Immunostaining was performed using an antibody against epidermal cell-specific keratin 5. The tissue was sealed to examine the presence of GFP-positive bone marrow-derived cells with a confocal laser microscope. A part of the specimen was stained with HE to examine its tissue construction.

Figure 9:
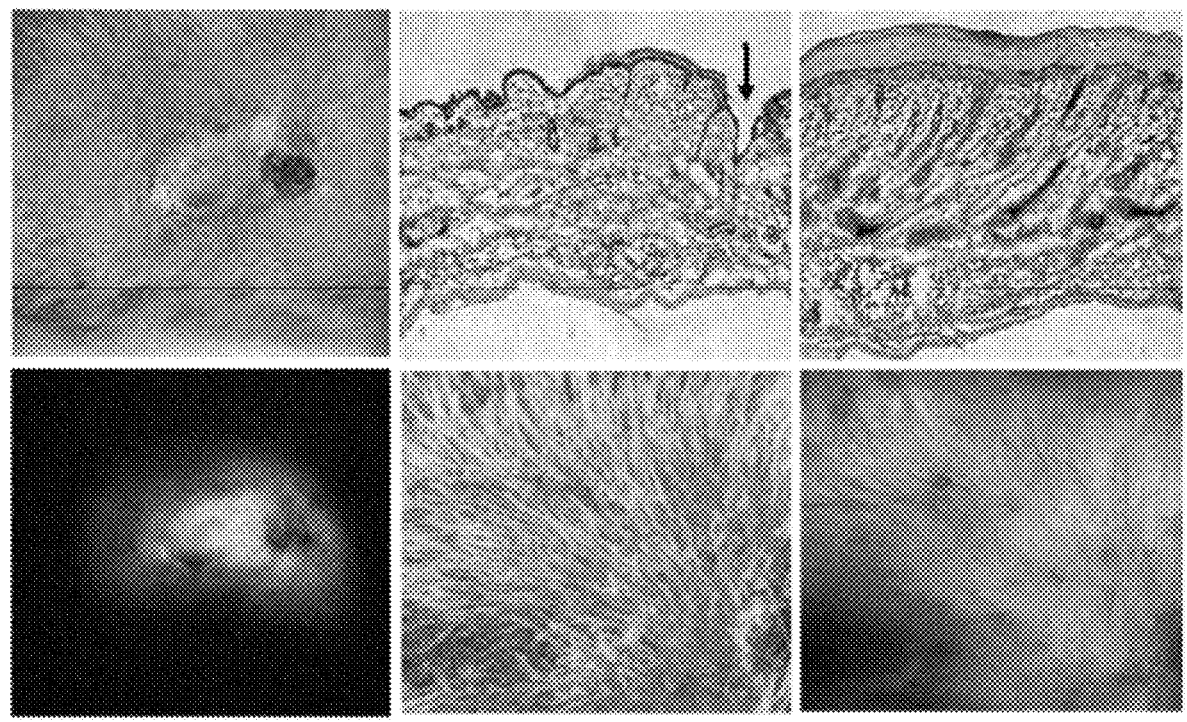
FIG. 9 presents photographs showing the accumulation of GFP fluorescence observed in a skin graft after skin transplantation to the back of a GFP bone marrow-transplanted mouse. Top left is an image of the skin transplantation area seen by the naked eye, top middle is an image of HE-stained tissue of a recipient skin in the vicinity of the boundary between the grafted skin and the recipient skin (shown by the arrow), and top right is an image of HE-stained tissue of the skin graft. Furthermore, the bottom left image shows the accumulation of GFP fluorescence in the grafted skin, bottom middle is an enlarged image of the skin transplantation area, and bottom right is an enlarged image showing the accumulation of GFP fluorescence in the same enlarged image of the skin graft.
Figure 10:
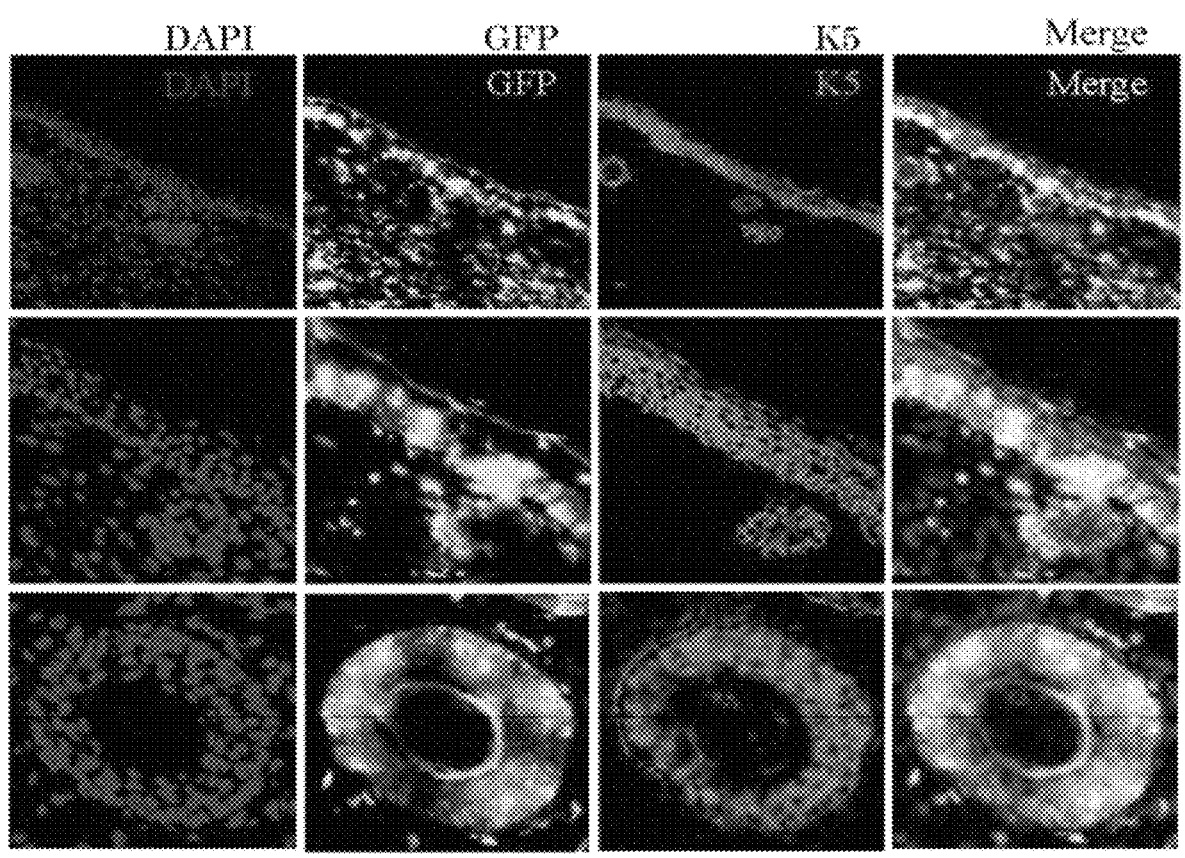
FIG. 10 presents a set of photographs showing bone marrow-derived epidermal cells and bone marrow-derived dermal fibroblasts that accumulated in the grafted skin at the back of the GFP bone marrow-transplanted mouse. The first row on top shows images of the skin of the transplantation area under low magnification (×100), the middle row shows enlarged images of the same showing the epidermis/dermis boundary under a high magnification (×200), and the bottom row shows further enlarged images of the same showing a hair follicle under a high magnification (×200). The far left column shows DAPI staining (nuclear staining), the second column from left shows GFP fluorescence images of the respective regions of the first row. The third column from left shows the immunostaining images of keratin 5 (K5). The fourth column from left shows merged images of each of these fluorescences. Large numbers of GFP-positive epidermal cells and dermal fibroblasts are observed.

Results: In the live skin transplant system of GFP bone marrow-transplanted mice, a strong GFP fluorescence accumulation corresponding to the regenerated skin region was observed (FIG. 9). Moreover, with the histological observation using the HE specimen of the skin graft, functional regeneration of skin tissue containing a large number of hair follicles was observed (FIG. 9). With the observation using a confocal laser microscope, GFP fluorescence was seen in many keratin 5-expressing epidermal keratinocytes, dermal fibroblasts, and further smooth muscle cells and adipocytes, showing that these cells derive from the bone marrow (FIG. 10). That is to say, it was revealed for the first time that many of the epithelial and mesenchymal cells required for functional regeneration of the transplanted skin were supplied from bone marrow-derived stem cells.

Discussion: For the first time, these study results clearly showed a breakthrough discovery that bone marrow-derived cells greatly contribute towards skin regeneration following skin transplantation, which is routine clinical procedure.

It is reported that the bone marrow has two stem cell systems: hematopoietic stem cells and mesenchymal stem cells. It is difficult to imagine that the large number of bone marrow-derived epithelial cells and mesenchymal cells that were mobilized into the transplanted skin (as shown by the present study) were supplied only from bone marrow-derived hematopoietic stem cells. This strongly suggests the possible contribution of bone marrow-derived mesenchymal stem cells towards the functional regeneration of transplanted tissues. That is to say, it was predicted that immediately after skin grafting, a factor for mobilizing bone marrow-derived mesenchymal stem cells is released from the recipient skin tissue heading towards hypoperfusion/necrosis, in which the mesenchymal stem cells are mobilized from the bone marrow through peripheral blood circulation to the transplanted skin piece, and thus inducing functional skin tissue regeneration.

Reference Example 2

Objective: Identification of a bone marrow-derived mesenchymal stem cell-attracting factor in a skin tissue extract Methods: With the objective of identifying a bone marrow-derived mesenchymal stem cell-mobilizing factor which is expected to be released from excised skin under hypoperfusive conditions, studies were carried out by the following methods.

1) To obtain mouse bone marrow-derived mesenchymal stem cells, bone marrow cells were collected from the femur or crus bone of C57BL/6 mice, and then were spread on a cell culture plate having a 10% fetal bovine serum-containing D-MEM (Nacalai) as a cell culture medium, and then were cultured under the condition of 5% $CO_2$ at 37° C. When the cells proliferated to the point of occupying 70 to 100% of the bottom area of the culture plate, the cells were peeled off from the culture plate using 0.25% trypsin 1 m MEDTA (Nacalai), and were then cultured under the above conditions. This passing and culturing procedure was repeated at least five times. Further, these adherent cells were isolated and cultured, followed by an analysis of cell surface antigens using flow cytometry, to confirm that these cells were Lin-negative, CD45-negative, CD44-positive, Sca-1-positive, and c-kit-negative. These cells were confirmed to be able to differentiate into bone cells and adipocytes and have properties of bone marrow mesenchymal stem cells.

2) Free skin pieces obtained from 400 neonatal mice were immersed in 400 ml of physiological phosphate buffer solution at pH 7.4 (PBS). The solution was incubated at 4° C. for 24 hours, and then was centrifuged at 440 G at 4° C. for 10 minutes to remove the tissue. The supernatant was collected to prepare a skin extract.

3) In order to confirm that the thus obtained skin tissue extract has an activity of attracting bone marrow-derived mesenchymal stem cells, its migration-inducing activity on C57BL6 mouse bone marrow-derived mesenchymal stem cells, which had been already established as a cell line by the present inventors, was examined using a Boyden chamber. Specifically, a skin extract (25 µl) was inserted into the lower chamber (volume: 25 µl) of the Boyden chamber, and a polycarbonate membrane having fine pores of 8 µm was placed on it. The upper chamber (volume: 50 µl) of the Boyden chamber was further placed on this in contact, and was filled with a bone marrow-derived mesenchymal stem cell suspension ($5 \times 10^4$ cells/50 ml of culture solution: DMEM/10% fetal bovine serum). The chamber was incubated in a $CO_2$ incubator at 37° C. for 4 to 24 hours. After culturing, the upper chamber was removed and the silicon membrane was taken out. The number of bone marrow-derived mesenchymal stem cells which had migrated to the lower chamber through the fine pores was quantitatively examined by staining.

4) To purify factors having a bone marrow-derived mesenchymal stem cell-mobilizing activity in the skin extract, heparin affinity column chromatography and anion exchange column (Q column) chromatography were carried out. The skin extract was diluted 10-fold with 9 volumes of 20 mM phosphate buffer at pH 7.5 at 4° C. (diluted solution A). 20 mM phosphate buffer at pH 7.5 (30 ml) was poured into HiTrap Heparin HP column (column volume: 5 ml, GE Healthcare) in advance to equilibrate the column. Further, the diluted solution A was allowed to bind to the column. Then, the column was washed with 20 mM phosphate buffer at pH 7.5 with 100 mM NaCl (30 ml). To elute the absorbed proteins, 20 mM phosphate buffer at pH 7.5 with 1000 mM NaCl were poured into the column, to elute the fractions into the tubes. The fractions having the migration-inducing ability according to the migration activity assessment method using a Boyden chamber as described in 2) were collected from each absorbed fraction. This was diluted with 9 volumes of 50 mM Tris HCl pH 8.0 (diluted solution B). 50 mM Tris HCl pH 8.0 (30 ml) was poured into HiTrap mono Q column (column volume: 1 ml, GE Healthcare) in advance to equilibrate the column. Further, the diluted solution B was allowed to bind to the column. In order to elute the absorbed proteins, Tris HCl pH 8.0 and 1000 mM NaCl were poured into the column, to eluate the fractions into tubes. The above purification process can all be performed at 4 to 16° C., but it is preferably 4 to 8° C., and more preferably 4° C. The eluates were assessed by the migration activity assessment method using Boyden chamber as described in 2).

5) The skin extract-derived purified preparations having the bone marrow-derived mesenchymal stem cell-mobilizing activity, which was obtained by combining the migration activity assessment using a Boyden chamber and column chromatography, were subjected to SDS-PAGE electrophoresis to separate within the gel based on the molecular weight, and the bands of migratory proteins were detected by silver staining.

6) Among the skin extract-derived protein groups that had been subjected to SDS-PAGE electrophoresis and that were separated within the gel as single bands by the silver staining of 5), all protein bands obtained from chromatography-purified preparations having the strongest bone marrow-derived mesenchymal stem cell-mobilizing activity were excised, and then the identification of these proteins by mass spectrometry and database analysis was carried out.

7) Among the identified protein groups, candidate proteins having the bone marrow-derived mesenchymal stem cell-mobilizing activity were selected. Purified preparations including such candidate proteins were treated with neutralizing antibodies (100 μl of purified preparation solution was incubated on ice for 30 minutes with 100-fold diluted polyclonal antibody of the candidate protein. Then, the degree of inhibition on the bone marrow-derived mesenchymal stem cell-mobilizing activity was examined by migratory ability assessment using a Boyden chamber.

8) The obtained purified bone marrow-derived mesenchymal stem cell preparations were mixed in Matrigel at about 10% volume. A silicon tube having a diameter of about 1 mm and a length of 5 mm was filled with the Matrigel, which was then subcutaneously transplanted to the back of GFP bone marrow-transplanted mouse. Two weeks after, the inserted tube was taken out, and GFP fluorescence emitting from bone marrow-derived cells which had migrated into the tube was quantitatively analyzed by a fluorimeter. Further, the migratory cells were taken out from the tube, and were inoculated into a DMEM/10% fetal bovine serum medium, followed by culturing in a $CO_2$ incubator, to examine the in vivo bone marrow-derived mesenchymal stem cell-mobilizing activity. These cells that were continuously cultured for 2 weeks were fixed with 2% paraformaldehyde at 25° C. for 10 minutes, and rinsed with PBS four times, 5 minutes each, to wash out the paraformaldehyde. Then this was treated with a 2% skim milk solution, and was allowed to react with 1000-fold dilution of anti-mouse keratin 5 antibody (diluted with 2% skim milk containing 0.5% tween 20) at 4° C. for 16 hours. The antibody was washed out with PBS four times for 5 minutes each. This was then allowed to react with 1000-fold diluted Alexa546-labelled anti-rabbit IgG antibody (diluted with 2% skim milk) at 25° C. for 1 hour.

Figure 11:
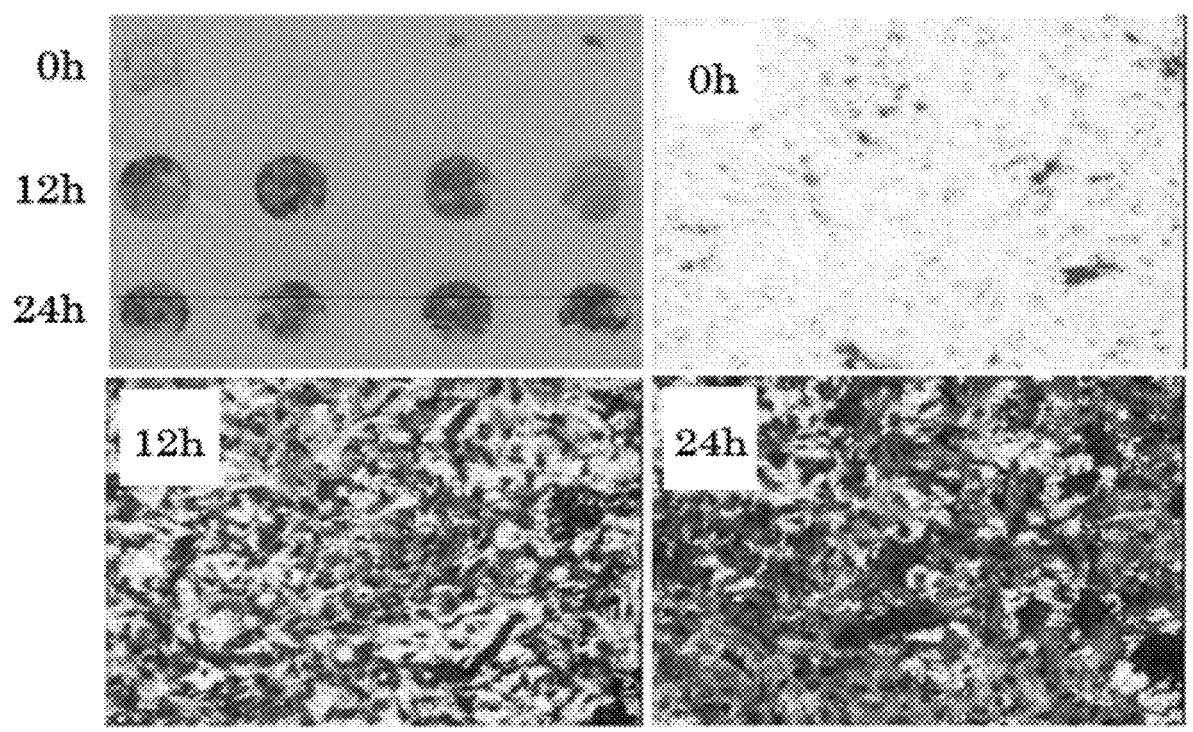
FIG. 11 presents a set of photographs showing assay results of the migratory ability/activity of bone marrow-derived mesenchymal stem cells in a skin extract using a Boyden chamber. The top left picture shows bone marrow mesenchymal stem cells adhered onto a silicone membrane on the lower chamber side, having migrated from the upper chamber of the Boyden chamber to the skin extract side (lower chamber side) through fine pores in the silicone membrane, which are stained with a blue pigment. The stained images axe shown immediately after culturing (0 h), after 12 hours (12 h), and after 24 hours (24 h) (four wells each) from the top. The top right picture is an image of 0 h enlarged under a high magnification. Bottom left is an image of 12 h enlarged under a high magnification. Bottom right is an image of 24 h enlarged under a high power magnification.
Figure 12:
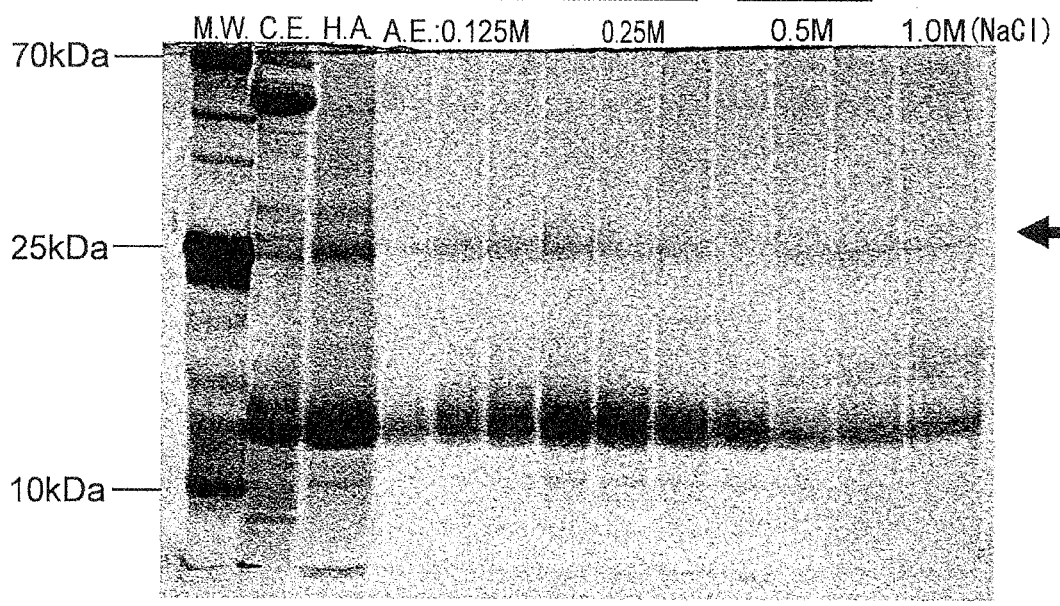
FIG. 12 presents a photograph showing the result of bone marrow-derived mesenchymal stem cells migratory ability/activity assay, examined in skin extract-purified fraction preparations using the Boyden chamber, and correspondence with the SDS-PAGE electrophoresis result for each purified fraction preparation. From the left, Lane 1 (M.W.): molecular weight marker; Lane 2 (C.E.): crude skin extract, Lane 3 (H.A.): heparin affinity column-binding fraction (semipurified fraction); and Lanes 4 to 13 (A.E.): anion exchange column-binding fractions (final purified fraction) eluted with various NaCl concentrations, which were all stained with silver after electrophoresis. Further, in the final purified fraction of No. 4, which showed the strongest bone marrow-derived mesenchymal stem cell migratory activity, the stained bands in the silver-stained image of the electrophoresis gel (lane 7) were cut out, and then subjected to mass spectrometry and database analysis. The result revealed that the band indicated by the arrow is HMGB1.
Figure 13:
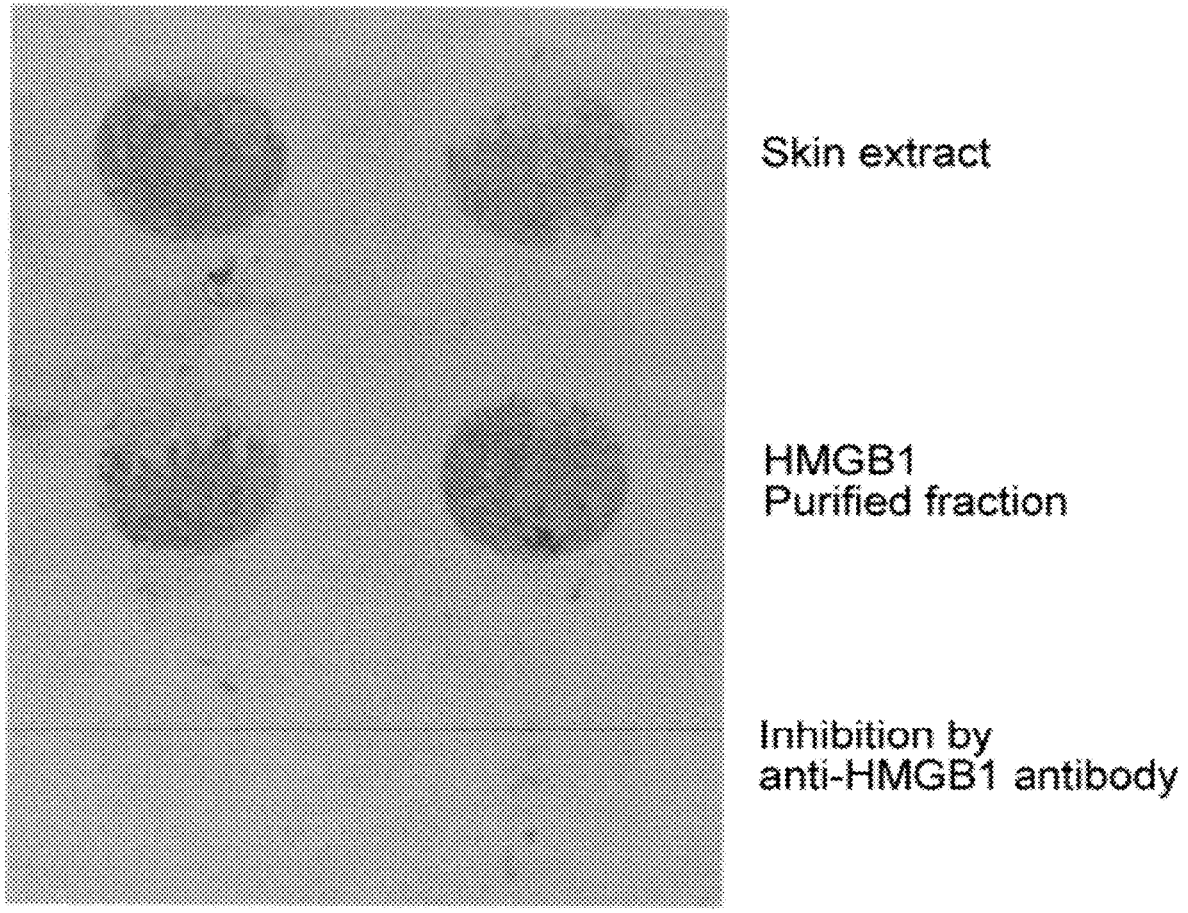
FIG. 13 presents a photograph showing the result of assessing the migration-inducing activity of HMGB1 on bone marrow-derived mesenchymal stem cells by using a Boyden chamber. The two images on the top are stained images of bone marrow-derived mesenchymal stem cells that migrated into the skin extract. The middle two images are stained images of bone marrow-derived mesenchymal stem cells that migrated into the HMGB1 purified preparation. In the bottom are stained images of bone marrow-derived mesenchymal stem cells that migrated into a solution of the HMGB1 purified preparation that was used for the middle images but neutralized by adding an anti-HMGB1 polyclonal antibody (the migratory activity was lost almost completely).

Results: Starting from the extract solution of excised skin of neonatal mouse in PBS, proteins having the bone marrow-derived mesenchymal stem cell-mobilizing activity were subjected to identification and functional analysis by the above-mentioned methods. The migration activity assessment using a Boyden chamber showed that the skin extract has an extremely strong bone marrow-derived mesenchymal stem cell-attracting activity (FIG. 11). Using this activity as an index, a heparin affinity column and an anion exchange column (Q column) were used to proceed with the purification of the target factor. The obtained fractions were each analyzed by SDS-PAGE electrophoresis. As a result, a strong bone marrow-derived mesenchymal stem cell-mobilizing activity was shown by silver staining in the purified preparation containing several proteins that were separated within the gel in the form of single bands (Lane 7 in FIG. 12). The obtained silver-stained bands were excised, and were then subjected to mass spectrometry and database analysis. As a result, it was revealed that the protein having a molecular weight of about 25,000 indicated by the arrow was HMGB1 (FIG. 12). To clarify that HMGB1 contained in this purified fraction (Lane 7) has the intended bone marrow-derived mesenchymal stem cell-mobilizing activity, a migration inhibition experiment was carried out using an anti-MGB1 polyclonal antibody. As a result, it was revealed that the anti-HMGB1 polyclonal antibody strongly inhibits the activity of the purified preparation in inducing the migration of bone marrow-derived mesenchymal stem cells (FIG. 13) and that the bone marrow-derived stem cell-mobilizing factor present in the skin extract is HMGB1.

Figure 14:
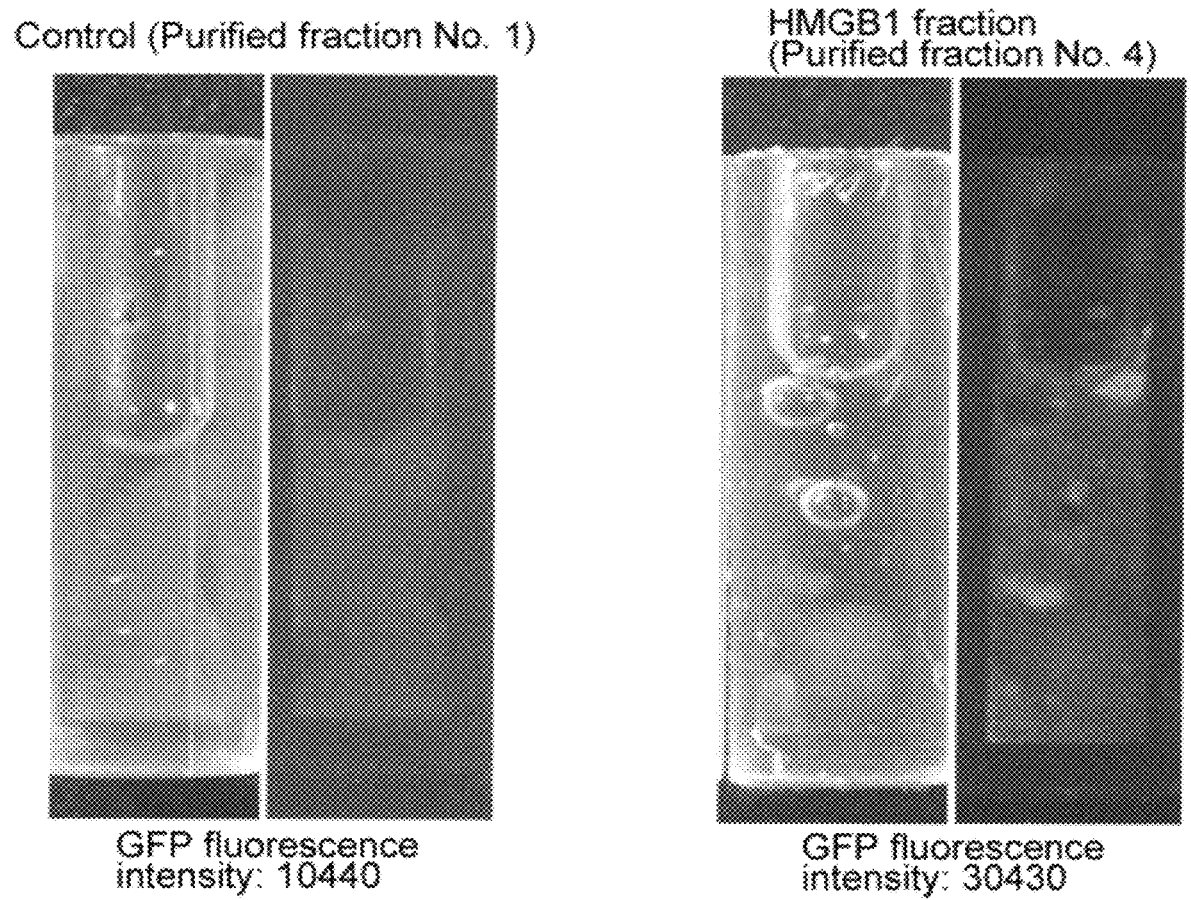
FIG. 14 presents a set of photographs showing the in vivo bone marrow-derived mesenchymal stem cell-mobilizing activity of HMGB1. The HMGB1 fraction (final purified fraction No. 4) showed about three times the mobilization activity of the control (final purified fraction No. 1).
Figure 15:
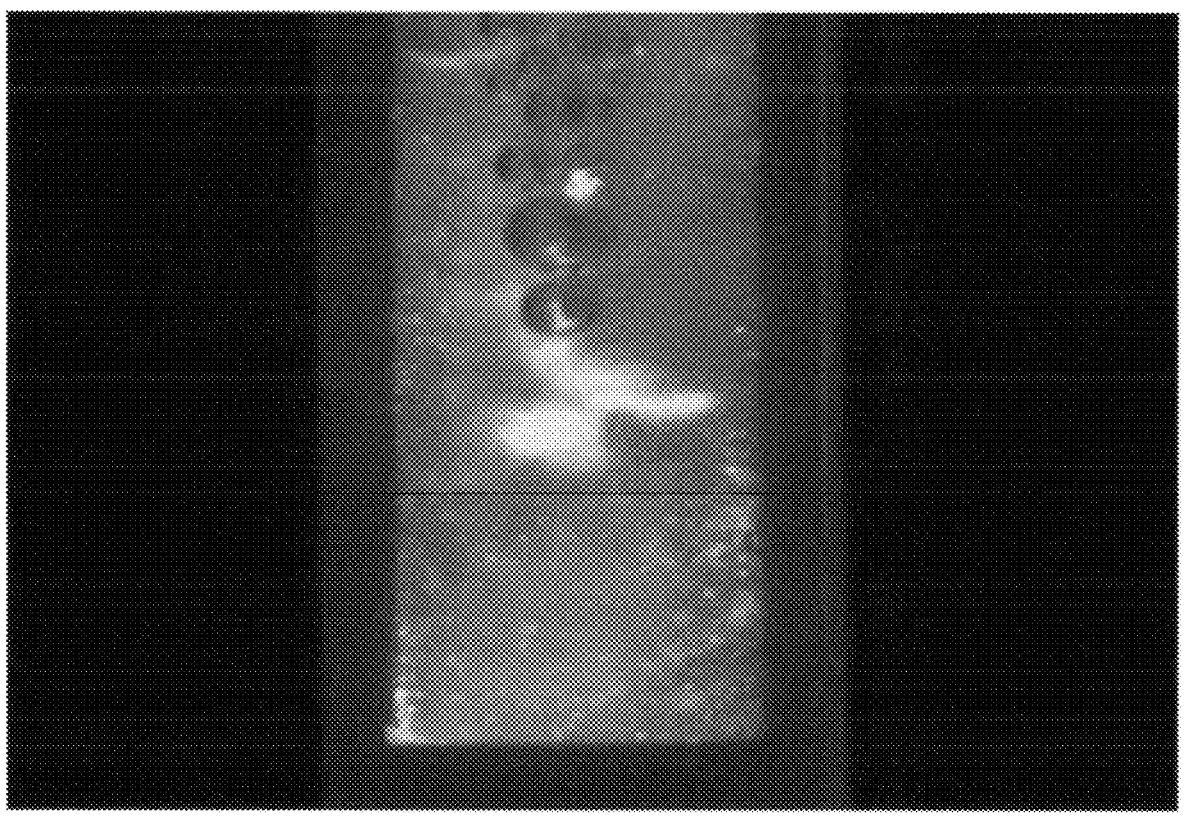
FIG. 15 presents a photograph showing cells mobilized in vivo by the HMGB1 fraction (final purified fraction No. 4) under a high magnification.
Figure 16:
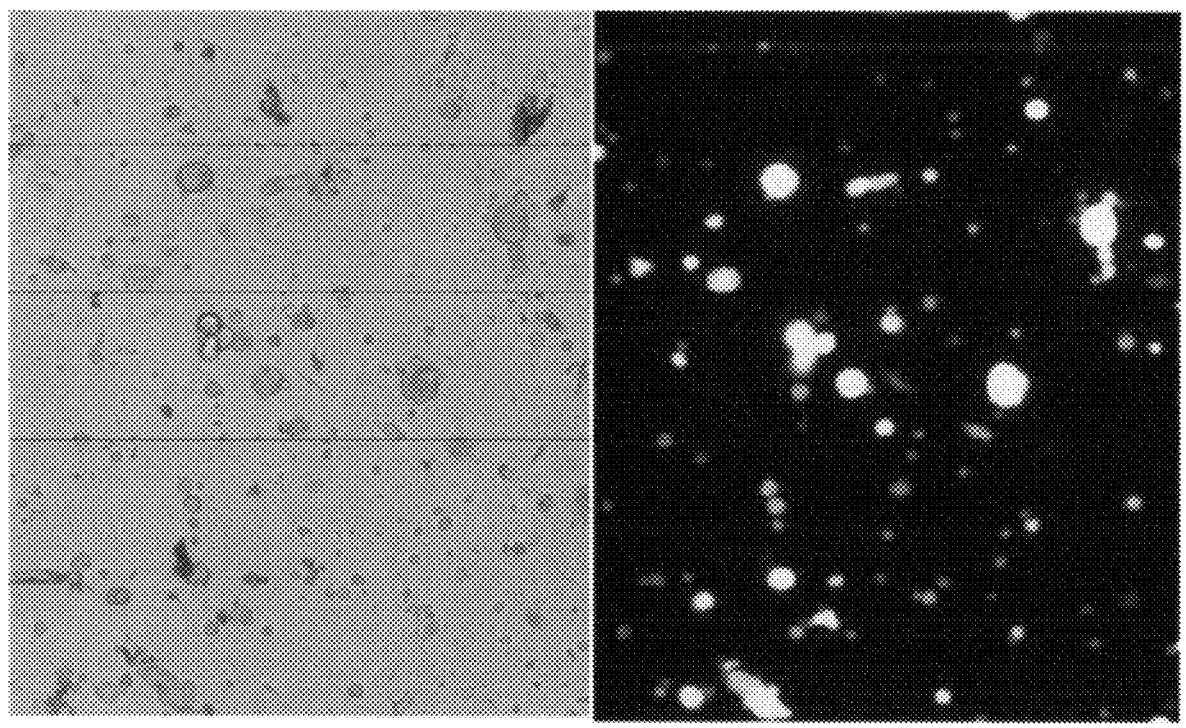
FIG. 16 presents a set of photographs showing images immediately after commencing culture of cells that migrated into a silicon tube. On the left is a light-field image of migratory cells inoculated into a medium, and the right shows its GFP fluorescence image under a dark field.
Figure 17:
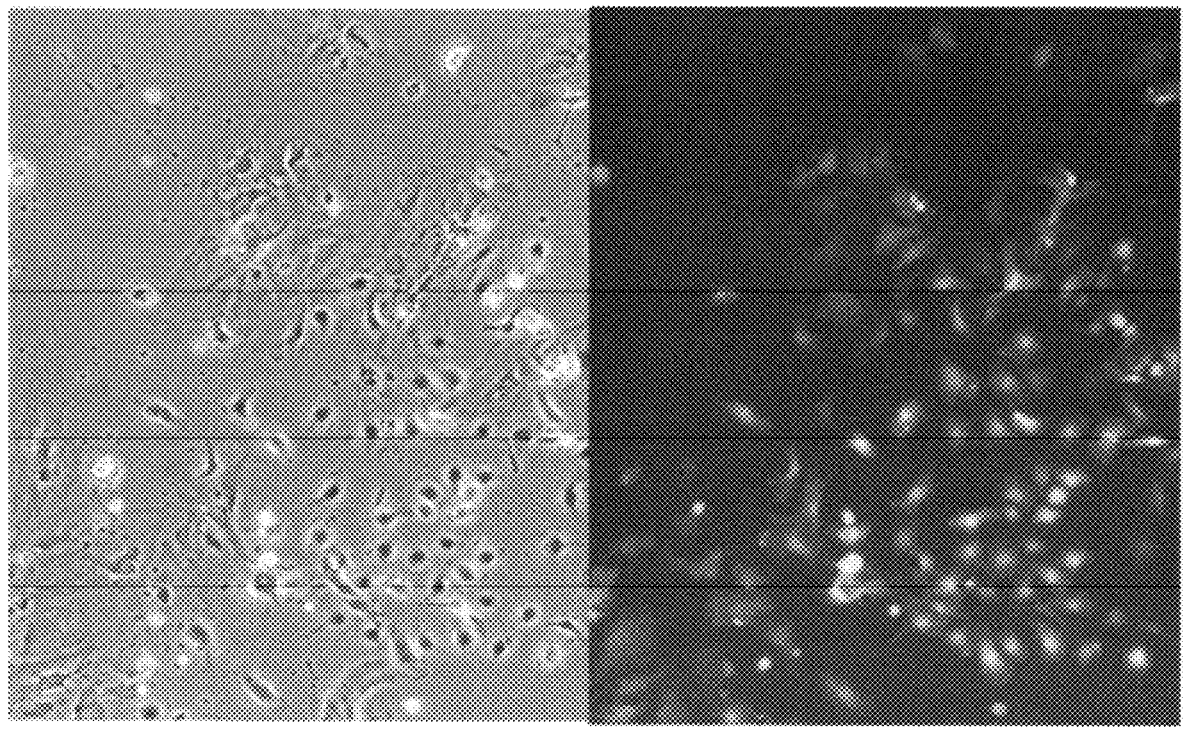
FIG. 17 presents a set of photographs showing images 24 hours after commencing culture of cells that migrated into the silicon tube. The left picture shows a light-field image of fibroblast-like cells and epithelial-like cells that proliferated and adhered onto the plastic culture dish, and the right picture shows its GFP fluorescence image under a dark field.
Figure 18:
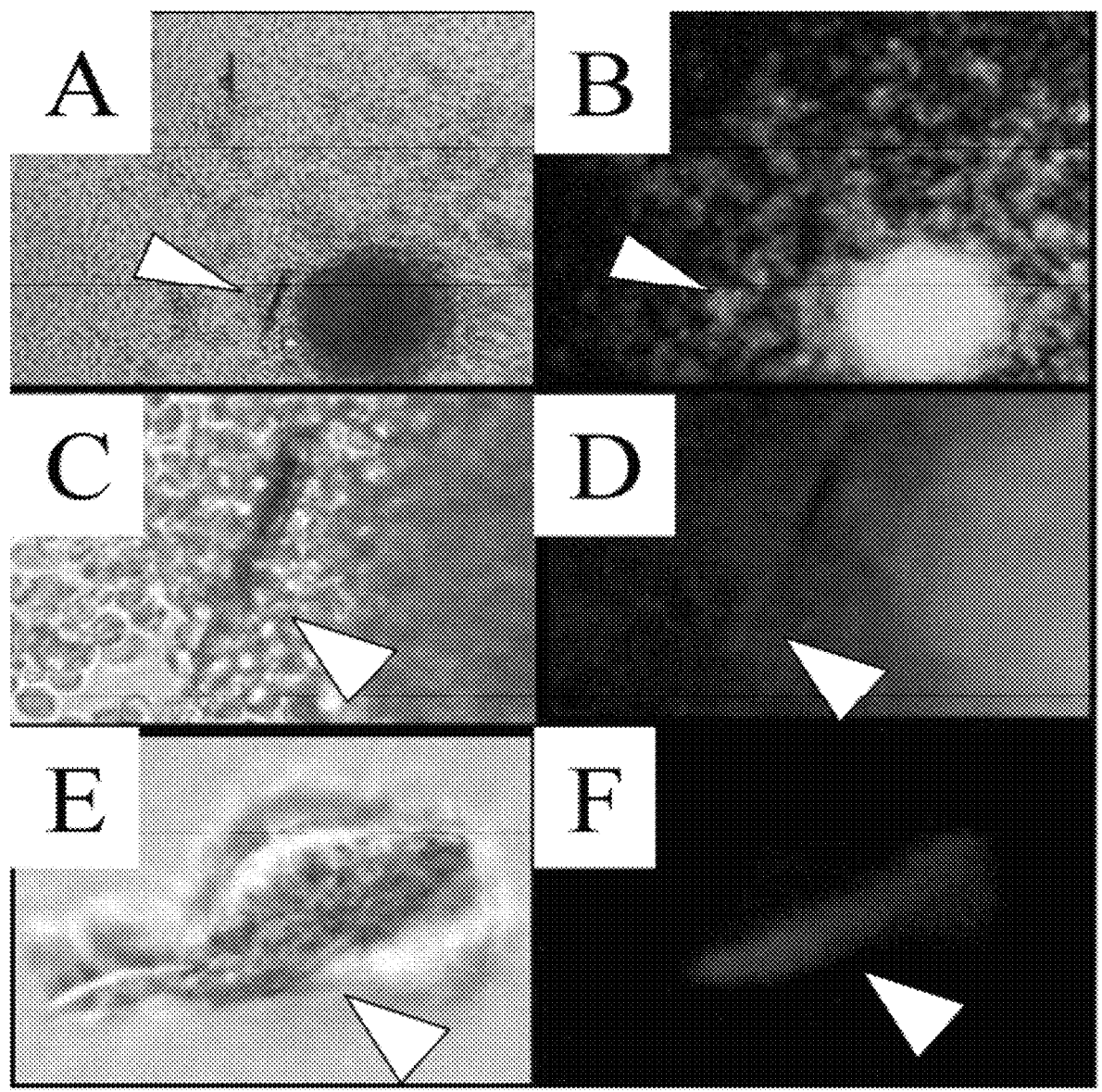
FIG. 18 presents a set of photographs showing images 2 weeks after commencing culture of cells that migrated into the silicon tube. The left and right photographs show the same field of view, in which the left shows images under a light field, whereas the right shows images through a fluorescence filter (GFP fluorescence is detected in B and D and fluorescence of keratin 5 is detected in F). A hair-like linear shape (indicated by the triangle (arrow)) is observed on the left side of bone marrow-derived GFP-positive cell population forming circular colonies on the plastic culture dish. F indicates that bone marrow-derived cells are morphologically transformed into a hair-like form, and are further expressing keratin 5 (indicated by the triangle (arrow)).

Further, to confirm that HMGB1 has a bone marrow-derived mesenchymal stem cell-mobilizing activity in vivo, a silicon tube containing this purified preparation was subcutaneously inserted into the back of GFP bone marrow-transplanted mouse. Two weeks after, the properties of cells mobilized into the tube were examined. As a result, the HMGB1 purified preparation mobilized a greater number of GFP-positive bone marrow-derived cells into the tube (about three times) as compared to the control (purified preparation used for Lane 4 in SDS-PAGE of FIG. 12) (FIG. 14). FIG. 15 shows a high magnification image by a fluorescence stereoscopic microscope. Further, GFP-positive cells mobilized into the tube were taken out, and were cultured in a DMEM/10% fetal bovine serum medium. As a result, round-shaped floating cells were observed immediately after culturing (FIG. 16), however 24 hours after the GFP-positive bone marrow-derived cells were confirmed to adhere onto the culture dish and proliferated in the form of spindle-shaped fibroblast-like cells and further in the form of cylindroid-shaped epithelial-like cells (FIG. 17). When these cells were continuously cultured for another 2 weeks, hair follicle-forming cells were observed among the GFP-positive bone marrow-derived cells (FIG. 18A; light field, low magnification, FIG. 18B; GFP fluorescence, low magnification, FIG. 18C; light field, high magnification, FIG. 18D; GFP fluorescence, high magnification). Moreover, when immunohistochemical techniques were used for keratin 5, a marker for epithelial keratinocytes, keratin 5-positive cells were observed among the GFP-positive bone marrow-derived cells (FIG. 18E; light field, FIG. 18F; fluorescence of keratin 5-positive cells).

Discussion: This time, the present inventors have discovered for the first time in the world that: free skin pieces produce HMGB1; the produced HMGB1 has an activity of mobilizing a large amount of bone marrow-derived mesenchymal stem cells into the skin pieces; bone marrow-derived mesenchymal stem cells mobilized into the skin pieces are differentiated into mesenchymal cells such as fibroblasts, adipocytes, smooth muscle cells in the skin tissue, and further are differentiated into cells that form hair follicles of epidermal cells, to induce functional regeneration of transplanted skin tissues. It can be readily predicted that this mobilization of bone marrow-derived mesenchymal stem cells by HMGB1 and the resulting functional tissue regeneration functions, not only for transplanted skin regeneration, but also as a mechanism for inducing functional tissue regeneration in various damaged organs/tissues accompanying hypoperfusion/necrosis. The present inventors firmly believe that, if drug development using an HMGB1 formulation enables the mobilization of bone marrow-derived mesenchymal stem cells to the local area during regeneration of the damaged tissues, it would enable functional tissue regeneration-inducing therapy for vital functional organs, without the organs becoming dysfunctional due to fibrous scar healing.

Reference Example 3

Objective: Identification of the HMGB1 family in the skin extract and examination of bone marrow mesenchymal stem cell-attracting activity Methods: Whether or not the neonatal mouse skin extract contained the HMGB protein family was confirmed using the Western blot method. Ten µl of the skin extract obtained in [Reference Example 2] was used as a sample and subjected to SDS-PAGE electrophoresis. The proteins separated within the gel were transferred onto a PVDF membrane using a blotting device (ATTO). The membrane was incubated with PBS containing 3% skim milk and 0.1% Tween 20 (S-T-PBS) at room temperature for 1 hour, and then was allowed to react with each of rabbit anti-mouse HMGB1 antibody, rabbit anti-mouse HMGB2 antibody, or rabbit anti-mouse HMGB3 antibody which were diluted 1000-fold with S-T-PBS, at 4° C. for 16 hours. After the reaction, the PVDF membrane was washed with S-T-PBS five times for 5 minutes. Then, the PVDF membrane was incubated with 2000-fold diluted (diluted with S-T-PBS) peroxidase labeled goat anti-rabbit IgG antibody (GE Healthcare) at 25° C. for 1 hour. Further, after washing with S-T-PBS five times for 5 minute, the PVDF membrane was allowed to react with ECL Western Blotting Detection System (GE Healthcare). The ECL film was exposed and developed to detect the presence of HMGB1, HMGB2, and HMGB3 proteins.

RNA was extracted from the skin of neonatal mouse using Trizol (Invitrogen), and further cDNA was synthesized using SuperScript III cDNA synthesis kit (Invitrogen). Using this cDNA as a template, cDNAs of HMGB1, HMGB2, and HMGB3 were amplified using the PCR (polymerase chain reaction) method. The cDNAs were inserted into the plasmid vector pCAGGS for expressing proteins in mammalian cells, such that proteins with an additional Flag tag sequence (Asp-Tyr-Lys-Asp-Asp-Asp-Lys; SEQ ID NO: 30) at the N terminus of the amino acid sequence could be expressed. These plasmid vectors were introduced into HEK293 (Human embryonic kidney derived culture cell line) and cultured for 48 hours to express the proteins. Cells expressing each of the HMGB1, HMGB2, and HMGB3 proteins and the culture supernatant were incubated at 4° C. for 16 hours, which was then centrifuged at 4400 g for 5 minutes to collect the supernatant. 100 µL of the anti-Flag antibody gel (Sigma) was mixed into 50 mL of this supernatant, and was then incubated at 4° C. for 16 hours. Centrifugation was then performed to collect the gel, and washed with PBS five times. Further, the protein was eluted using 3× Flag peptide (final 100 µg/ml). Expressions of recombinant proteins were observed by the Western blot method using 1000-fold diluted (diluted with S-T-PBS) mouse anti-Flag antibody and 2000-fold diluted (diluted with S-T-PBS) peroxidase-labeled anti-mouse IgG antibody (GE Healthcare). The activity of these purified recombinant proteins in inducing the migration of mouse bone marrow mesenchymal stem cells was assessed in the same manner as in [Reference Example 2] using a Boyden chamber. Moreover, in order to observe the in vivo drug efficacy of the HMGB family, the dorsal skin of 8-week-old C57BL/6 mice was cut out in a circle having a diameter of 8 µm to prepare cutaneous ulcer models. Purified HMGB1, HMGB2, and HMGB3 (100 ng) were each mixed with the same amount of hyaluronic acid solution having a concentration of 1 g/100 mL of PBS, and 100 µL of it was administered to the ulcer surface. The ulcer surface was covered with a transparent adhesive wound dressing/protective material Tegaderm (3M Healthcare) to avoid drying, and the wound area was measured over time to determine the therapeutic effect.

Further, to examine whether or not the human skin extract and the purified human HMGB1 has an activity to allow migration of human bone marrow mesenchymal stem cells, a Boyden chamber was used in the same manner as in [Reference Example 2] for assessment. A human skin having an area of 1 cm$^2$ was immersed in 1 ml PBS, and then was incubated at 4° C. for 16 hours and subsequently centrifuged at 440 G at 4° C. for 10 minutes. The supernatant alone was collected to be used as a human skin extract. Moreover, human bone marrow mesenchymal stem cells (Cambrex) were used as the cells to be placed in the upper chamber of the Boyden chamber (as a result of surface antigen analysis by flow cytometry, these cells have been confirmed to be CD105-positive, CD166-positive, CD29-positive, CD44-positive, CD34-negative, and CD45-negative. They have also been found to differentiate into adipocytes, chondrocytes, and bone cells by differentiation induction tests). Moreover, 100 ng/well of human HMGB1 (R&D) and human skin extract diluted 10-fold with PBS and were placed in the lower chamber. PBS was used as a control.

Figure 19:
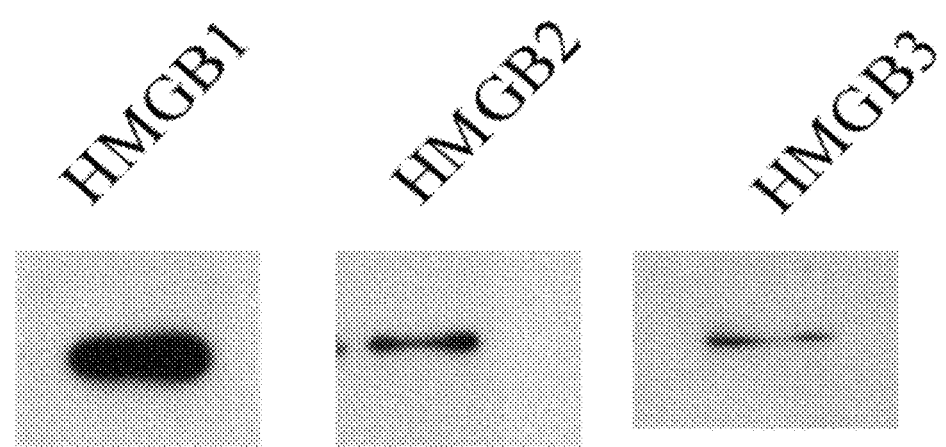
FIG. 19 presents a set of photographs showing the HMGB family in a newborn mouse skin extract, detected by the Western blot method.
Figure 20:
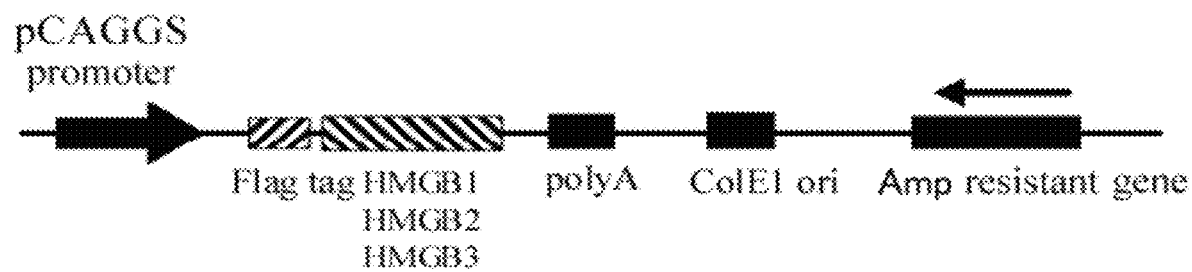
FIG. 20 shows an illustration of an expression vector map for the HMGB family in mammalian cells, which has, downstream of the promoter, a cytomegalovirus enhancer and a chicken β-actin promoter to synthesize a large amount of mRNAs encoded by the cDNA (complementary DNA) of the HMGB family.
Figure 21:
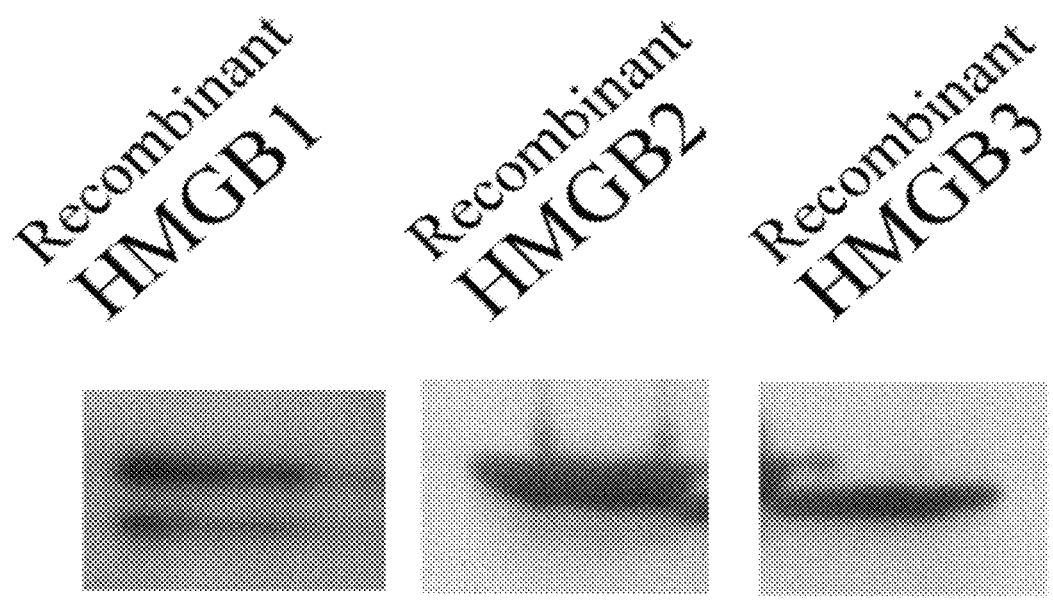
FIG. 21 presents a set of photographs showing the result of Western blotting of the purified recombinant Flag tag-HMGB family-fusion proteins expressed in HEK293 cells.
Figure 22:
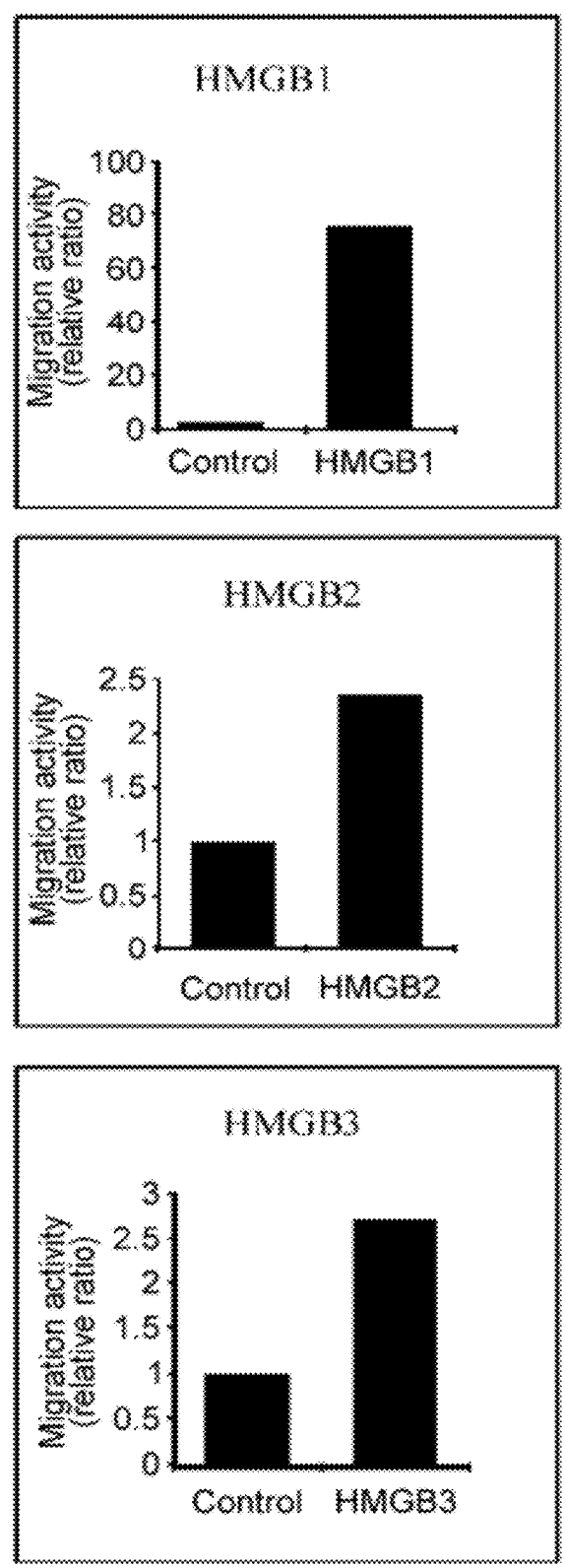
FIG. 22 presents a set of graphs showing the activity of recombinant HMGB1/HMGB2/HMGB3 in inducing the migration of bone marrow mesenchymal stem cells in a Boyden chamber. All recombinant proteins showed a higher migration-inducing activity as compared to the control groups.
Figure 23:
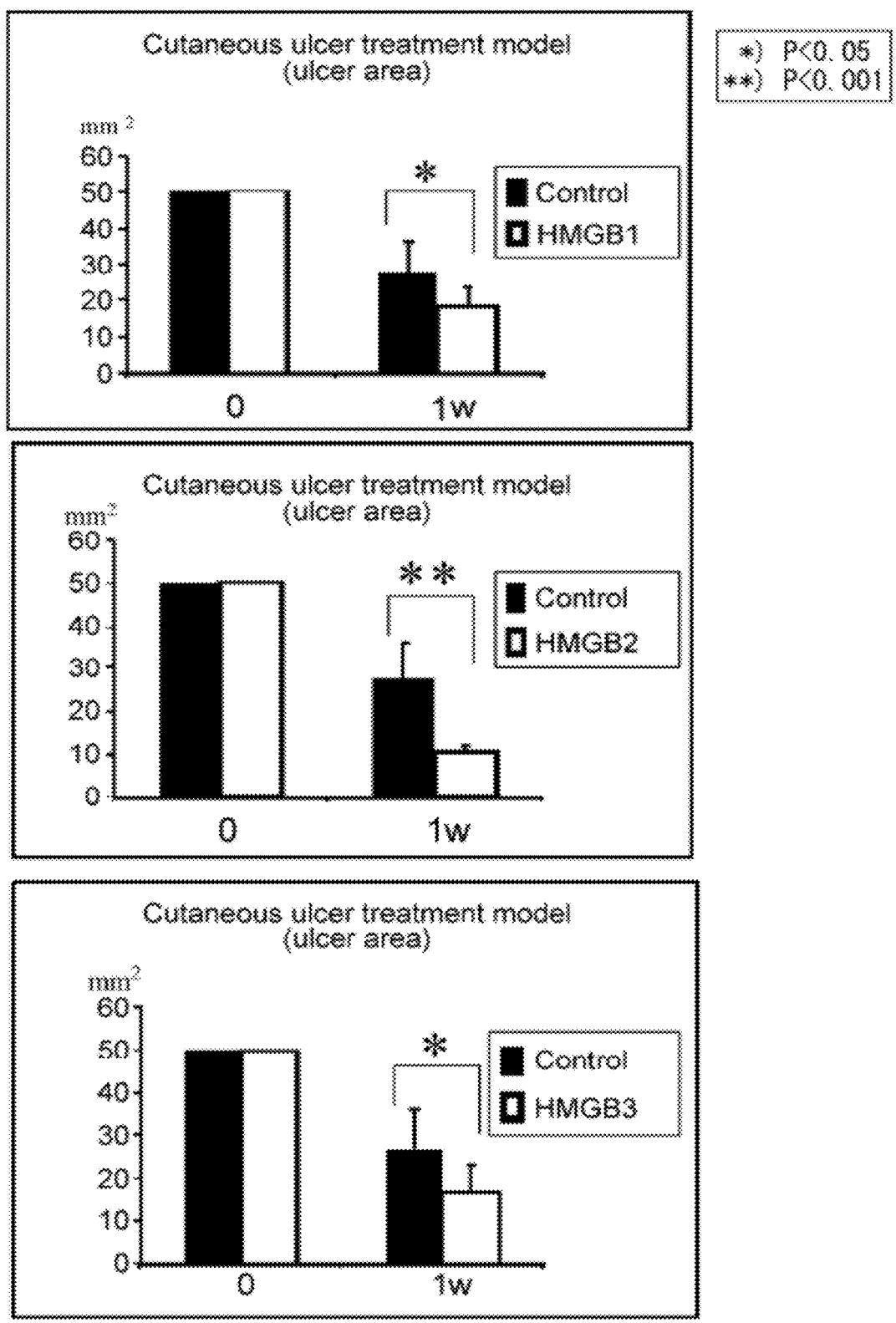
FIG. 23 presents a set of graphs showing the result of treatment on mouse cutaneous ulcer treatment models using HMGB family. HMGB1, HMGB2, and HMGB3 all showed significant effects on reducing the ulcer area as compared to control groups.
Figure 24:
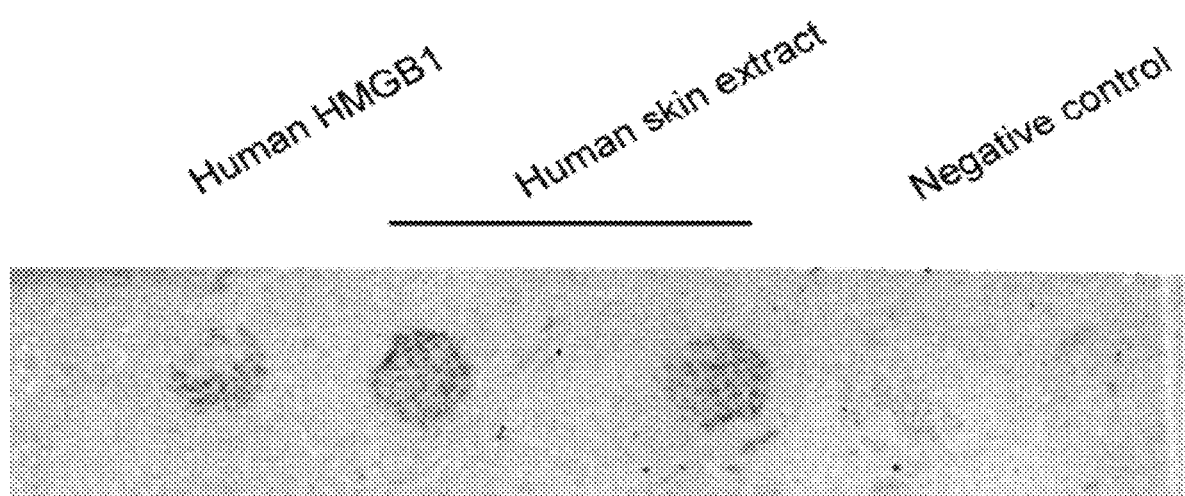
FIG. 24 presents a photograph showing the assessment of the activity of human HMGB1 and a human skin extract in inducing the migration of human bone marrow-derived mesenchymal stem cells, performed using a Boyden chamber.

Results: As a result of Western blotting, bands of HMGB2 and HMGB3 were detected as well as the HMGB1 band. Therefore, the neonatal mouse skin extract was confirmed to contain the family proteins, HMGB2 and HMGB3, besides HMGB1 (FIG. 19). Expression vectors of HMGB1/HMGB2/HMGB3 having a Flag tag added at the N-terminus of each protein, were prepared (FIG. 20). These expression vectors were introduced into HEK293 cells, and the expressed proteins were purified using the Flag tag, and Western blotting was carried out to observe these proteins (FIG. 21). The mouse bone marrow mesenchymal stem cell migration activity was measured using these purified proteins, and the activity was confirmed in all of the proteins (FIG. 22). The ulcer area produced in the back of the mouse was measured every 7 days, and a significant effect on reducing ulcer area was confirmed in the HMGB1, 2, and 3 treatment groups, as compared to the non-treatment group (FIG. 23). Similar to the mouse case, human HMGB1 and the human skin extract were revealed to have human bone marrow mesenchymal stem cell migration activity (FIG. 24).

Discussion: HMGB2 and HMGB3 are known as proteins having high homologies to HMGB1. These proteins are also expected to have properties similar to HMGB1. It was confirmed that HMGB2 and HMGB3 of the HMGB1 family are also produced from the extract of the free skin section. Further, HMGB1/HMGB2/HMGB3 recombinant proteins were produced, and their in vitro chemotactic activity for bone marrow mesenchymal stem cells and the in vivo therapeutic effect on a cutaneous ulcer were also confirmed. It was revealed that the HMGB family (HMGB1/HMGB2/HMGB3) and the recombinant HMGB family in the neonatal mouse free skin section have a bone marrow mesenchymal stem cell-attracting activity and an activity of locally attracting bone marrow-derived stem cells which are differentiable into epithelium, and that the thus attracted bone marrow-derived cells differentiate into various cells such as epidermal keratinocytes, hair follicles, and fibroblasts in the damaged tissue to promote the recovery of the damaged tissue. Moreover, since bone marrow mesenchymal stem cells are pluripotent stem cells, the present inventors believe that therapeutic effects can also be expected in the same manner by systematic administration or local administration of the HMGB family to treat damaged states in other tissues, for example, tissue damages such as brain injury, myocardial infarction, and bone fracture.

Moreover, it is known that, between human and mouse, amino acid sequence homology for HMGB1 is 98% (213/215), 96% (202/210) for HMGB2, and 97% (195/200) for HMGB3. Therefore, human HMGB and mouse HMGB are considered to have similar activities, and the results of the present Reference Examples revealed that human skin extract and human HMGB1 have bone marrow mesenchymal stem cell-attracting activities in the same manner as those of mouse skin extract and mouse HMGB1.

Reference Example 4

Objective: Establishment of a method of producing a tissue extract containing bone marrow mesenchymal stem cell-attracting factors.

Methods: Brain, heart, intestine, kidney, and liver of a 6-week-old C57BL6 mouse and skin of a neonatal mouse were immersed in 1 ml of physiological phosphate buffer solution (PBS) at pH 7.4. The solutions were incubated at 4° C. for 24 hours, and then centrifuged at 440 G at 4° C. for 10 minutes to remove the tissues. The supernatants were collected to prepare tissue extracts. To confirm whether the thus obtained extract has a bone marrow-derived mesenchymal stem cell-attracting activity, its migration-inducing activity on bone marrow-derived mesenchymal stem cells was examined in the same manner as in [Reference Example 2] using a Boyden chamber. Moreover, the HMGB1 concentration contained in these samples was measured using an HMGB1 ELISA kit (Shino-Test). Further, tissue extracts of the brain, heart, and skin were allowed to bind to a heparin affinity column in the same manner as in [Reference Example 2], and the bone marrow-derived mesenchymal stem cell-attracting activity in the protein-bound fraction was confirmed using Boyden chamber.

Figure 25:
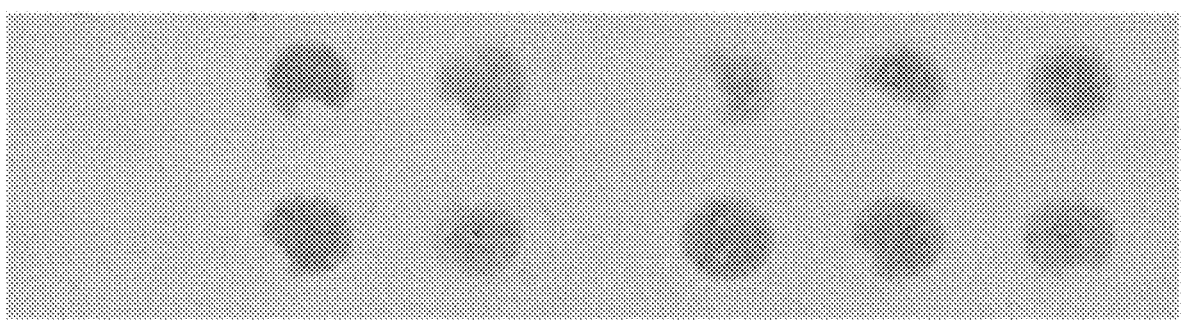
FIG. 25 presents a set of photographs showing the assessment of the activity of bone marrow mesenchymal stem cell-attracting substances in the heart, brain, and skin extracts of mouse, performed using a Boyden chamber after purifying the substances by a heparin column.
Figure 25:
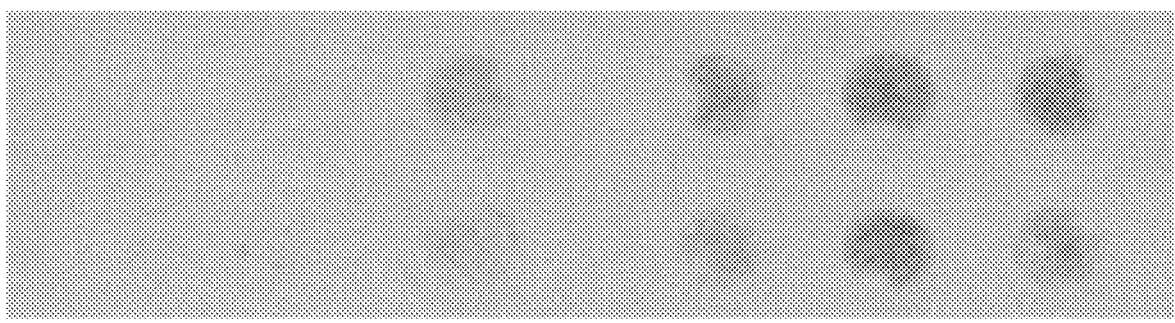

Results: The mouse brain extract contained an amount of HMGB1 equivalent to the neonatal mouse skin extract. Further, bone marrow mesenchymal stem cell-attracting activity was also observed in the mouse brain as well as in the skin. Although the mouse intestine extract and the mouse heart extract contained little HMGB1, bone marrow mesenchymal stem cell-attracting activities were observed. Moreover, the heparin column-bound fractions of mouse brain and mouse heart, as well as the heparin column-bound fraction of mouse skin, showed bone marrow mesenchymal stem cell-attracting activities (FIG. 25). Table 1 shows the measurement results of the HMGB1 concentration and the bone marrow mesenchymal stem cell-attracting activity in each of the mouse tissue extracts.

TABLE 1

| | HMGB1 concentration (ng/ml) | Bone marrow mesenchymal stem cell-attracting activity |
|---|---|---|
| Skin | 110 | Present |
| Brain | 140 | Present |

TABLE 1-continued

| | HMGB1 concentration (ng/ml) | Bone marrow mesenchymal stem cell-attracting activity |
|---|---|---|
| Heart | 4 | Present |
| Intestine | 0 | Present |
| Kidney | 115 | ND |
| Liver | 61 | ND |

ND: No data

Discussion: A method in which HMGB1 can be conveniently extracted not only from the skin but also from the brain was developed by simply immersing these organs in a physiological buffer. This method is also applicable to other organs such as liver and kidney. Moreover, although the extracts from intestine and heart contain little HMGB1, a bone marrow mesenchymal stem cell-attracting activity was observed. This suggests these extracts contain other bone marrow mesenchymal stem cell-attracting substance(s) apart from HMGB1. Such substances contained in these extracts are originally present in each tissue, and are considered to physiologically attract bone marrow mesenchymal stem cells to the damaged tissue when the tissue is damaged. The present invention developed a novel method for conveniently and functionally extracting multiple bone marrow mesenchymal stem cell-attracting substances including HMGB1, from various organs. Further, a method for purifying bone marrow mesenchymal stem cell-attracting substances from a tissue extract using the binding to the heparin column was also developed. These substances having bone marrow mesenchymal stem cell-attracting activities can be purified from the brain and heart in the same manner as in the skin using a heparin column.

Reference Example 5

Objective: Establishment of a method for extracting mesenchymal stem cell migration activators from cultured cells.

Methods: Human embryonic kidney derived cultured cell line HEK293 and human cervix carcinoma cell line HeLa were each cultured in 10% fetal bovine serum-containing D-MEM (Nacalai). These cells were each washed with PBS, and then $10^7$ cells were immersed in 5 ml of PBS (Nacalai) at 4° C. for 16 hours. The solution was centrifuged at 440 G (acceleration of gravity) at 4° C. for 5 minutes, and then the supernatant was collected. Human bone marrow mesenchymal stem cells were placed in the upper chamber of a Boyden chamber, and a 5-fold diluted (with DMEM) cell extract was placed in the lower chamber, to confirm the migration activity of human bone marrow mesenchymal stem cells.

Figure 26:
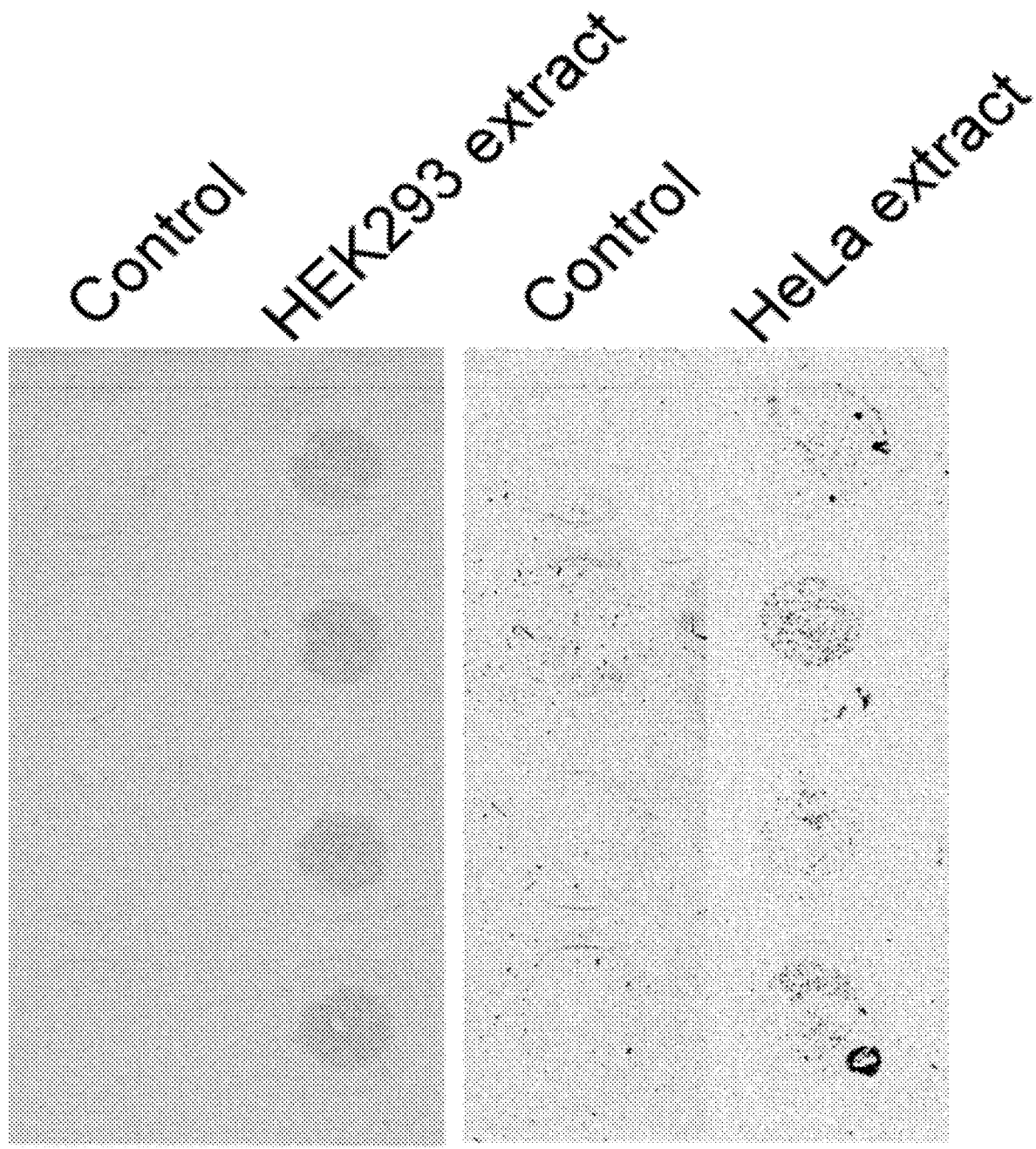
FIG. 26 presents a set of photographs showing the assessment of the activity of a HEK293 extract and a HeLa extract in inducing the migration of human bone marrow mesenchymal stem cells, performed using a Boyden chamber. Both cultured cell lines showed migrating activities on human bone marrow mesenchymal stem cells.

Results: HEK293 extract and HeLa extract both showed similar bone marrow mesenchymal stem cell migration activities (FIG. 26).

Discussion: Bone marrow mesenchymal stem cell migration activators were successfully extracted by the convenient method of immersing cultured cells in PBS.

Reference Example 6

Objective: Whether or not regeneration of neural cells can be induced is examined by producing mouse brain-defective models, to which a heparin-column purified fraction of skin extract is administered in a sustained-release manner at the local lesion site, by which stem cells contained in a mouse myeloid system is allowed to migrate into the local lesion site.

Methods:
(1) Preparation of Heparin-Column Purified Fraction of Skin Extract

An excised skin section of a neonatal mouse was incubated in PBS (mouse/ml) at 4° C. for 16 hours, and a skin extract was obtained. The skin extract was diluted 10-fold with 9 volumes of 20 mM phosphate buffer at pH 7.5 at 4° C. 20 mM phosphate buffer at pH 7.5 (30 ml) was poured into HiTrap Heparin HP column (column volume: 5 ml, GE Healthcare) in advance to equilibrate the column. The diluted solution was then allowed to bind to the column. Thereafter, the column was washed with 20 mM phosphate buffer at pH 7.5 and 100 mM NaCl (30 ml). To elute the adsorbed proteins, 20 mM phosphate buffer at pH 7.5 and 1000 mM NaCl were poured into the column, and the factions were eluted into the tubes. Each of the adsorbed factions was assessed for the chemotactic activity for mouse bone marrow-derived cells using the Boyden chamber method shown above, and fraction(s) having a chemotactic ability was collected. Solution(s) having this activity was used as a heparin purified fraction(s) of the skin extract in the experiment below.

(2) Production of Myelosuppressive Mice

Mice were irradiated with single-dose of X ray at 10 Gy to produce myelosuppressive mice.

(3) Transplant of GFP Mouse Bone Marrow to Myelosuppressive Mice

Bone marrow cells were collected from both femurs and crus bones of GFP mice. These cells were administered to the myelosuppressive mice through the caudal vein 24 hours after the irradiation. The administration was carried out under inhalational anesthesia using isoflurane.

(4) Production of a Brain-Defective (Brain Tissue-Defective) Mouse Model

Figure 27:
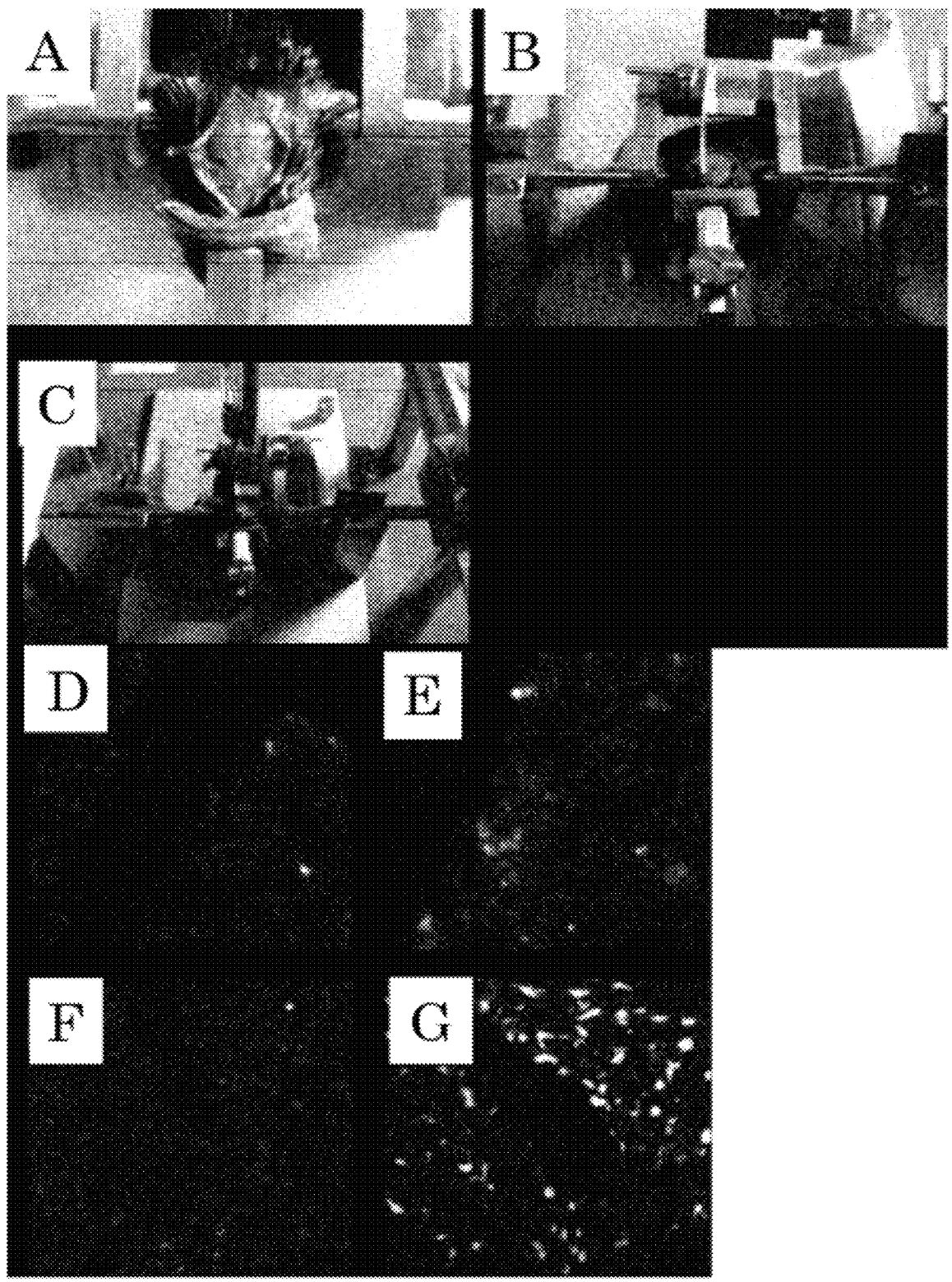
FIG. 27A is a photograph showing a mouse fixed to a brain stereotaxic apparatus and subjected to a midline incision in the head with a scalpel, followed by trepanation using a drill.
FIG. 27B is a photograph showing the brain to which a negative pressure is applied using a syringe to aspirate a part of the brain tissue.
FIG. 27C is a photograph after injection of 5 µl heparin-column purified fraction of a skin extract dissolved in fibrin adhesive formulation (fibrinogen) to the brain, and a subsequent injection of 5 µl of fibrin glue formulation (thrombin).
FIG. 27D and FIG. 27E are photographs of the brain injury model taken 2 weeks after the treatment. Higher accumulation of GFP-positive cells was observed in the treatment group using the heparin-column purified fraction of skin extract in E compared to the control in D.
FIG. 27F and FIG. 27G are photographs of the brain injury model taken 6 weeks after the treatment. Higher accumulation of GFP-positive cells was observed in the treatment group using the heparin-column purified fraction of skin extract in G compared to the control in F.

The myelosuppressive mice transplanted with GFP mouse bone marrow cells were subjected to inhalational anesthesia using isoflurane, and pentobarbital (45 mg/kg) was intraperitoneally injected to the mice. The mice were fixed onto a brain stereotaxis apparatus and subjected to a midline incision in the head with a scalpel. Trepanation was carried out at 2.5 min right-lateral and 12.5 mm anterior to the bregma using a drill (FIG. 27A). At a 3 mm depth from this site, a 20 G Surflow needle was inserted and fixed. Then, a negative pressure was applied using a syringe to suck apart of the brain tissue (FIG. 27B).

(5) Administration of a Heparin-Column Purified Fraction of Skin Extract to the Brain Tissue-Defective Site Five µl of a heparin-column purified fraction of skin extract dissolved in fibrinogen of a fibrin tissue adhesive formulation (Bolheal (Kaketsuken)) was injected to the above site, and subsequently, 5 µl of thrombin of a fibrin tissue adhesive formulation (Bolheal (Kaketsuken)) was injected using a Hamilton syringe and a 26 G syringe (FIG. 27C). The aim of this operation was to exert the sustained-release agent effect of a heparin-column-purified fraction of the skin extract.

(6) Assessment of the Effects of Neural Cell Regeneration in Brain Tissue-Defective Sites Mice of the control group and the treatment group were used for the assessment. An appropriate elapsed time setting (over time) was determined, the mice were perfused with 4% paraformaldehyde and fixed and then the brain was cut out. Further, external fixation was performed with 4% paraformaldehyde. These were then dehydrated in a 15% and 30% sucrose gradient to produce frozen sections.

The nucleus were stained with a DAPI (4',6-Diamidino-2-phenylindole, dihydrochloride) solution and the section was sealed using an anti-fading agent. The accumulation of GFP-positive cells in the lesion site (brain tissue-defective site) was assessed using a confocal laser microscope.

Results: The accumulation of GFP-positive cells is qualitatively shown for 2 weeks, and 6 weeks after the administration. The accumulation of GFP-positive cells tends to be higher in the lesion sites of the treatment group rather than the control group, for both 2 weeks (control; FIG. 27D, skin extract heparin-column-purified fraction; FIG. 27E) and 6 weeks (control; FIG. 27F, skin extract heparin-column-purified fraction; FIG. 27G) after the administration.

Discussion: The administration of the heparin-column-purified fraction of the skin extract resulted in the accumulation of bone marrow-derived cells in the brain tissue-defective site, which showed a nerve cell form. Bone marrow-derived mesenchymal stem cells are also known to differentiate into nerve cells and the result revealed that the heparin-column purified fraction of the skin extract is capable of inducing neural cell regeneration of the injured site in the brain. Moreover, this is also applicable to neuronal regeneration of damaged sites in brain tissues in cerebral ischemic diseases and cerebral contusions.

Reference Example 7

Purpose: Mobilization of bone marrow tissue stem cells to peripheral blood using bone marrow-derived tissue stem cell-attracting factors in skin tissue extract Methods: To achieve the above purpose, a study was conducted by the method described below.

(1) Preparation of a bone marrow-derived tissue stem cell attractant. Free skin pieces isolated from 25 neonatal mice (two days old) were immersed in 25 ml of phosphate buffered saline (PBS), pH 7.4. After 24 hours of incubation at 4° C., the sample was centrifuged at 440 G at 4° C. for ten minutes to remove the tissue. The supernatant was collected as skin extract (SE).

Meanwhile, RNA was extracted from neonatal C57/B16 mice skin using Trizol (Invitrogen), and then cDNA was synthesized using the SuperScript III cDNA Synthesis Kit (Invitrogen). Polymerase chain reaction (PCR) was carried out using this cDNA as a template to amplify HMGB1 cDNA. The HMGB1 cDNA was inserted into a mammalian cell protein expression plasmid vector, pCAGGS, to express a protein in which a Flag-tag sequence (Asp-Tyr-Lys-Asp-Asp-Asp-Lys, SEQ ID NO: 30) is attached to the N-terminus of its amino acid sequence (FIG. 20). The plasmid vector was transfected into HEK293 (cultured cell line derived from human fetal kidney cell). The cells were cultured for 48 hours to express the protein. Each sample of cells expressing the HMGB1 protein and the culture supernatant were incubated at 4° C. for 16 hours, and then centrifuged at 4,400×g for five minutes. The supernatant was collected, and anti-Flag Antibody Gel (Sigma) was added thereto in an amount of 100 µl per 50 ml of the supernatant. The mixture was incubated at 4° C. for 16 hours. The gel was collected by centrifugation, followed by five PBS washes. Then, the gel was eluted with 3× Flag peptide (final 100 µg/ml). The concentration of the eluted protein was determined using the HMGB1 ELISA Kit (Shino-Test Co.). After freeze-drying, the protein concentration was adjusted to 200 µg/ml with PBS.

Figure 28:
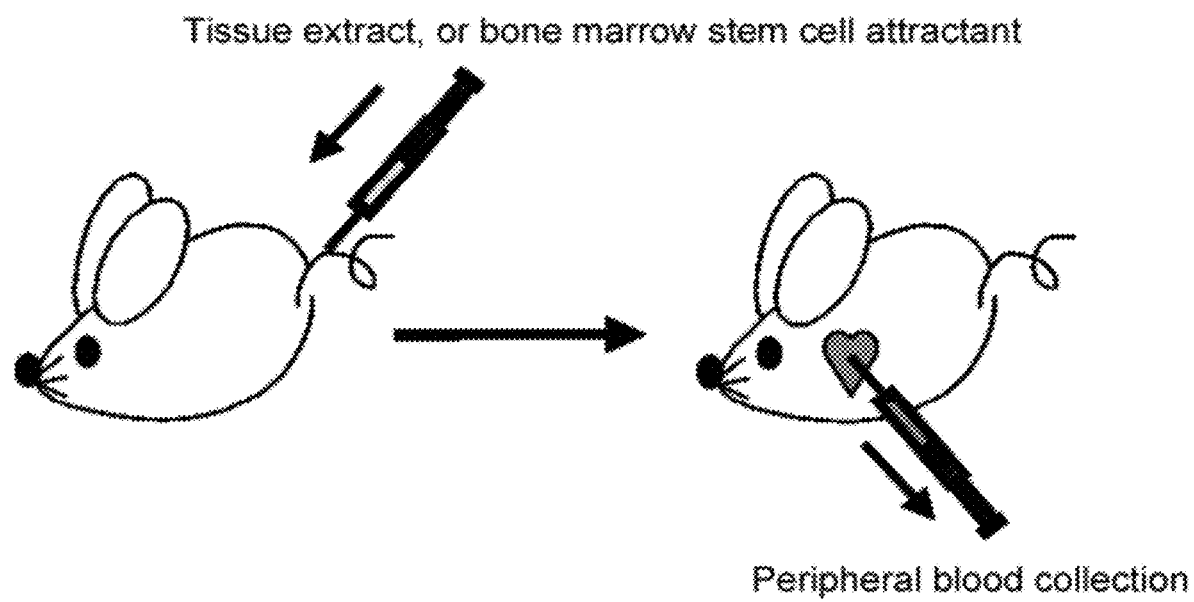
FIG. 28 is a diagram showing the administration of skin extract (SE) to a mouse via the caudal vein and the collection of peripheral blood.

(2) Eight-week-old male mice (C57/B16) were administered with 500 µl of the above-described skin extract (SE), or 500 µl of PBS as a negative control group, via the caudal vein using syringes attached with a 30 G ½ injection needle (FIG. 28). Six, 12, 24, and 48 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged using a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience), PE-labeled anti-mouse PDGFRβ antibody (e-Bioscience), and PerCy5-labeled anti-mouse CD44 antibody (BD biosciences). After incubation, the cells were centrifuged at 440×g at 25° C. for five minutes. The supernatant was removed. 400 µl of PBS containing 1% paraformaldehyde was added to the cells to prepare a sample for flow cytometric analysis.

Figure 29:
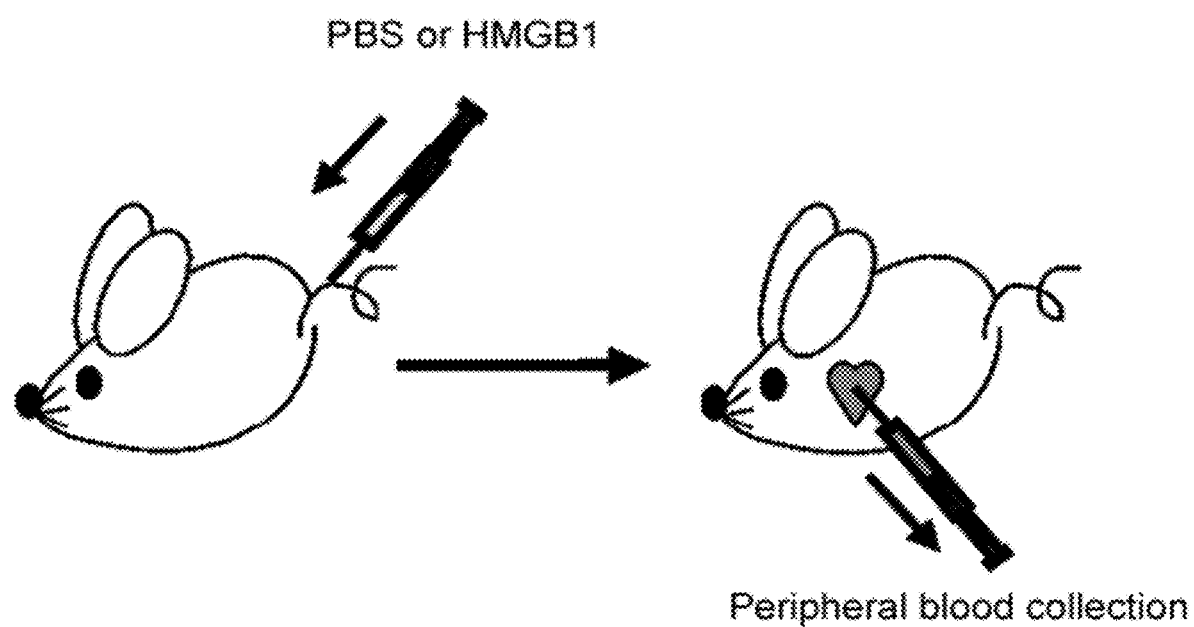
FIG. 29 is a diagram showing the administration of HMGB1 to a mouse via the caudal vein and the collection of peripheral blood.

Eight-week-old male mice (C57/Bl6) were administered with 250 µl of mouse HMGB1 (1 µg/µl), or 250 µl of PBS as a negative control group, via the caudal vein using syringes attached with a 30 G ½ injection needle (FIG. 29). 12 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged in a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience) and PerCy5-labeled anti-mouse CD44 antibody (BD biosciences). After incubation, the cells were centrifuged at 440×g at 25° C. for five minutes. The supernatant was removed. 400 µl of PBS containing 1% paraformaldehyde was added to the cells to prepare a sample for flow cytometric analysis.

Figure 30:
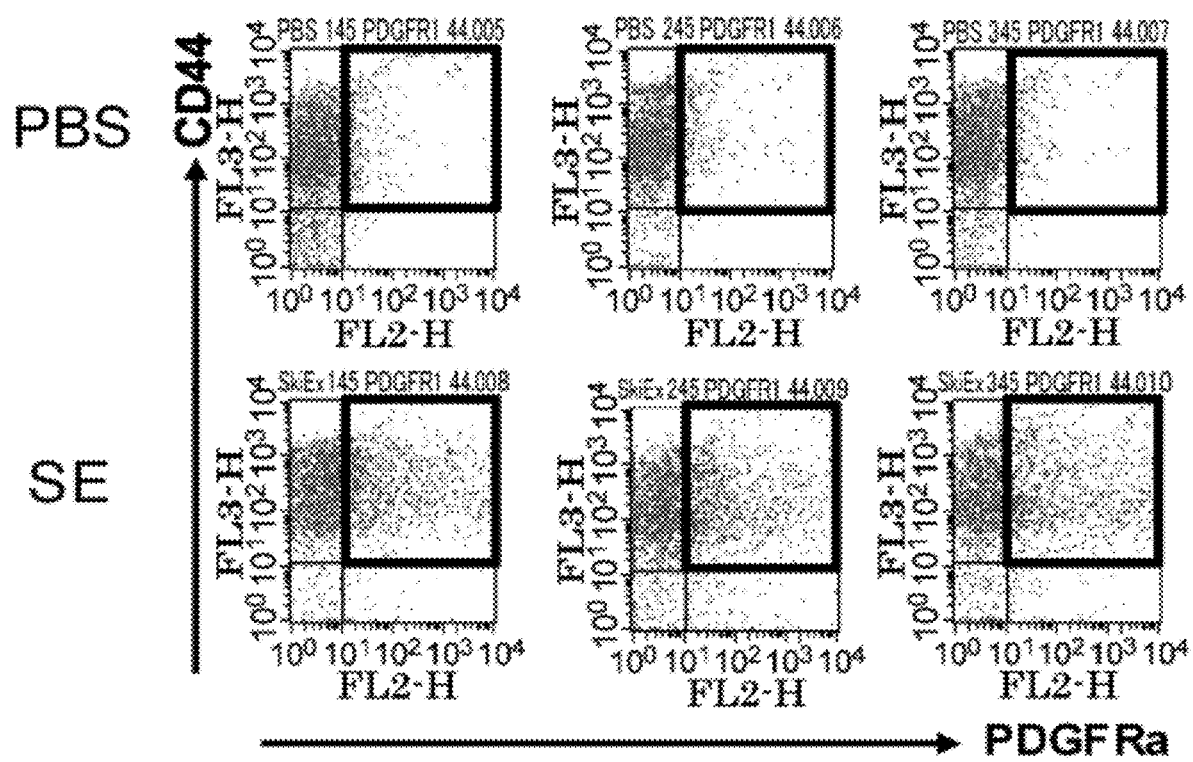
FIG. 30 is a set of diagrams showing the flow cytometric fractionation of mouse peripheral blood mononuclear cell fractions that were obtained after 12 hours of skin extract (SE) administration and then fluorescently labeled with anti-mouse PDGFRα antibody and anti-mouse CD44 antibody. The upper three panels show the PBS administration group as a negative control (n=3), and the lower three panels show the skin extract (SE) administration group (n=3). The vertical and horizontal axes indicate the expression levels of CD44 and PDGFRα, respectively. The area boxed with blue line corresponds to the CD44-positive, PDGFRα-positive cell population, which was increased in the skin extract administration group (SE) as compared to the PBS group.
Figure 31:
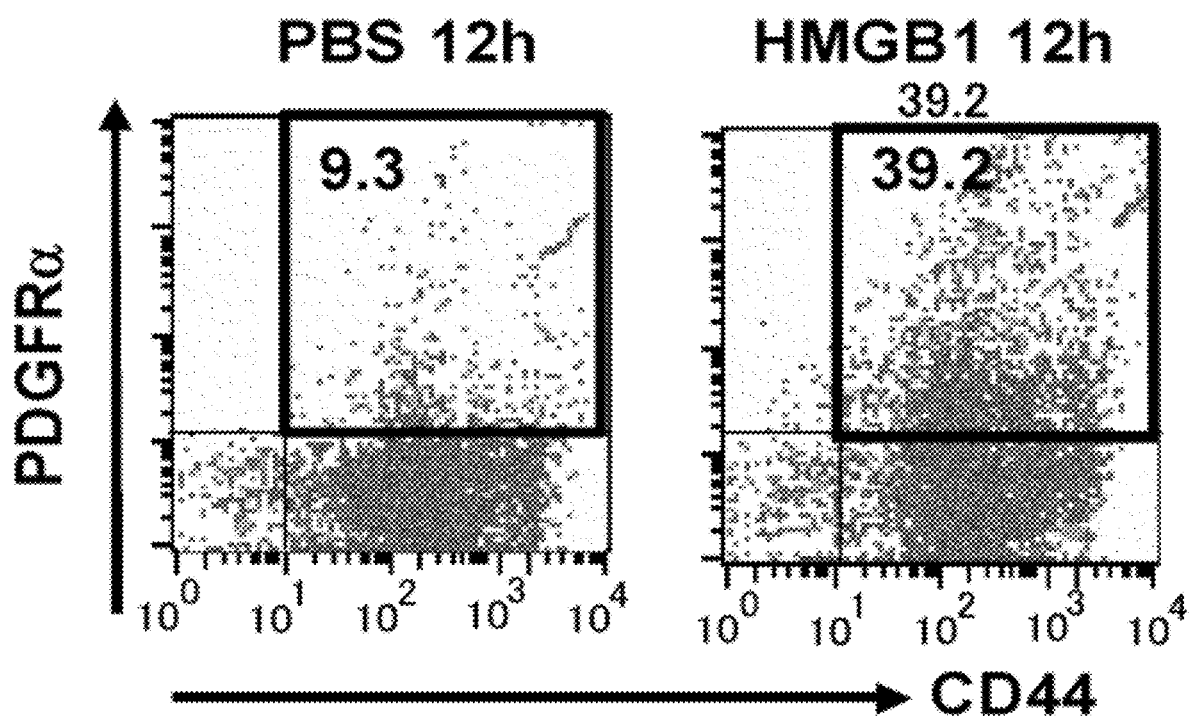
FIG. 31 is a set of diagrams showing the flow cytometric fractionation of mouse peripheral blood mononuclear cell fractions that were obtained after 12 hours of HMGB1 administration and then fluorescently labeled with anti-mouse PDGFRα antibody and anti-mouse CD44 antibody. The left panel shows PBS-administered mice as a negative control, and the right panel shows HMGB1-administered mice. The vertical and horizontal axes indicate the expression levels of CD44 and PDGFRα, respectively. The area boxed with blue line corresponds to the CD44-positive, PDGFRα-positive cell population, which was increased in the HMGB1-administered mice as compared to the PBS-administered mice.

Results: PDGFRα and CD44 double-positive cells were demonstrated to be significantly mobilized to peripheral blood 12 hours after injection of the skin extract (SE) (FIG. 30). Furthermore, PDGFRα and CD44 double-positive cells were demonstrated to be significantly mobilized to peripheral blood 12 hours after injection of HMGB1 (FIG. 31).

Reference Example 8

Purpose: To test whether mesenchymal stem cells are mobilized to peripheral blood by intravenous administration of recombinant HMGB1 protein.

Methods: C57BL6 mice (eight to ten weeks old, male) were administered with 400 µl of physiological saline containing 100 µg/ml recombinant HMGB1 protein (40 µg of HMGB1) or 400 µl of physiological saline alone through the caudal vein. After 12 hours, peripheral blood was collected from the mice. The blood samples were diluted with PBS to a total volume of 4 ml. The diluted blood samples were overlaid onto 3 ml of Ficoll-Paque Plus (GE) placed in centrifuge tubes. The samples were centrifuged at 400 G at 18° C. for 40 minutes. The middle layer containing mononuclear cells was transferred to a fresh centrifuge tube, and 45 ml of PBS was added thereto. The tube was centrifuged at 800 G at 18° C. for five minutes. The supernatant was removed. Again, 45 ml of PBS was added, and the tube was centrifuged at 800 G at 18° C. for five minutes. The supernatant was removed. The prepared mononuclear cells were incubated with Phycoerythrobilin (PE)-labeled anti-mouse PDGFRα; antibody and Fluorescein isothiocyanate (FITC)-labeled anti-mouse CD44 antibody. Then, the abundance of PDGFRα and CD44 double-positive cells in the mononuclear cell fraction was assessed by flow cytometry (Facscan; Becton, Dickinson and Company).

Figure 32:
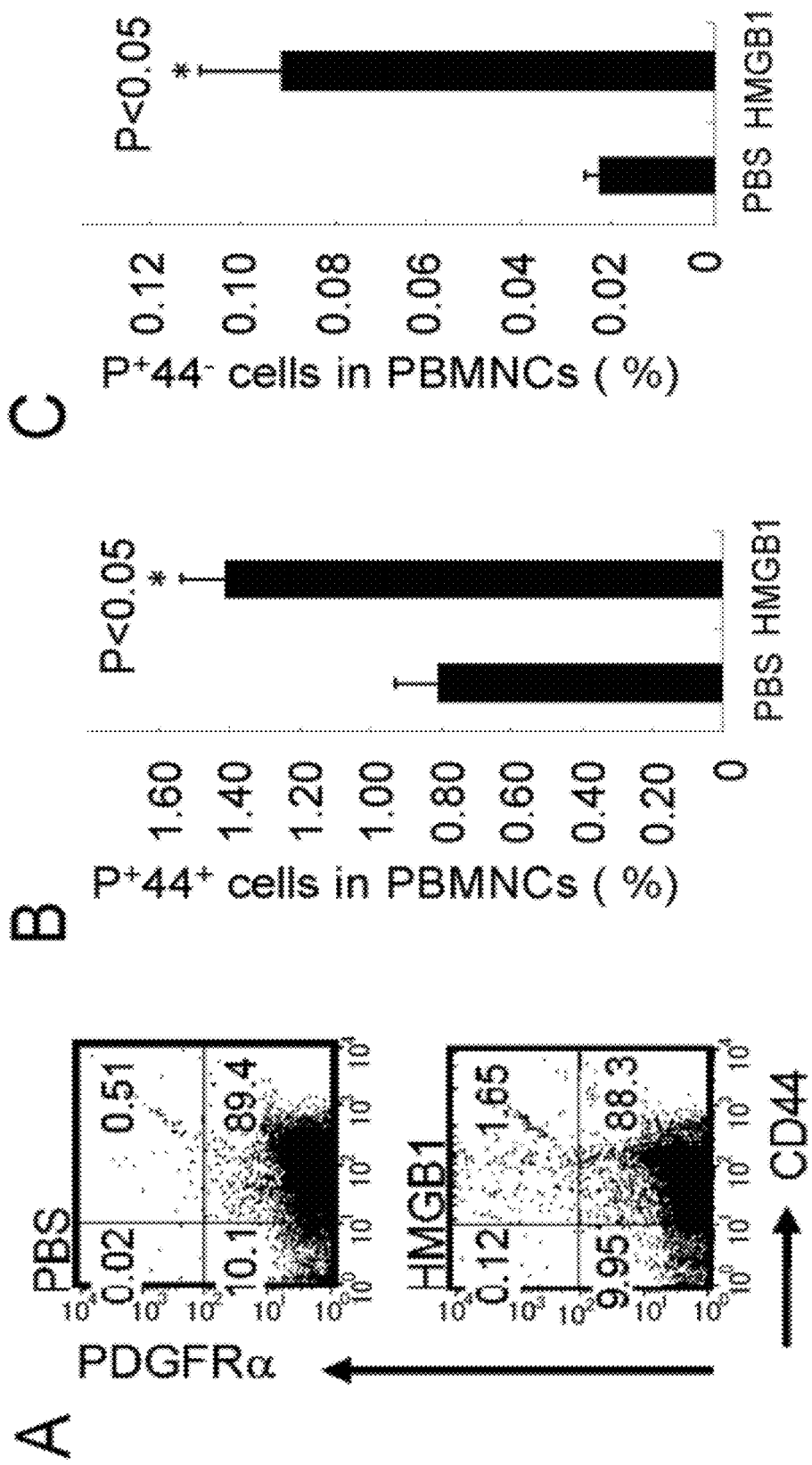
FIG. 32A shows in a diagram the flow cytometry result that shows the presence of cells having CD44 and PDGFRα. HMGB1 administration increased both populations of PDGFRα and CD44 double-positive cells, and PDGFRα-positive CD44-negative cells in peripheral blood.
FIGS. 32B and 32C show results of comparison between the PBS- and HMGB1-administered groups on the presence of PDGFRα and CD44 double-positive cells, and PDGFRα-positive CD44-negative cells in peripheral blood, respectively. Both cell populations were statistically significantly increased in the HMGB1-administered group.

Results: PDGFRα and CD44 double-positive cells, and PDGFRα-positive, CD44-negative cells in the peripheral blood mononuclear cell fraction were demonstrated to be significantly increased 12 hours after HMGB1 administration (FIG. 32). Specifically, HMGB1 was demonstrated to have the activity of mobilizing PDGFRα-positive cells to peripheral blood from bone marrow PDGFRα is known as a mesenchymal stem cell marker.

Discussion: PDGFRα and CD44 are known as surface markers of bone marrow mesenchymal stem cells, which are representative of bone marrow-derived pluripotent stem cells. Bone marrow mesenchymal stem cells are pluripotent stem cells capable of differentiating into nerve cells, epithelial cells, or such as well as osteocytes, chondrocytes, and adipocytes. Meanwhile, the skin pieces used in this experiment are in an ischemic condition. Thus, the tissues gradually necrotize and intracellular proteins such as nuclear proteins as well as cell surface proteins are released to the outside. HMGB1 is a protein contained in the skin extract. In skin grafting or the like, such proteins serve as a signal to mobilize bone marrow-derived tissue stem cells into grafted skin. It is thus speculated that functional skin regeneration is achieved in the skin graft due to reconstitution of epidermis, hypodermis, follicular tissues, or such stemmed from the bone marrow cells. Based on this experiment, the present invention for the first time successfully discovered that bone marrow-derived tissue stem cells are mobilized into peripheral blood circulation by intravenous administration of HMGB1 or skin extract as described above. This discovery enables new therapeutic methods for treating intractable diseases with tissue damages such as brain infarction, myocardial infarction, bone fracture, and cutaneous ulcer, which are based on mobilization of bone marrow-derived pluripotent stem cells into peripheral blood.

Reference Example 9

Purpose: To assess contribution of bone marrow-derived cells to the functional regeneration of in vivo grafted skin tissue Methods: Studies were conducted to achieve the above purpose.

(1) The degree at which bone marrow-derived cells contribute to the functional regeneration of grafted skin was assessed using a system of in vivo skin grafting in GFP bone marrow-transplanted mice. Specifically, male C57BL/6 mice (six to eight weeks old) were irradiated at a lethal dose (10 Gy), and green fluorescent protein (GFP) transgenic mouse-derived bone marrow cells ($5 \times 10^6$ cells/0.1 ml of physiological phosphate buffered saline, pH 7.4) were transplanted into the mice via the caudal vein immediately after the irradiation.

(2) After the engraftment of transplanted bone marrow cells (six weeks) was confirmed, neonatal mouse (female) skin was transplanted to the dorsal skin of the resulting GFP bone marrow-transplanted mice.

(3) After confirming the engraftment of grafted skin and sufficient skin tissue regeneration (four weeks), the degree of GFP fluorescence accumulation in the area of grafted skin was observed under a fluorescence stereomicroscope.

(4) The grafted skin was obtained by biopsy under inhalation anesthesia. Skin cryosections (6 µm) were prepared using a microtome with cooling apparatus, and fixed for 30 minutes with 4% paraformaldehyde. Then, cell nuclei in the tissues were stained with DAPI. After mounting the tissue using a mounting medium containing an anti-fading agent, the tissues were observed under a confocal laser microscope to assess the presence of GFP-positive bone marrow-derived cells.

Figure 33:
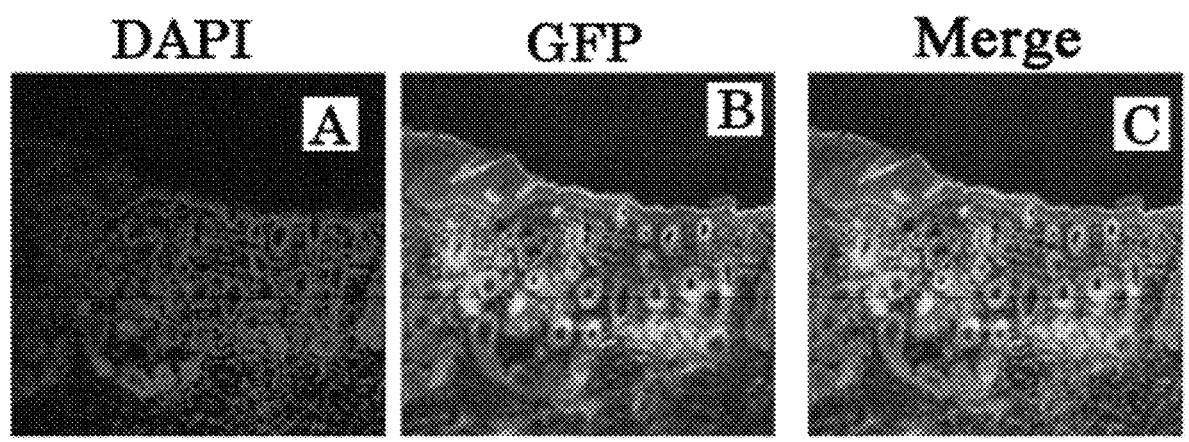
FIG. 33 shows in a set of photographs the accumulation of GFP fluorescence in grafted skin observed after skin is grafted onto the back of GFP bone marrow-transplanted mice. The left photograph (A) shows nuclear staining with DAPI. The middle photograph (B) shows green fluorescence of GFP-positive bone marrow-derived cells accumulated at the skin graft site. The right photograph (C) shows a merged image of photographs (A) and (B). Bone marrow-derived cells are reconstructing skin tissues.

Results: In the system of in vivo skin grafting in GFP bone marrow-transplanted mice, GFP fluorescence was observed in the majority of epidermal keratinocytes and dermal fibroblasts as well as smooth muscle cells and adipocytes of the regenerated skin tissues, suggesting that these cells were derived from the bone marrow (FIG. 33). Specifically, bone marrow-derived stem cells served as a source for most of the epithelial cells and mesenchymal cells required for the functional regeneration of the grafted skins.

Discussion: The results described above suggest that upon skin damage, bone marrow cells accumulate at the damaged site and differentiate into various types of organs constituting the skin, thereby contributing to functional regeneration of the skin. Meanwhile, it is speculated that the grafted skin contains substances that attract bone marrow cells which are capable of differentiating into various types of organs.

It has been reported that bone marrow contains two types of stem cell systems: hematopoietic stem cells and mesenchymal stem cells. It would be difficult to anticipate that a large number of bone marrow-derived epithelial cells and mesenchymal cells mobilized into the grafted skin are provided by bone marrow-derived hematopoietic stem cells as shown by the present research. This strongly suggests the possibility that bone marrow-derived mesenchymal stem cells contribute to the functional regeneration of grafted tissues. Specifically, it is anticipated that immediately after skin grafting, factors that mobilize bone marrow-derived mesenchymal stem cells are released from the grafted skin in a state of hemostasis/necrosis, and mobilize mesenchymal stem cells to the grafted skin from bone marrow via the peripheral blood circulation, thereby inducing functional regeneration of the skin tissue.

Reference Example 10

Purpose: To identify bone marrow-derived tissue stem cell-attracting factors in skin tissue extracts Methods: By the method described below, study was conducted to identify factors responsible for mobilizing bone marrow mesenchymal stem cells, which were predicted to be released from excised skin under hemostatic condition.

(1) Bone marrow cells were harvested from the thighbones or crural bones of C57BL/6 mice to obtain mouse bone marrow-derived mesenchymal stem cells. The cells were seeded into a cell culture dish with D-MEM (Nacalai) supplemented with 10% fetal bovine serum as a culture medium and cultured at 37° C. under 5% carbon dioxide gas. When the cells were grown to occupy an area of 70 to 100% relative to the bottom of the culture dish, the cells were detached from the culture dish using 0.25% trypsin/1 mM EDTA (Nacalai). The cells were then passaged under the same culture conditions. After at least five passages, the adherent cells were isolated and further cultured, and analyzed for cell surface antigens by flow cytometry. The result showed that the cells were positive for CD44 and Sca-1, and negative for Lin, CD45, and c-kit. It was confirmed that the cells can differentiate into osteocytes and adipocytes and thus have the characteristics of bone marrow mesenchymal stem cells.

(2) Free skin pieces isolated from five heads of neonatal mice (two-day-old) were immersed in 5 ml of physiological phosphate buffered saline (PBS, pH 7.4). After 24 hours of incubation at 4° C., the sample was centrifuged at 440 G at 4° C. for ten minutes to remove tissues. The supernatant was collected as skin extract. In addition, in the same way, free skin pieces isolated from a six-week-old mouse were immersed in 5 ml of physiological phosphate buffered saline (PBS, pH 7.4). After incubation at 4° C. for 24 hours, the samples were centrifuged at 440 G at 4° C. for ten minutes to remove tissues. The supernatants were collected as skin extract.

Figure 34:
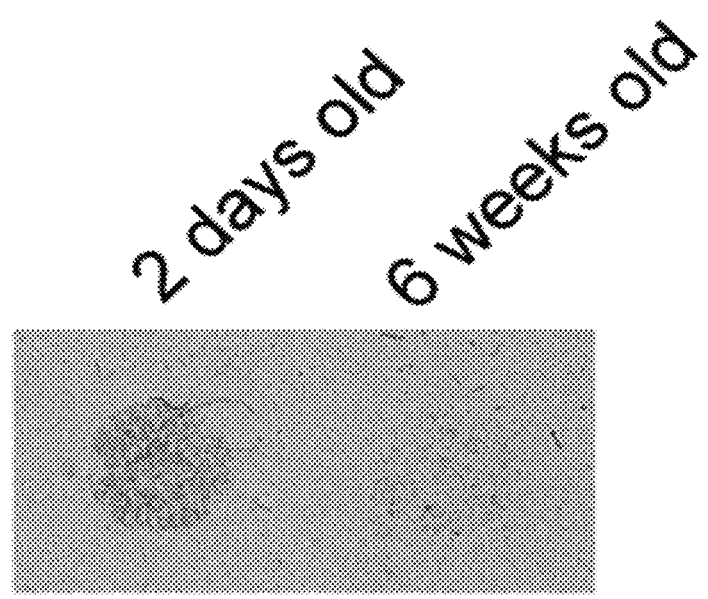
FIG. 34 is a photograph showing the result of assaying the migratory activity of bone-marrow derived mesenchymal stem cells in skin extracts using a Boyden chamber. The image shows blue-stained bone marrow mesenchymal stem cells that migrated from the upper compartment of the Boyden chamber through a 8-μm micropore polycarbonate membrane filter into the lower compartment containing skin extracts, and adhered to the lower-compartment side of the membrane. Skin extracts collected from two-day-old or six-week-old mice were placed in the lower chambers.

(3) To confirm whether the prepared skin extract has the activity of attracting bone marrow mesenchymal stem cells, the present inventors used the Boyden chamber to examine the chemotactic activity for previously cloned bone marrow-derived mesenchymal cells derived from C57BL6 mice. Specifically, a mixture of DMEM (20 µl) and skin extract (5 µl) from two-day-old or six-week-old mice was added into the bottom compartment (a volume of 25 of a Boyden chamber, and a polycarbonate membrane with 8-µm micropores was placed on top. Then, the upper compartment (a volume of 50 µl) of the Boyden chamber was placed in contact with the membrane, and a suspension of bone marrow-derived mesenchymal stem cells ($5 \times 10^4$ cells/50 ml of culture medium (DMEM supplemented with 10% fetal bovine serum)) was added to the upper compartment. The chamber was incubated in a $CO_2$ incubator at 37° C. for four to 24 hours. After incubation, the upper unit of the chamber was removed. The thin silicone film was detached and the number of bone marrow-derived mesenchymal stem cells migrating into the bottom compartment through the micropores was quantitatively determined by staining the cells (FIG. 34).

Figure 35:
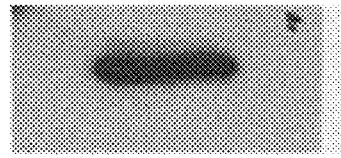
FIG. 35 shows in a set of photographs Western blot detection of the S100A8 and S100A9 proteins in skin extracts.
Figure 35:
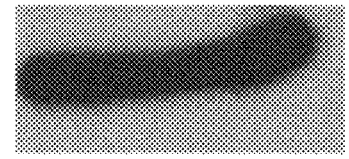

(4) About 2-cm$^2$ skin specimens were excised from two-day-old and six-week-old mice and immediately frozen in liquid nitrogen. The skin specimens were crushed in a mortar. RNAs were extracted and purified from the samples using RNeasy (Qiagen). Using the purified RNAs, microarray assay was carried out to screen for mRNA expressed at higher levels in the two-day-old mice. 767 genes showed two or more times greater scores in the two-day-old mice. Of these genes, proteins with high affinity for heparin, potential secretory proteins, and genes whose scores were six or more times greater in the two-day-old mice were examined and S100A9 was found as the 57$^{th}$ gene from the top. Thus, S100A9 and S100A8, which is known to form a heterodimer with S100A9, in the skin extract from the two-day-old mice were detected by Western blotting. Specifically, 5 µl of the skin extract from the two-day-old mice was combined with 5 µl of SDS-PAGE sample buffer (Bio-Rad). The mixture was heated in a heat block at 98° C. for five minutes, and then cooled to 25° C. The resulting sample was applied onto 12.5% acrylamide gel e-PAGEL (ATTO) and electrophoresed at 40 mA for 75 minutes using an electrophoretic device (ATTO). The gel was collected after electrophoresis. Using a blotting device (ATTO), proteins in the gel were transferred to PVDF membrane (7 cm by 9 cm, Millipore) pretreated with 100% methanol. After 75 minutes of protein transfer at 120 mA, the PVDF membrane was removed and shaken at room temperature for 30 minutes in PBS (Nacalai) containing 4% skim milk. Then, the removed PVDF membrane was soaked in 5 µl of anti-3100A8 antibody (R&D) or anti-S100A9 antibody (R&D) each diluted with 10 ml of PBS containing 4% skim milk, and shaken at room temperature for 60 minutes. After the antibody solution was removed, the membrane was shaken in 30 ml of PBS containing 0.1% Tween20 at room temperature for five minutes. This washing was repeated five times. Then, the membrane was soaked in 5 µl of HRP-labeled anti-goat IgG antibody (GE healthcare) diluted with 10 ml of PBS containing 4% skim milk, and shaken at room temperature for 45 minutes. After the antibody solution was removed, the membrane was washed with 30 ml of PBS containing 0.1% Tween20 at room temperature for five minutes while shaking. This washing was repeated five times. The membrane was treated for luminescence using ECL Detection Kit (GE healthcare), and then exposed on a film. Signals for S100A8 and S100A9 proteins were gained by developing the film in a developing apparatus (FIG. 35).

Figure 36:
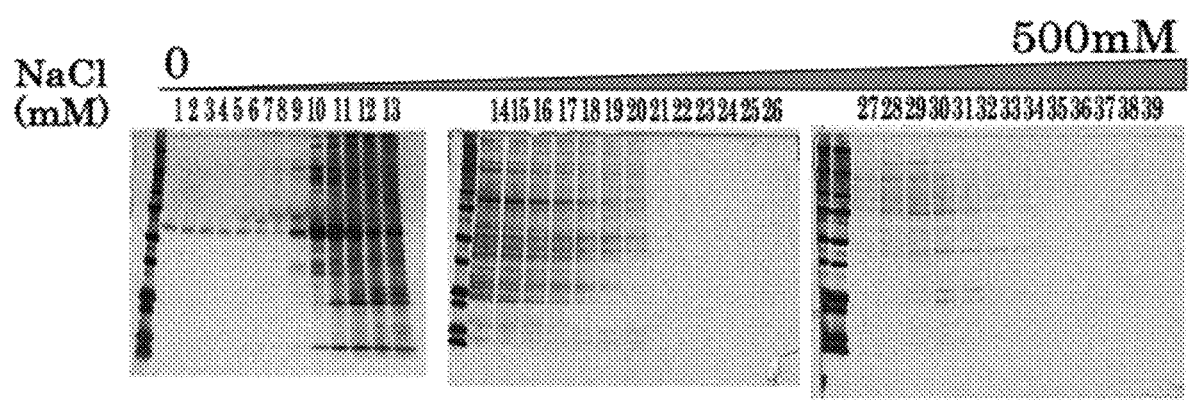
FIG. 36 shows in a photograph elution of a heparin-binding protein in skin extracts eluted from a heparin affinity column by a concentration gradient of NaCl. Proteins in each fraction were separated by SDS-PAGE and detected by silver staining.

(5) Factors having the activity of mobilizing bone marrow-derived mesenchymal stem cells in skin extracts were purified by heparin affinity column chromatography. The experiment described below was carried out using an FPLC device (GE healthcare). First, the skin extract of two-day-old mice was diluted 10-fold with nine volumes of 20 mM phosphate buffer (pH 7.5) at 4° C. (dilution solution A). 300 ml of 20 mM phosphate buffer (pH 7.5) was run through a HiPrep 16/10 Heparin FF (GE Healthcare) column to equilibrate the column in advance, and dilution solution A was loaded onto the column. Then, the column was washed with 300 ml of 20 mM phosphate buffer (pH 7.5). 20 mM phosphate buffer (pH 7.5) containing 10 mM NaCl (solution A) and 20 mM phosphate buffer (pH 7.5) containing 500 mM NaCl (solution B) were prepared to elute the adsorbed protein. Elution was started with [100% solution A+0% solution B], and then the proportion of solution B was gradually increased. Finally, the column was eluted with [0% solution A+100% solution B]. The total elution volume was 150 ml. The eluate was fractionated into silicone-coated tubes (3 ml/tube). 5 µl each of the fractionated samples were mixed with 5 µl of SDS-PAGE sample buffer (Bio-Rad). The mixtures were heated in a heat block at 98° C. for five minutes, and then cooled to 25° C. The samples were applied onto an acrylamide gel e-PAGEL (5-20% gradient, ATTO), and electrophoresed at 40 in A for 75 minutes using an electrophoresis device. After the electrophoresis, the electrophoresed protein was detected using the Dodeca Silver Stain Kit (Bio-Rad) (FIG. 36).

Figure 37:
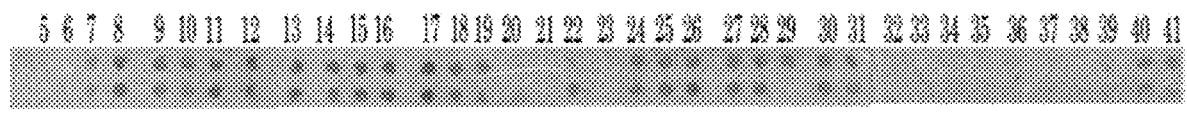
FIG. 37 shows in a photograph assay results of measuring the migratory activity of bone marrow-derived mesenchymal stem cells in skin extracts using a Boyden chamber. The image shows blue-stained bone marrow mesenchymal stem cells, which have migrated from the upper compartment of the Boyden chamber through the micropores of a filter to each heparin-binding fraction in skin extracts (to the lower compartment), and adhered to the lower-compartment side of the membrane.

The chemotactic activity of fractionated samples was assayed in the same way as described above using a Boyden chamber (FIG. 37).

Figure 38:
FIG. 38 shows in a set of photographs Western blot detection of the S100A8 and S100A9 proteins in each heparin-binding fraction of skin extracts.
Figure 38:

The presence of S100A8 and S100A9 proteins in the fractionated samples was detected in the same way as described above by Western blotting (FIG. 38).

Figure 40:
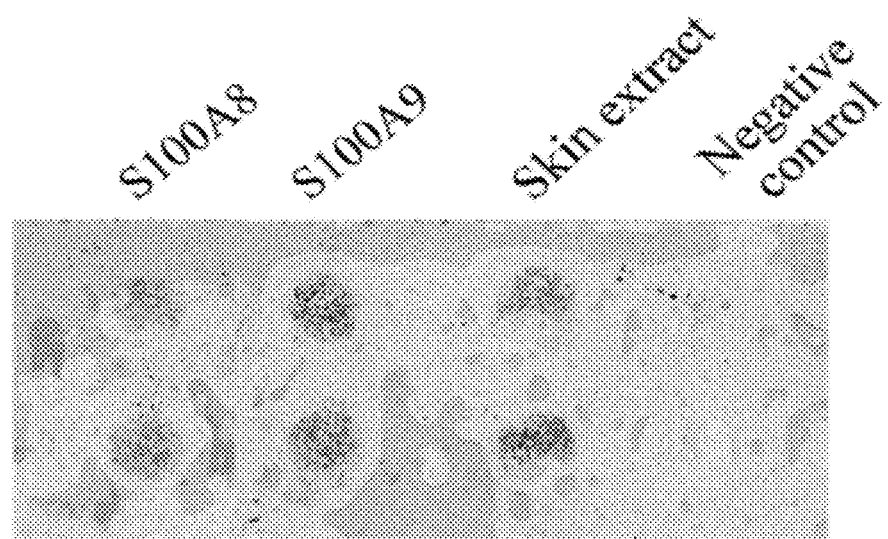
FIG. 40 shows a photograph showing the result of assaying the migratory activity of bone marrow-derived mesenchymal stem cells in skin extracts using a Boyden chamber. These images show blue-stained bone marrow mesenchymal stem cells, which have migrated from the upper compartment of the Boyden chamber through the micropores of a filter into the lower compartment containing recombinant GST-S100A8, GST-S100A9, or skin extracts, and adhered to the lower-compartment side of the membrane.

(6) RNA was extracted from neonatal mouse skin using Trizol (Invitrogen), and then cDNA was synthesized from the RNA using the SuperScript III cDNA Synthesis Kit (Invitrogen). cDNAs of S100A8 and S100A9 were amplified by the polymerase chain reaction (PCR) method using the cDNA as a template. These cDNAs were each inserted into a mammalian cell protein-expression plasmid vector, pCAGGS, to express the proteins in which a GST-tag sequence (amino acid sequence/SEQ ID NO: 31; DNA sequence/SEQ ID NO: 32) is attached to the N-terminus of their amino acid sequences (FIG. 39). pCAGGS-GST-S100A8 or pCAGGS-GST-S100A9 were each transfected into a human fetal kidney cell-derived cultured cell line HEK293 using a lipofection reagent (Invitrogen). 48 hours after transfection, the cells and culture supernatant were collected, and centrifuged at 4,400 G at 4° C. for five minutes. The supernatant (Supernatant A) and cells were collected separately. PBS containing 0.1% Tween20 was added to the cells, and the suspension was sonicated on ice for 30 seconds to disrupt the cell membrane. After centrifugation at 4,400×g at 4° C. for five minutes, the resulting supernatant was collected (Supernatant B). Supernatants A and B were combined together and loaded onto a HiTrap GST FF column (5 ml; GE Healthcare) whose buffer had been replaced with 30 ml of PBS in advance. After loading, the column was washed with 100 ml of PBS, and the adsorbed protein was eluted with 20 mM phosphate buffer (pH 8) containing reduced glutathione. The chemotactic activity of recombinant S100A8 and S100A9 for bone marrow mesenchymal stem cells was assessed using the Boyden chamber. The samples were prepared by dissolving purified S100A8 or S100A9 protein at 0.1 ng/µl in DMEM, or by diluting the skin extract of two-day-old mice with four volumes of DMEM, and added into the bottom compartment of the Boyden chamber. A negative control prepared as follows was used the same way: protein was extracted from cells transfected with a control vector which does not carry the cDNA of S100A8 or S100A9 as an insert; and then a fraction was eluted from a HiTrap GST FF column. After a sample was added into the bottom compartment, a polycarbonate membrane with 8-µm micropores was placed on top. Then, the upper unit (a volume of 50 µl) of Boyden chamber was placed in contact with the membrane, and a suspension of bone marrow-derived mesenchymal stem cells ($5 \times 10^4$ cells/50 ml of culture medium (DMEM supplemented with 10% fetal bovine serum)) was added to the upper chamber. The chamber was incubated in a $CO_2$ incubator at 37° C. for four to 24 hours. After incubation, the upper unit of the chamber was removed. The polycarbonate membrane was detached and the number of bone marrow-derived mesenchymal stem cells migrating into the bottom compartment through the micropores was quantitatively determined by staining the cells (FIG. 40).

(7) Eight-week-old male mice were injected with 250 µl of the above-described purified GST-S100A8 or S100A9 recombinant proteins (1 ng/µl) via the caudal vein. 12 hours after injection 1 ml of peripheral blood was collected from the hearts of the mice under inhalation anesthesia with isoflurane using a 1-ml heparin-coated syringe. The blood samples were each combined with 3 ml of PBS, and then gently overlaid onto 3 ml of Ficoll (GE healthcare). The resulting samples were centrifuged using centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells, and the cells were incubated at room temperature for five minutes. This hemolytic treatment was repeated twice. After adding 10 ml of PBS, the cells were centrifuged at 440×g at 25° C. for five minutes. The resulting supernatants were removed, and the cells were collected. 1,000,000 cells were incubated at room temperature for 20 minutes with a PE-labeled anti-mouse PDGFRα antibody (e-Bioscience), PE-labeled anti-mouse PDGFRβ antibody (e-Bioscience), FITC-labeled anti-mouse CD45 antibody (BD biosciences), and PerCy5-labeled anti-mouse CD44 antibody (BD biosciences), each diluted 100-fold with PBS. Then, the cells were centrifuged at 440×g at 25° C. for five minutes. The supernatants were removed. 400 μl of PBS containing 1% paraformaldehyde was added to the cells to prepare samples for flow cytometric analysis. Antibodies were used in the following combinations:

(I) PDGFRα/CD45/CD44
(II) PDGFβ/CD45/CD44

The ratio of cells expressing PDGFRα (or f) and CD44 to cells that were weakly positive or negative for CD45 was determined based on the analysis result (FIGS. 41A and B).

Figure 41:
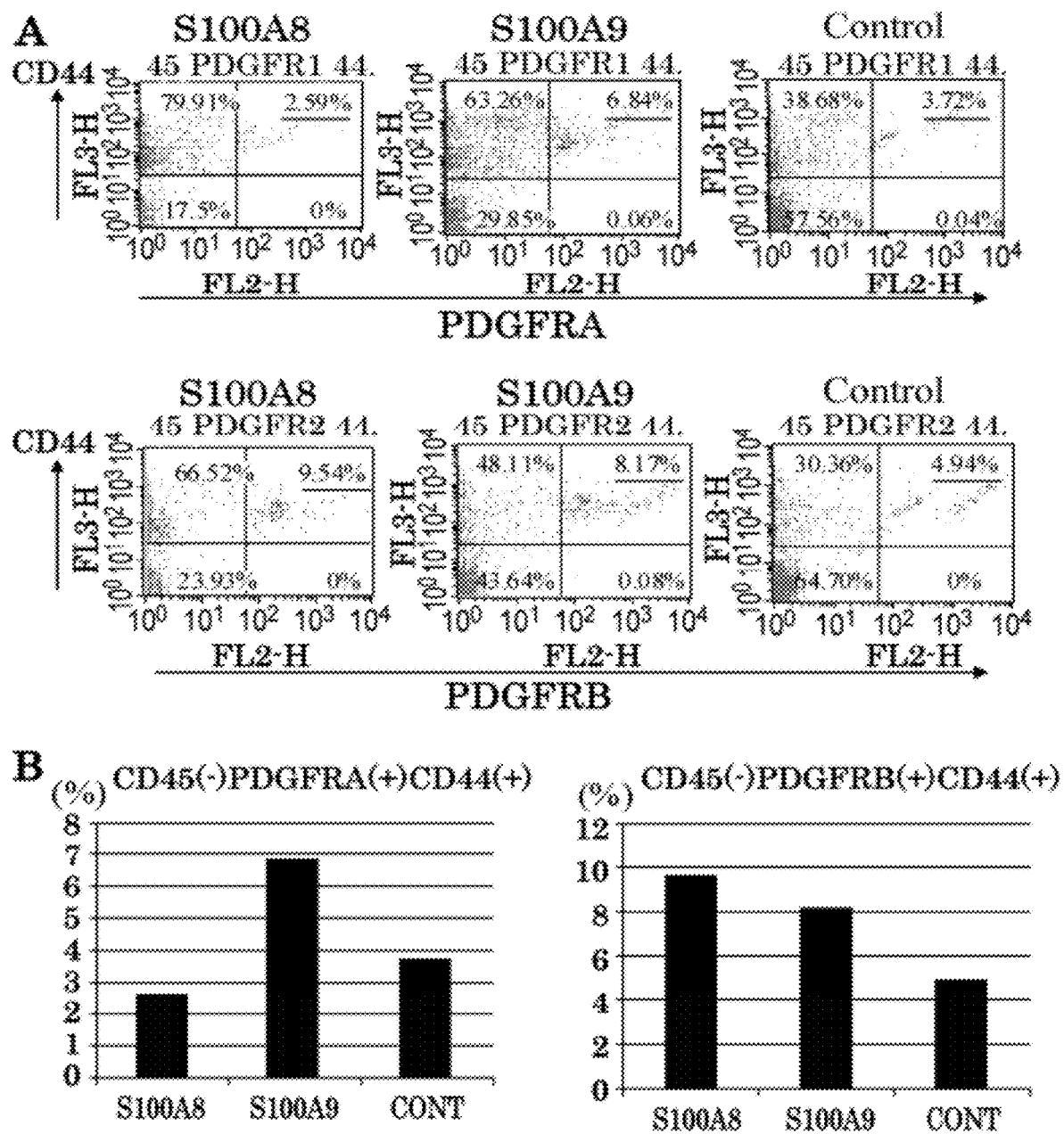
FIG. 41A presents a set of diagrams showing a FACS result for CD44, PDGFRα, and PDGFRβ in the CD45-negative cell fraction in peripheral blood 12 hours after administration of GST-S100A8 or GST-S100A9 via the mouse caudal vein.
FIG. 41B presents a set of graphs by quantitatively analyzing the population of CD45-negative, CD44-positive, PDGFRα-positive cells (left), or CD45-negative, CD44-positive, PDGFRβ-positive cells (right).

Results: Skin samples excised from two-day-old and six-week-old mice were assessed for the activity of mobilizing bone marrow mesenchymal stem cells. The activity of skin extract from two-day-old mice was demonstrated to be stronger than that of the skin extract from six-week-old mouse. Strong S100A9 expression in the skin from two-day-old mice was found by DNA microarray analysis. Crude samples of skin extracts purified on a heparin column exhibited correlation between the migrating activity of mesenchymal stem cells and the contents of S100A9 and S100A8. Expression vectors for these proteins were constructed, and the recombinant proteins were produced using HEK293 and purified. The migrating activity of bone marrow mesenchymal stem cells was confirmed in the purified S100A8 and S100A9 samples by assays using Boyden chamber. Furthermore, when intravenously administered to mice, the proteins also exhibited the activity of mobilizing a population of PDGFRα and CD44 double-positive cells to peripheral blood (FIG. 41).

Discussion: The present inventors for the first time in the world discovered in the present invention that free skin pieces produce S100A8 and S100A9, and the produced S100A8 and S100A9 proteins had strong activities of mobilizing bone marrow-derived mesenchymal stem cells. Meanwhile, bone marrow mesenchymal stem cells are known as pluripotent stem cells that differentiate into bone tissues, adipose tissues, cartilage tissues, fibroblasts, and the like. Recently, it has been indicated that bone marrow-derived cells also include pluripotent stem cells that differentiate into tissues such as cardiac muscle, nerve cells, and epidermal cells. Since the present invention demonstrates that the epidermal cells, hair follicle cells, fibroblasts of subcutaneous tissues, and such in the grafted skin are constituted by bone marrow-derived cells, S100A8 and S100A9 can be speculated to be responsible for mobilizing bone marrow-derived tissue stem cells to the skin graft to induce functional repair of damaged tissues. Even by intravenous injection, S100A8 and S100A9 can mobilize bone marrow mesenchymal stem cells to peripheral blood. Thus, S100A8 and S100A9 can also be administered via peripheral circulation to tissues located deep inside the body where local administration is difficult (brain, heart, spinal cord, etc.). The present inventors believe that effects such as shortening the healing time, functional regeneration of damaged tissues, and such can be expected in the healing process for not only damaged skin tissues but also various damaged tissues such as brain, muscle, and bone by using the present invention in pharmaceuticals, which enables local mobilization of the bone marrow-derived tissue stem cells including mesenchymal stem cells in regeneration of damaged tissues.

40

The invention claimed is:

1. A method for promoting tissue regeneration, wherein said method comprises the steps of:
  1) identifying a tissue having a damaged site in need of regeneration;
  2) administering an effective amount of a composition to a tissue other than the tissue having the damaged site in need of regeneration, wherein the composition comprises any one of:
    (a) an S100A8 protein;
    (b) a cell that secretes an S100A8 protein; and
    (c) a vector comprising a DNA encoding an S100A8 protein;
  wherein, upon administering the composition to the tissue other than the tissue having the damaged site in need of regeneration, bone-marrow derived cells migrate to the damaged tissue site in need of regeneration and cause the regeneration of the damaged tissue site in need of regeneration by differentiation at the damaged tissue site in need of regeneration, wherein the bone-marrow derived cells are mesenchymal stem cells (MSCs), and
  3) performing at least one of the following additional steps:
    (i) detecting bone-marrow derived mesenchymal stem cells at the site of the damaged tissue site in need of regeneration; and
    (ii) detecting biochemical markers of bone-marrow derived mesenchymal stem cells at the damaged tissue site in need of regeneration;
  wherein the tissue having the damaged site in need of regeneration is selected from the group consisting of muscle tissue, adipose tissue, cardiac muscle tissue, nerve tissue, pulmonary tissue, gastrointestinal tissue, hepatic tissue, biliary tissue, pancreatic tissue, and genitourinary organs, and
  wherein said S100A8 protein of (a), (b) and (c) is not used in a heterodimer with a S100A9 protein or in combination with a S100A9 protein.

2. The method of claim 1, wherein the administration is parenteral administration.

3. The method of claim 2, wherein the administration is via injection.

4. The method of claim 1, wherein the administration is intravascular, intramuscular, subcutaneous, intradermal, or intraperitoneal administration.

5. The method according to claim 1, which promotes the regeneration of a nerve tissue.

6. The method of claim 1, wherein the administration is intravascular, intramuscular, subcutaneous, or intradermal administration.

* * * * *